(12) United States Patent
Nadkarni et al.

(10) Patent No.: US 10,359,361 B2
(45) Date of Patent: Jul. 23, 2019

(54) LASER SPECKLE MICRO-RHEOLOGY IN CHARACTERIZATION OF BIOMECHANICAL PROPERTIES OF TISSUES

(71) Applicant: The General Hospital Corporation, Boston, MA (US)

(72) Inventors: Seemantini K. Nadkarni, Cambridge, MA (US); Zeinab Hajjarian, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/431,372

(22) Filed: Feb. 13, 2017

(65) Prior Publication Data

US 2017/0248518 A1 Aug. 31, 2017

Related U.S. Application Data

(63) Continuation-in-part of application No. 13/985,945, filed as application No. PCT/US2012/025783 on Feb. 20, 2012, now Pat. No. 9,618,319.

(Continued)

(51) Int. Cl.
*G01N 21/47* (2006.01)
*G01N 33/483* (2006.01)
*G01N 15/00* (2006.01)

(52) U.S. Cl.
CPC ......... *G01N 21/4788* (2013.01); *G01N 15/00* (2013.01); *G01N 21/4795* (2013.01);
(Continued)

(58) Field of Classification Search
CPC ............... G01N 21/4788; G01N 15/00; G01N 33/4833; G01N 21/4795;
(Continued)

(56) References Cited

U.S. PATENT DOCUMENTS 3,950,103 A * 4/1976 Schmidt-Weinmar .... G01J 9/02
356/450
4,377,343 A * 3/1983 Monson ................... G01B 9/02
244/130

(Continued)

FOREIGN PATENT DOCUMENTS

WO 2015160418 A2 10/2015

OTHER PUBLICATIONS

Hajjarian et al. (Correction of optical absorption and scattering variations in laser speckle rheology measurements, Opt. Express, vol. 22, 6, pp. 6349-6361)), hereinafter Hajjarian.*

(Continued)

*Primary Examiner* — Mohamed K Amara
(74) *Attorney, Agent, or Firm* — Quarles & Brady LLP

(57) ABSTRACT

Laser speckle microrheology is used to determine a mechanical property of a biological tissue, namely, an elastic modulus. Speckle frames may be acquired by illuminating a coherent light and capturing back-scattered rays in parallel and cross-polarized states with respect to illumination. The speckle frames may be analyzed temporally to obtain diffuse reflectance profiles (DRPs) for the parallel-polarized and cross-polarized states. A scattering characteristic of particles in the biological tissue may be determined based on the DRPs, and a displacement characteristic may be determined based at least in part on a speckle intensity autocorrelation function and the scattering characteristic. A size characteristic of scattering particles may be determined based on the DRP for the parallel polarization state. The mechanical property may be calculated using the displacement and size characteristics.

31 Claims, 32 Drawing Sheets

Related U.S. Application Data

(60) Provisional application No. 61/444,192, filed on Feb. 18, 2011, provisional application No. 62/420,948, filed on Nov. 11, 2016, provisional application No. 62/294,453, filed on Feb. 12, 2016.

(52) U.S. Cl.
CPC ... *G01N 33/4833* (2013.01); *G01N 2021/479* (2013.01); *G01N 2021/4792* (2013.01)

(58) Field of Classification Search
CPC ..... G01N 2021/4792; G01N 2021/479; G01N 21/45; G01N 23/046; G01N 2223/419; G01N 2021/4709; G01N 21/49; C08F 2/44; C08F 210/08; C08F 210/16; C08F 4/6495; C08F 4/6543; C08F 10/14; C08F 110/06; C08F 22/04; C08F 4/30; G01B 11/0633; G01B 7/085; G01B 9/02; G01B 9/02091; G01B 11/2441; G01B 9/02027; G01B 2290/45; G01B 9/02004; G01B 9/02057; G01B 9/04; G01B 9/02002; G01B 2290/35; G01B 9/0209; G01J 11/00; G01J 9/02; G02B 26/001; G02B 26/06; G02B 21/0028

See application file for complete search history.

(56) References Cited

U.S. PATENT DOCUMENTS

| | | | | |
|---|---|---|---|---|
| 5,686,661 A * | 11/1997 | Singh | ...................... | G01N 11/00 73/54.02 |
| 6,181,430 B1 * | 1/2001 | Meyer | ................ | G01B 9/02007 356/495 |
| 7,551,293 B2 * | 6/2009 | Yelin | .................. | G01B 11/2441 356/456 |
| 7,597,443 B2 * | 10/2009 | Fujii | ..................... | A61B 3/1233 351/205 |
| 8,467,067 B2 * | 6/2013 | Ishii | ...................... | G01J 3/4412 356/450 |
| 8,705,040 B2 * | 4/2014 | Trainer | .................. | G01B 11/08 356/338 |
| 8,797,514 B2 * | 8/2014 | Chou | ..................... | G01N 21/49 356/28.5 |
| 8,948,846 B2 * | 2/2015 | Pan | ...................... | A61B 5/0066 356/479 |
| 9,291,444 B2 * | 3/2016 | Matsuda | ................... | G01J 3/02 |
| 9,341,564 B2 * | 5/2016 | McNeil-Watson | .... | B01L 3/5025 |
| 2003/0232895 A1 * | 12/2003 | Omidian | ............... | A61K 9/0065 521/99 |
| 2006/0114467 A1 * | 6/2006 | Nicoli | ..................... | G01N 21/51 356/450 |
| 2008/0221814 A1 * | 9/2008 | Trainer | .................. | G01B 11/08 702/70 |
| 2008/0262359 A1 * | 10/2008 | Tearney | ............. | A61B 1/00096 600/476 |
| 2009/0275812 A1 * | 11/2009 | Reichgott | ............ | A61B 5/0066 600/310 |
| 2009/0276188 A1 * | 11/2009 | Cui | ............................ | G01J 9/02 702/189 |
| 2010/0128276 A1 * | 5/2010 | De Groot | ........... | G01B 11/2441 356/450 |
| 2010/0239672 A1 * | 9/2010 | Kemeny | ................ | B82Y 30/00 424/487 |
| 2010/0277742 A1 * | 11/2010 | McMillan | .......... | G01N 15/1463 356/450 |
| 2010/0284016 A1 * | 11/2010 | Teitell | ..................... | G01J 3/453 356/451 |
| 2011/0043607 A1 * | 2/2011 | Grier | ................... | G01N 15/0227 348/40 |
| 2012/0105858 A1 * | 5/2012 | Popescu | ............. | G01N 15/1434 356/450 |
| 2012/0170049 A1 * | 7/2012 | Doran | ..................... | G01B 11/02 356/496 |
| 2012/0307035 A1 * | 12/2012 | Yaqoob | ..................... | G01B 9/04 348/79 |
| 2014/0036272 A1 * | 2/2014 | Nadkarni | ........... | G01N 21/4795 356/450 |
| 2014/0178865 A1 * | 6/2014 | Reed | .................. | G01B 11/0675 435/6.1 |
| 2015/0276571 A1 * | 10/2015 | Hajjarian | ............... | G01N 21/41 73/54.02 |
| 2016/0097716 A1 * | 4/2016 | Gulati | ............... | A61B 5/02416 250/339.01 |

OTHER PUBLICATIONS

Hajjarian et al. (Correction of optical absorption and scattering variations in laser speckle rheology measurements, Opt. Express, vol. 22, 6, pp. 6349-6361 (2014)).*

Hajjarian, et al., Estimation of Particle Size Variations for Laser Speckle Rheology of Materials, Optics Letters, 2015, 40(5):764-767.

PCT International Search Report and Written Opinion, PCT/US2017/17684, dated May 4, 2017, 15 pages.

* cited by examiner

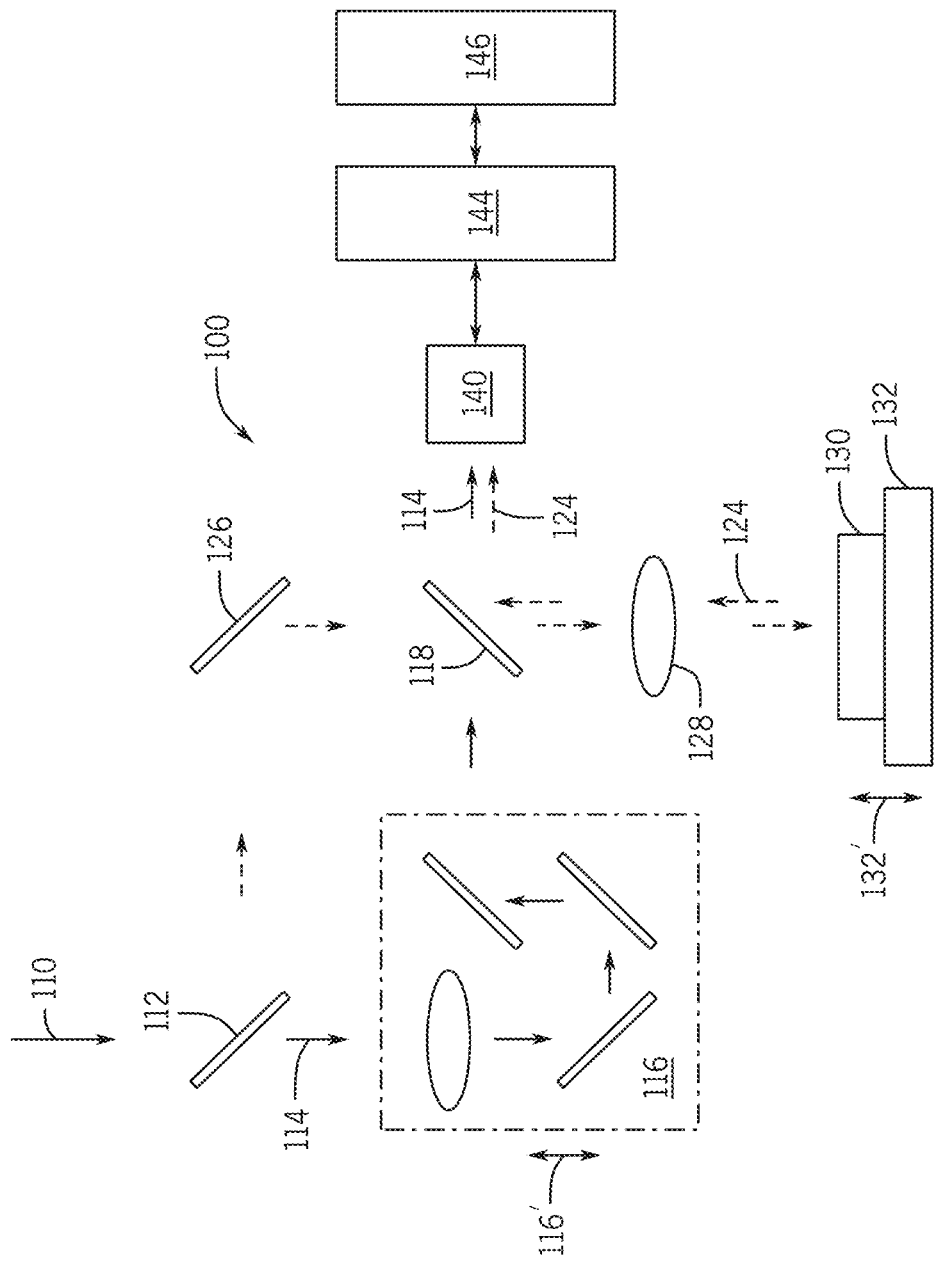

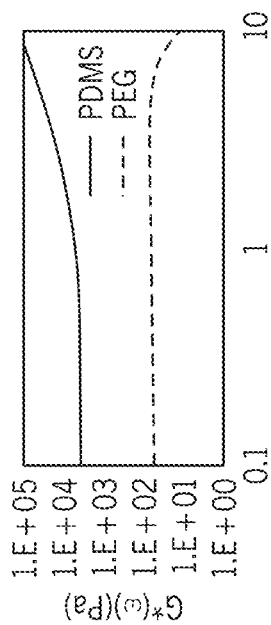
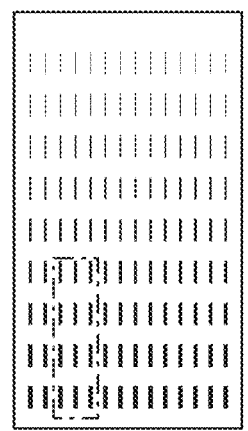
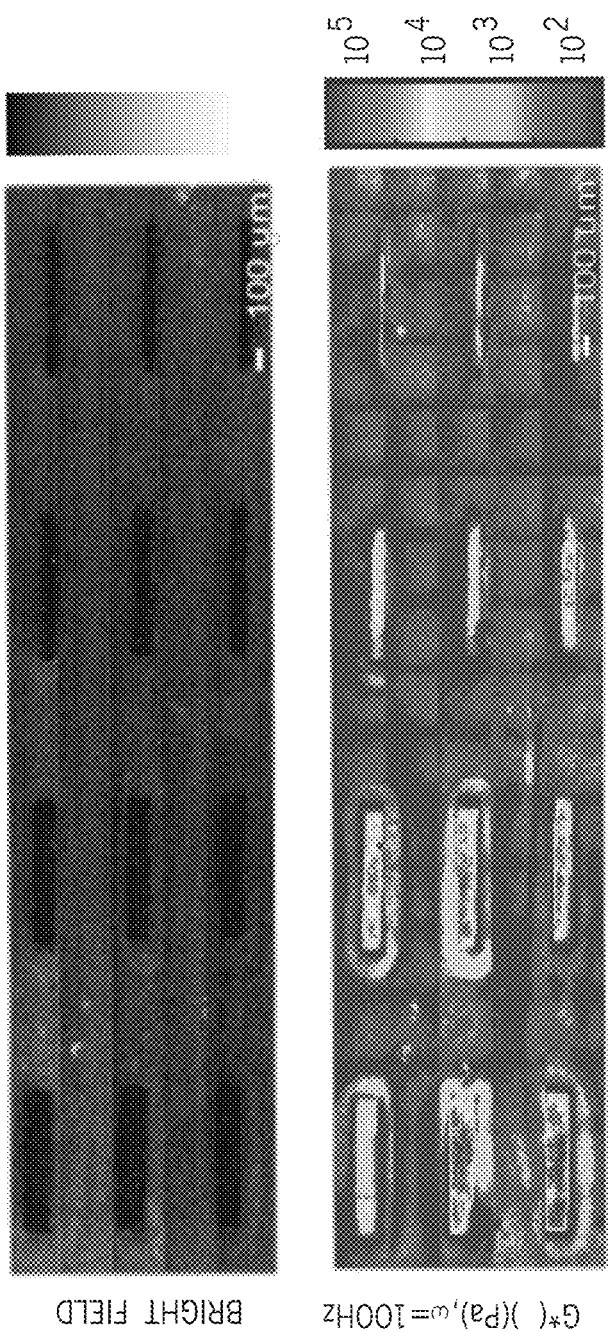

(3%A-1%B) PA

10% PEGDA

3% AGAROSE

LASER SPECKLE MICRO-RHEOLOGY IN CHARACTERIZATION OF BIOMECHANICAL PROPERTIES OF TISSUES

CROSS REFERENCE TO RELATED APPLICATIONS

This application claims the benefit of U.S. Provisional Patent Application No. 62/294,453 filed Feb. 12, 2016, as well as U.S. Provisional Patent Application No. 62/420,948 filed Nov. 11, 2016. The disclosure of each of the above-cited applications, as well as the references cited therein, is hereby incorporated by reference.

TECHNICAL FIELD

The present invention relates to measurements of mechanical properties of a biological tissue and, more particularly, to measurements of such properties with cellular resolution with the use of a laser speckle microrheometer.

BACKGROUND ART

It is recognized that progression of such diseases as cancer and atherosclerosis, for example, and other debilitating disorders including neurodegenerative disease and osteoarthritis, is accompanied by changes in stiffness of biological tissue. Recent advances in the field of mechanobiology establish that these changes in the stiffness of the extra-cellular matrix (ECM) are not merely passive consequences of earlier causal events, but may in turn influence the behavior of tissue cells, thereby possibly further exacerbating the disease. The biological cells are mechanosensitive in that they feel, perceive, and respond to the mechanical properties of their ECM microenvironment. For example, a cell senses stiffness by exerting tension as it anchors and pulls on the ECM via focal adhesion sites that involve transmembrane integrins and a network of intracellular mechanosensory proteins. Mechanical cues received from the ECM are relayed and translated by intracellular signaling pathways that, in turn, influence cell morphology, differentiation, proliferation, contractility and elasticity. Behavior of the cells that have been altered affects a dynamic balance between the ECM production and break down, thereby causing the ECM stiffness to be changed further. As a result, a positive feedback loop is established with consequences that are sometimes detrimental to the cell's health. For example, the altered ECM stiffness can induce epithelial tumor progression, switch on the malignant phenotype in tumor cells, cause smooth muscle cell proliferation in atherosclerosis, enhance the angiogenesis potential of endothelial cells, initiate calcium deposition by interstitial cells in cardiac valves, modulate stem cell differentiation, and induce cell apoptosis. The cellular response was shown to be regulable via tuning the ECM mechanical properties to values comparable with those of a normal tissue.

Changes in the mechanical properties of the ECM may provide the early detectable signs of the disease onset that likely precede aberrant intracellular signals. Moreover, by engineering the ECM mechanical properties it may be possible to reverse the progress of the disease. Therefore, the capability to measure and monitor minute changes in the ECM stiffness at the size scale sensed by cells (referred to herein as cellular spatial scale) is vital in advancing current understanding in mechanobiology and may, quite possibly, enable not only the detection of the initial onset of a number of critical diseases but also the guidance of an early therapeutic intervention in case of such diseases.

The currently used systems and method are adapted to in vitro studies that evaluate the impact of global (or bulk) ECM mechanical properties on condition of the cells. In contradistinction, however, the biological cells probe the stiffness of their local microenvironment on a substantially smaller scale, via micron-sized focal adhesions and, due to tissue heterogeneities and matrix remodeling, the ECM micromechanical environment that a cell perceives is vastly different from the bulk mechanical environment. The majority of the hypotheses in mechanobiology, generated from experiments in monolayer cell models, fail to recapitulate the complex three-dimensional (3D) environment that a cell experiences in vivo. It is well established that cellular behavior is profoundly different in 3D models where the influence of the ECM composition and stiffness is far more complicated compared to the two-dimensional (2D) monolayer models. Accordingly, there remains a question of how mechanobiological relationships translate into biologically relevant 3D disease models and in clinically relevant systems in vivo. However, no means exists today that enable measurements of the ECM stiffness in 3D at microscopic size scales relevant to the microenvironment of a biological cell.

It is increasingly appreciated that the ECM, also known as the tissue scaffolding, not only provides mechanical stability and tissue organization, but also imparts critical biochemical and biomechanical cues. Such cues actively direct cell growth, survival, and migration, and govern vascularization and immune responsiveness during embryonic development, homeostasis maintenance, and disease progression. ECM biomechanical properties play a prominent role in neoplastic transformation and metastatic progression, which accounts for more than 90% of cancer-associated mortality and morbidity. In addition, these micromechanical cues are directly implicated in many fibrotic diseases, such as idiopathic pulmonary fibrosis (IPF), systemic sclerosis (SS), liver cirrhosis, and atherosclerosis, which are responsible for over 45% of deaths in the industrialized countries.

For instance, in breast cancer, the biophysical and biochemical cues from the tumor-associated ECM reinforce and fuel the progression of the neoplasia by promoting of the hallmarks of cancer. The increased ECM stiffness, sensed by focal adhesions, can activate integrins, promote focal adhesion assembly, and/or stimulate the mechano-sensory pathways. This activation increases cytoskeletal tension via acto-myosin contractility. This, in turn, can accelerate the secretion, deposition, and cross linking of ECM macromolecules by host stromal cells, and results in further increases in ECM stiffness, completing a self-enforcing vicious cycle. In addition, interference between cytoskeletal tension and the epidermal growth-factor receptor (EGFR) pathways can result in increased proliferation of cancer cells. The biophysical properties of ECM are also known to promote pro-migratory trails by inducing epithelial-mesenchymal transition. By increasing the VEGF signaling, ECM stiffening can also provoke angiogenesis. Further, increased ECM density and rigidity can amplify the interstitial fluid pressure and hamper drug delivery, promoting biophysical drug resistance.

Apart from solid tumors, the micromechanical signature of ECM is also directly implicated in the development of numerous fibrotic disorders. One such disease is IPF, a devastatingly progressive fibrosis of the lungs that destroys the normal alveolar structures and impairs oxygen transfer to the blood stream. The etiology of IPF is not well understood, yet ECM micromechanics are believed to be directly involved in the pathogenesis of IPF. Stiffening of ECM activates the mechano-sensory circuitry of fibroblasts, in turn promoting contractility, proliferation, acquired resistance to apoptosis, and differentiation to contractile myofibroblast phenotype. The subsequent increased collagen synthesis and accumulation continuously translates the mechanical stimuli into fibrogenic signals and vice-versa. Despite the ubiquitous role of ECM micro-mechanics in normal lung development and pulmonary disorders such as IPF, our current understanding of ECM mechanics is limited. The currently available models of lung biomechanics are overly simplified, ignoring the local tissue heterogeneity at cellular scales.

Irregular ECM micromechanics are also involved in the initiation and progression of systemic sclerosis (SS) or scleroderma. The limited cutaneous scleroderma affects only the skin on the face and limbs, whereas the diffuse type is likely to damage internal organs such as kidneys, heart, lungs, and digestive tract. Currently, the cause of SS is unknown and no pharmacotherapy is available for this deadly disease. However, it is believed that onset of SS is triggered by an injury followed by an aberrant wound healing response which involves activation of inflammatory pathways, accumulation of collagen and other fibrous proteins, and ECM stiffening within the dermis. As in IPF, the host stromal cells within the ECM transform into persistent myofibroblasts. The subsequent excessive deposition of ECM creates a feed-forward loop with catastrophic consequences. The ability to quantify and map ECM micromechanical properties is crucial for finding novel therapies that target the ECM.

Evaluating the ECM viscoelastic properties at microscale, as perceived by the cells, may help us understand the mechanical regulation of many diseases. In addition, it may provide a strong diagnostic tool for staging the disease, tailoring effective and personalized therapeutic strategies, and monitoring the efficacy of the treatments. It may also open new prognostic and therapeutic avenues that target ECM mechanical properties to reverse the course of the disease and regress its progression.

Apart from differentiating between natural tissue scaffolds in healthy and disease states, diagnosis of malignancies, understanding the etiology and pathogeneses of multiple conditions, and devising therapeutic approaches based on regulating the mechanical properties of tissues, the ability to evaluate the viscoelastic properties at multiple spatial scales is invaluable for design and development of synthetic tissue scaffolds, biomaterials, and hydrogels. This is because biomaterials and hydrogels are increasingly used in tissue engineering, regenerative medicine, drug-delivery, and mechanobiology research owing to their unique properties, including biocompatibility, tunable compliance, deformability and stress resilience. To fully integrate into biological systems, biomaterials and tissue scaffoldings often exhibit distinct viscoelastic properties at different length scales. The macro-scale viscoelastic endurance of biomimetic scaffolds enables them to withstand the physiological and hemodynamic loads. The micro-scale compliance, on the other hand, confers mechanical stimuli that direct cellular growth and differentiations and control molecular dynamics such as the gas and nutrients exchange, and drug-release. The growing demand for design, development, quality control, and performance monitoring of biomimetic constructs calls for novel tools capable of evaluating the viscoelasticity of biomaterials, in their native state, at different deformation rates and multiple length-scales, without manipulation.

The bulk mechanical properties of materials are often quantified by the frequency dependent shear viscoelastic modulus, $G^*(\omega)=G'(\omega)+i\ G''(\omega)$. Here, $G^*$ is the shear viscoelastic modulus and $\omega$ is the oscillation frequency of the loading condition. Moreover, $G'$, the real part of $G^*$, is the elastic modulus, representing the solid-like behavior of the sample, and $G''(\omega)$, the imaginary part of $G^*$, is the viscous modulus, characterizing the fluid-like trait of the specimen. Traditionally, $G^*(\omega)$ is evaluated by a mechanical rheometer in a destructive process by placing the specimen between two parallel plates and applying a sinusoidal shear strain, $\varepsilon(\omega)$, to the specimen. Here, $\omega$ is the angular oscillation frequency with the units of radians per second (rad/s). The consequent oscillatory stress induced within the sample, $\sigma(\omega)$, has both an in-phase component and an out-of-phase component with respect to $\varepsilon(\omega)$. The rheometer senses the torque and the displacement of the plates and retrieves the stress and strain magnitudes. Subsequently, $G^*(\omega)$ is measured by calculating the ratio of applied stress to the resulting strain, i.e. $\sigma(\omega)/\varepsilon(\omega)$, over a small frequency range. The ratio of the in-phase component of stress to the strain accounts for elastic (or storage) modulus. Besides, the ratio of stress component with 90-degree phase-lag with respect to strain represents the viscous (or loss) modulus. Alternatively, in the stress-controlled rheometers, a constant shear stress is applied to the specimen at various oscillation frequencies and the strain is evaluated. As for the case of strain-controlled rheometers, $G^*$ is evaluated by calculating the stress-strain ratio. Measuring the average bulk response over the entire sample volume in the rheometer precludes the inquiry of local mechanical heterogeneities and yields only the volume-averaged mechanical response of the specimen. Moreover, this type of mechanical test requires relatively large sample volumes and is not conducive for rare and precious biomaterials and tissue specimens.

The micro-scale mechanical properties of materials are conventionally probed using micro- and nano-indentation methods such as Atomic Force Microscopy (AFM)-based indentation, also known as force-mapping mode or force spectroscopy. The AFM force spectroscopy is a surface probing technique, capable of providing local elasticity maps of samples such as the ECM, live cells, and sub-cellular organelles. In force spectroscopy, a small micron-sized metallic tip is fixed in the proximity of a flexible cantilever. The cantilever is mounted on a high-precision piezoelectric stage, which controls the displacement of the tip with nano-meter precision. The pyramidal end of the tip may directly indent the sample. Alternatively, and more prevalently, a polystyrene bead of a few microns diameter may be glued at the tip end to increase the contact area.

Although the nominal value of the cantilever spring-constant is often provided by the manufacturer, it is imperative that a certain set of calibration steps be followed to re-evaluate the exact spring constant of the cantilever prior to measurements. This can be done, for instance, by thermal noise method via balancing of the ambient thermal energy of the cantilever environment with its free vibration and finding the resonance frequency. A Lorenzian model is fit to the resonance peak and the area under the curve is calculated as a measure of the resonance energy or tip deflection. By dividing the ambient thermal energy to the area under the curve, the exact spring constant of the cantilever is calculated.

Also vital to AFM operation is a calibration step that enables retrieving the cantilever deflection from the actual measured values, that is, detected voltage. In this procedure, the tip is lowered until it comes into physical contact with a hard calibration specimen, such as a glass slide. Since the hard calibration sample does not move, the deflection of the cantilever is equivalent to its displacement. This enables calculation of the conversion factor that relates the recorded voltage, the actual measured value, to the cantilever deflection.

After these cumbersome calibration steps, one may proceed to the force spectroscopy measurements of the specimen. As mentioned earlier, the cantilever is mounted on a precision z-stage. The z-stage is displaced so that the tip approaches, comes into physical contact, and presses further into the sample. As the tip pokes the specimen, the cantilever is deflected. To measure this deflection, a laser beam is focused at the extremities of the metallic tip. The reflection of the laser beam is monitored by a segmented photo-detector. Deflection of the cantilever stirs the laser beam, enabling the position-sensitive photo-detector to retrieve the deflection of the cantilever. Subsequently, Hooke's law is used to calculate the force as the product of cantilever deflection and spring constant. The force placed on the tip increases as it pokes and presses further into the sample, reaching a preset control value. Subsequently, the force is removed and the tip retracts. The z-stage displacement is plotted against the applied force during both the approach and retract phases. An appropriate model is fit to this force-distance curve to calculate the indentation modulus (E) of the specimen. This process needs to be repeated for each and every point on the sample within the region of interest. Towards this end, a pair of piezoelectric precision x-y stages translates either the cantilever or the sample to enable probing the entire region of interest. At each measurement point, the tip approaches towards and retracts back from the sample. Given that the approach-retract step takes at least a few seconds, the force-mapping AFM measurements are tediously time-consuming. Moreover, due to their contact-based nature, the indentation-based technologies are inherently invasive. In addition, the depth probed by the tip does not exceed a few microns, limiting AFM to a surface probe modality. Finally, the indentation modulus is merely reflecting the elastic behavior at a fixed indentation rate and does not probe the frequency-dependence or the dynamic viscosity.

SUMMARY OF THE INVENTION

Embodiments of the present invention provide a method for forming a three-dimensional (3D) map, of a micromechanical property of a biological tissue, that has microscopic spatial resolution in all three dimensions.

Such method includes calculating two-dimensional (2D) distributions of a viscoelastic parameter representing the mechanical property at tissue depths. Each 2D distribution is calculated from optical data representing light scattered only by a biological tissue layer that is located at the respectively corresponding depth and that is limited in thickness by a parameter related to a coherence length of used light. The method further includes mapping the calculated 2D distributions into a 3D data set representing the 2D distributions in relation to the depths of corresponding tissue layers.

In one embodiment, the calculation of 2D distributions includes calculating each 2D distribution based on optical data representing light scattered only by a biological tissue layer defined via interferometric coherence-gating of light detected with said optical detector. In a related embodiment, the calculation of 2D distributions includes a calculation based on optical data that represents Brownian motion displacements of intrinsic light-scattering particles of the biological tissue. In a specific embodiment, for example, the calculation of 2D distributions includes detecting an optical interferogram by overlapping a sample distribution of light (that has been transmitted to the biological tissue through a sample train of optical components and has interacted with the tissue layer) and a reference distribution of light (that has passed through a reference train of optical components including an optical delay line having a variable optical delay length). The sample and reference distributions of light are mutually coherent. The specific embodiment of the method further contains mathematically reconstructing the detected interferogram to form a spatially-filtered optical interferogram. Optionally, the depth at which the tissue layer is located is defined by an optical distance between a component of at least one of the sample and reference trains of optical components and the biological tissue. Optionally, the calculation of the 2D distribution involves repositioning of an optical component of the sample train and adjusting a variable optical delay length by an amount optically matching said incremental amount and, in particular, changing the optical delay length.

An embodiment of the method optionally further includes at least one of color-coding of the calculated 2D distribution of the viscoelastic parameter (carried out depending at least in part on a value of said viscoelastic parameter) and displaying at least one of said color-coded 2D distribution and the 3D data set into which the calculated 2D distributions are mapped.

Embodiments of the present invention additionally provide for a method for forming a three-dimensional (3D) map of a micromechanical property of a biological tissue with microscopic resolution. Such method includes: (i) detecting an optical interferogram, at the optical detector, by overlapping the mutually coherent sample distribution of light (that has been transmitted to the biological tissue through a sample train of optical components and has interacted with a tissue layer) and reference distribution of light (that has passed through a reference train of optical components including an optical delay line having a variable optical delay length); (ii) calculating a two-dimensional (2D) distribution of a viscoelastic parameter representing the mechanical property of the biological tissue from optical data representing speckle fluctuations and corresponding to the detected interferogram; and (iii) associating the calculated 2D distribution of the viscoelastic parameter with a depth of the tissue layer within the biological tissue. The depth of the layer, with which the sample distribution of light has interacted, within the tissue is defined by an optical distance between a component of at least one of the sample and reference trains of optical components and the biological tissue. The method further includes mathematically reconstructing said optical interferogram including spatially-filtering said optical interferogram.

The process of detecting an optical interferogram may include detecting a sample distribution of light that has been scattered only by a tissue layer located at a predetermined depth of the tissue. Alternatively or in addition, the process of calculating a 2D distribution of a viscoelastic parameter may include calculating a 2D distribution of such parameter based at least in part on data representing Brownian motion displacements of intrinsic light-scattering particles of the biological tissue.

In a related embodiment, the method additionally includes changing the optical distance by an incremental amount and repeating the steps of detecting, calculating, and associating as defined above in order to obtain and characterize a 2D distribution of the viscoelastic parameter corresponding to a layer of tissue located at a different, changed depth within the tissue sample. Generally, the incremental amount by which the optical distance is changed does not exceed 20 microns and is preferably smaller than 10 microns and more preferably smaller than 5 microns. In a specific implementation, changing the optical distance includes repositioning of an optical component of the sample train and adjusting a variable optical delay length by an amount optically matching said incremental amount. Detection of an optical interferogram optionally includes detection of a sample distribution of light that is defocused with respect to a boundary of the biological tissue, while changing the optical distance optionally includes adjusting the variable optical delay length. The method may additionally include displaying calculated 2D distributions as a 3D map of a geometrical distance parameter corresponding to the optical distance. The method may additionally include transforming 2D distributions calculated as a functions of depths of the tissue layers into the 3D map representing a 3D microscopically-resolved distribution of a mechanical property of the tissue.

Alternatively or in addition, the method optically includes at least one of color-coding the calculated 2D distribution of the viscoelastic parameter depending at least in part on a value of the viscoelastic parameter and displaying the calculated 2D distribution of the viscoelastic parameter as a function of a geometrical distance parameter corresponding to said optical distance.

Embodiments of the invention further provide a visually-perceivable representation of a three-dimensional (3D) distribution of stiffness of a biological tissue formed a process including:

(i) an acquisition of multiple sets of optical data from light distributions at an optical detector (such that each of these light distributions corresponds to an optical interferogram formed by spatially overlapping sample and reference mutually coherent beams of light, where the sample beam of light interacted with the biological tissue and the reference beam of light passed through a line of variable optical delay, different interferograms corresponding to at least one of different optical delays and different depths of the biological tissue;

(ii) a determination, from the acquired multiple sets of optical data, of respectively corresponding two-dimensional (2D) distributions of a viscoelastic modulus of the biological tissue; and (iii) displaying the determined 2D distributions for visualization as a function of a parameter representing at least one of said different optical delays and different depths of the biological tissue.

In one embodiment, at least one of the acquisition of multiple sets of optical data and the determination of the 2D distributions is made at least in part based on Brownian motion displacements of intrinsic light-scattering particles of the biological tissue.

In the provided visually-perceivable representation, at least one of the 2D portions of the representation is color-coded in relation of values of the viscoelastic modulus. In a specific embodiment, the visually-perceivable representation includes an image representing, with microscopic resolution, a volumetric distribution of a viscoelastic modulus in said biological tissue.

Moreover, embodiments of the invention, provide a computer program product for determining a volumetric distribution of a micromechanical parameter characterizing a biological tissue, the computer program product containing a computer usable tangible medium having computer readable program code thereon, which computer readable program includes at least (i) program code for calculating two-dimensional (2D) distributions of a viscoelastic parameter representing the micromechanical property at tissue depths that respectively correspond to the 2D distributions (where each 2D distribution is calculated from optical data representing light scattered only by a biological tissue layer located at the respectively corresponding depth and that is limited in thickness by a parameter related to a coherence length of said light, said light being detected with an optical detector); and (ii) program code for mapping the calculated 2D distributions into a 3D data set representing, with microscopic resolution, these 2D distributions in relation to the corresponding depths of the tissue sample. In addition, the computer program product optionally includes at least one of program code for calculating a 2D distribution from optical data representing light scattered only by a biological tissue layer defined via interferometric coherence-gating of light detected at the optical detector; program code for color-coding a calculated 2D distribution of the viscoelastic parameter depending at least in part on a value of the viscoelastic parameter; and program code for displaying at least one of a color-coded 2D distribution and the 3D data set into which the 2D distributions have been mapped.

The embodiment of a computer program product may optionally include program code for reconstructing an optical interferogram formed by overlapping a sample distribution of light (which has been transmitted to the biological tissue through a sample train of optical components and has interacted with a tissue layer) and a reference distribution of light (which has passed through a reference train of optical components including an optical delay line having a variable optical delay length). The reconstruction of an optical interferogram is configured, at least in part, to produce a spatially-filtered interferogram. Finally, an embodiment may also include program code for adjusting the variable optical delay length of the reference train of optical components by an incremental amount.

BRIEF DESCRIPTION OF THE DRAWINGS

The invention will be more fully understood by referring to the following Detailed Description in conjunction with the Drawings, of which:

FIG. 1B is a diagram showing schematically an embodiment of the system of the invention.

FIG. 3A: a bright-field microscopy image. FIG. 3B: a laser-speckle pattern. FIG. 3C: a reconstructed color-map of stiffness.

FIG. 15A is related to the scatter diagram of $|G^*|$ at 1 Hz evaluated by LSM and conventional rheology, and FIG. 15B is related to the scatter diagram of LSR-measured $|G^*(\omega)|$ values at 1 Hz evaluated using LSM and the indentation modulus, $|E|$, evaluated by AFM FIG. 16A depicts an exemplary photomask design used to fabricate a polydimethylsiloxane-polyethylene glycol (PDMS-PEG) phantom.

FIG. 16B depicts two-dimensional (2D) curves corresponding with the viscoelastic modulus of the constituents of the phantom, namely PEG and PDMS, as measured using a mechanical rheometer.

FIG. 16C displays the bright field image of the construct of FIGS. 16A and 16B.

FIG. 16D shows a 2D map of $G^*$ evaluated using an exemplary LSM system.

DETAILED DESCRIPTION

Figure 1A:
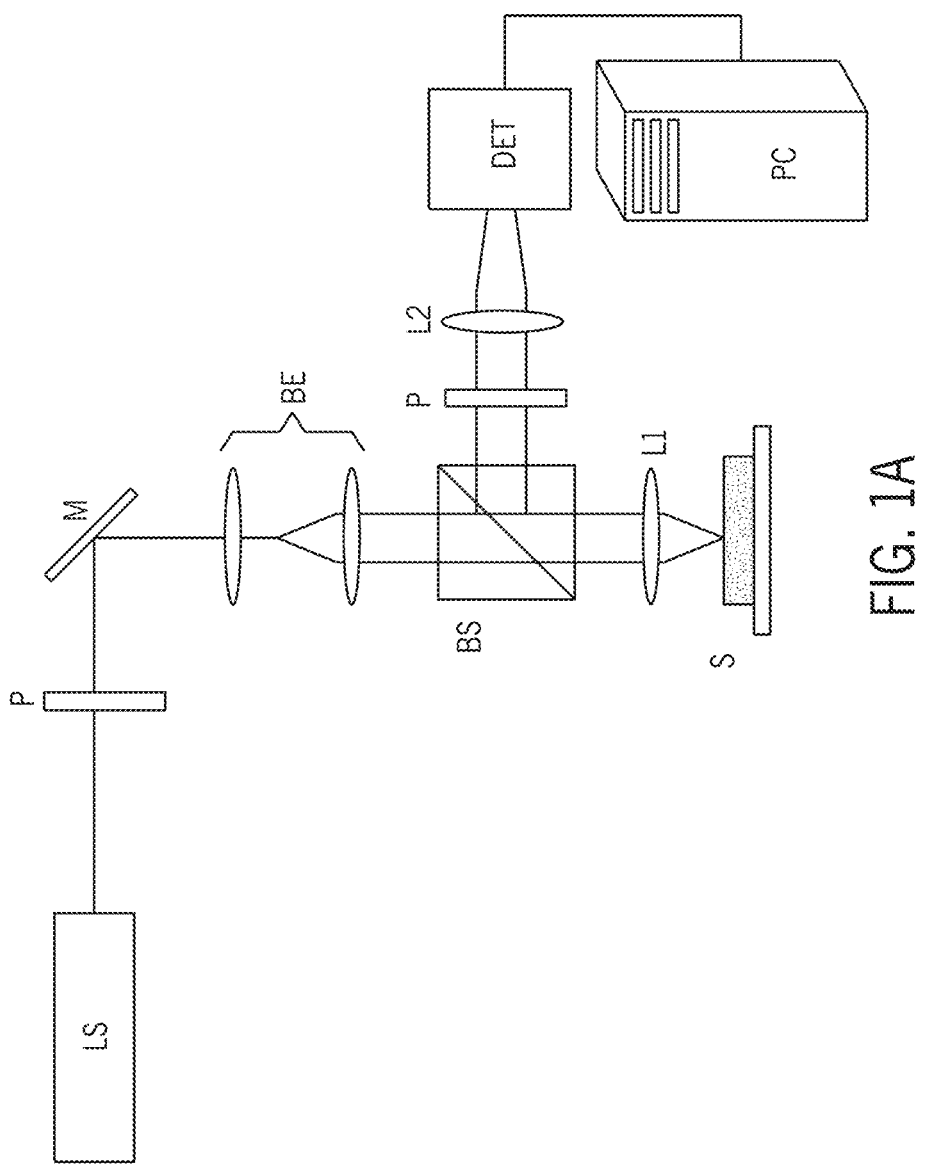
FIG. 1A is a diagram of a conventional set-up for laser speckle measurements.

In accordance with preferred embodiments of the present invention, a Laser Speckle Microrheometer (LSM) system is disclosed, as well as multiple corresponding passive and active methods of depth-resolved speckle microrheometry, that facilitate the measurements of 3D mechanical properties of a biological tissue with cellular-scale (on the order of several microns, for example 1 to 20 microns, preferably 1 to 10 microns, and more preferably 1 to 5 microns) resolution with high sensitivity in order to monitor small changes in the ECM stiffness.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, if the schematic flow-chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The invention as recited in claims appended to this disclosure is intended to be assessed in light of the disclosure as a whole.

Stiffening of tissue has been an informative indicator of various medical conditions. Desmoplastic stiffening that accompanies neoplasia, for example, has traditionally provided a viable metric to detect tumors in the clinic via physical palpation or by imaging tools. Recent studies indicate that this increased stiffening is not merely a result of tumorigenesis, but may actively drive oncogenic signaling and regulate tumor growth, invasion and metastasis. For example, the ECM stiffness has been shown to regulate tumor cell morphology, proliferation, migration, differentiation, and malignant transformation. Stiffness gradients can drive migration of cancer-associated fibroblasts and macrophages and impact myofibroblast contractility. Stromal stiffness also influences treatment efficacy: the stiffer ECM is more resistant to drug penetration, while heightening cell resilience to drug induced apoptosis, which suggests mechanical information is crucial in order to develop therapies that counter drug resistance. Although the mechanisms by which the ECM mechanics orchestrate tumor evolution remain unclear, there are indications that cells sense stiffness via transmembrane integrin receptors that couple the ECM with the actin cytoskeleton. The ECM stiffening has been shown to induce integrin clustering, reinforces cell-ECM focal adhesions and activates mechanosensory proteins that trigger mitogenic signaling and impact actomyosin contractility, causing further ECM stiffening. As a result, a positive feedback loop is established connecting extracellular mechanical cues with intracellular signaling pathways that regulate cell proliferation, differentiation and migration. Tumor pathogenesis is thus driven by this cooperative dialogue between ECM mechanics and oncogenic signaling, underscoring the fact that knowledge of the ECM mechanical properties is equally crucial in advancing our understanding of cancer etiology, and developing new therapies and prognostic indicators to manage cancer.

Current insights on this mechano-biological dialogue between the ECM and cell signaling however are mostly limited to 2D monolayer cultures that fail to recapitulate the complex 3D microenvironment a cell perceives in vivo. Yet, it is well established that cell behavior is profoundly different in 3D ECMs likely due to distinct 3D fiber architecture and compliance. Furthermore, majority of the hypotheses in the field have been generated by studying the impact of bulk stiffness integrated over the entire substrate. Cells however probe the ECM via micron-sized focal adhesions; and due to micro-scale variations in fiber density, microstructure and pore size the mechanical environment a cell perceives is vastly different from the bulk environment. Due to these limitations, crucial questions remain on how ECM mechanical regulation translates in biologically relevant disease systems.

Conventionally, mechanical properties of a tissue sample are determined via the frequency-dependent viscoelastic modulus, $G^*(\omega)$, in accord with principle of mechanical rheometry, when by the sample is sheared, for example, within a parallel plate to evaluate the stress caused in the sample over a limited range of oscillation frequency $\omega$. Substantial manipulation of the tissue sample is required in order to effectuate such measurements, thereby rendering the mechanical rheometer practically unsuitable for evaluating mechanical properties of live cells. Therefore, only a static snapshot of bulk mechanical properties averaged over large sample volumes can be obtained prior to cell seeding (such as, for example, culturing cells on a matrix prior to cell growth and proliferation). Accordingly, serial monitoring of the ECM stiffness with the use of a conventional mechanical rheometer is not feasible.

Related art also discussed nano-indentation tools that probe stiffness of the tissue surface and map this surface on a micro-scale (about 1 to 10 µm). This methodology, however, fails to provide depth-resolved measurements of the stiffness parameter(s). Another approach, referred to as bead-twisting microrheology, has been recently reported to determine a degree of rotation of micro-beads (seeded in a tissue) in a twisting magnetic or optical field and to evaluate local matrix properties based on the extent of bead rotation. While this technique demonstrates a capability for 3D measurements, difficulty in achieving uniform bead distribution limits practical application to the bead microenvironment.

We previously demonstrated the use of a so-called Laser Speckle Rheology (LSR) approach, which utilizes Laser Speckle Imaging or LSI, for non-destructive analysis of tissue. The laser-speckle based characterization of the tissue utilizes dynamic light scattering (DLS) principles, according to which the mean square displacements (MSDs) of light-scattering particles relate to the viscoelastic susceptibility of the material. According to the LSR methodology, the sample is illuminated with coherent light and images of time-varying laser speckle patterns (or, more generally, optical data corresponding to intensity fluctuations representing light scattered by the elements of the sample) are acquired using a high speed detector (for example, a CMOS camera). Laser speckle, as a phenomenon reflecting the interference of coherent light scattered by the sample, is dynamically modulated by the Brownian motion of light-scattering elements and particles which, in turn, is influenced by the viscoelastic susceptibility of the medium surrounding the light-scattering elements. Generally, the laser speckle concept is known and for that reason is not discussed here in any significant detail. The rate of speckle modulations was shown to closely relate to the mechanical properties of tissue and, in particular, to a viscoelastic modulus $G^*(\omega)$, sometimes referred to as the complex shear modulus and defined in terms of a ratio of tissue sample stress to strain applied to the sample. The real part of $G^*(\omega)$, $G'(\omega)$, referred to as the elastic or storage modulus, represents a measure of solid-like behavior of the tissue sample. The imaginary part $G''(\omega)$, which is out of phase with the applied strain, is the viscous or loss modulus and represents a measure of viscous energy dissipation by the tissue sample. A diagram illustration of a typical device currently used for characterization of laser speckle is presented in FIG. 1A, where LS denotes light source (such as a laser, for example), M is a mirror, P is a polarizer, BS indicates a beamsplitter, BE is a beam expander, L1, L2 are the lenses, S is a sample, and DET and PC are a detector and a computer system respectively. Such device and similar currently-used devices have a noticeable shortcoming in that they average the acquired optical data over the volume of the tissue sample (thus enabling evaluation of bulk characteristics, on the scale of about 1 mm$^3$). As a result of such spatial averaging, the depth-resolved information about the tissue is not acquired and, instead, is lost.

In order to enable measurement of the ECM micromechanical properties resolved in three dimensions and to obtain volumetric data, the LSM modality described in this application is adapted to combine the acquisition of full-field speckle frames with the application of dynamic light-scattering principles and interference microscopy to detect depth-resolved laser speckle modulations with the resolution of at least 1 to 20 µm or better (for example, of about 10 microns or better, and more preferably of about 5 microns or better). According to the idea of the invention, optical data representing depth-resolved images of interference (between light scattered and/or diffused by the tissue sample and a reference beam of light) is acquired and analyzed with the use of image-reconstruction methods to extract depth-resolved speckle images. The following analysis of such depth-resolved speckle images, involving dynamic light scattering principles, produces the determination of viscoelastic modulus corresponding to different depths of the tissue, from the speckle fluctuations. Consequently, the determination of micromechanical and microstructural properties of the tissue sample is performed with a single integrated instrument, thereby enabling the investigation of mechanosensitive interactions of living cells with their ECM in 3D in real time.

In contradistinction with the conventional mechanical rheometer, the use of the proposed LSM modality requires no sample manipulation, thereby rendering this device and method uniquely suited for evaluating the ECM of live cells. The LSM affords a large dynamic range (~10 Pa-1 kPa) of the viscoelastic modulus measurements to facilitate evaluation of tissues and biomimetic tissue matrices relevant to a variety of biological tissues, and possesses high sensitivity to small changes in micromechanical properties of the tissue (corresponding to a detection of the viscoelastic modulus having a value of at least 1 Pa or lower, preferably 0.1 Pa or lower, and most preferably about 0.01 mPa). Furthermore, embodiments of the LSM are adapted to measure $G(\omega)$ over an oscillating frequency range from about 0.001 kHz to hundreds of kHz (that is multiple orders of magnitude larger than that provided by a mechanical rheometer).

According to an embodiment 100 of the laser-speckle microrheometer of the invention, schematically shown in FIG. 1B, a beam 110 of light from a source of coherent light (such as a laser, in one example, not shown) is split with an appropriate beam-splitter 112 between sample and reference arms of an interferometer such as, for example, a Mach-Zehnder interferometer. (It is appreciated that a different type of interferometric system can be appropriately used instead.) A portion 114 of light passing through the reference arm of the interferometer. The reference arm of the interferometer contains an optical delay line 116, adjustable as shown with an arrow 116', and, optionally, additional optical components such as refractors, reflectors, optical filters, and the like. Having traversed the reference arm, the portion 114 of light is spatially overlapped (as shown, with the use of a beam-splitter 118) with a portion of light 124 that has traversed the sample arm of the interferometer (defined by the beam-splitters 112, 126, 118, a lens 128 such as a microscope 10× objective, NA=0.25 for example and, optionally, additional not shown optical components) and interacted with a tissue sample 130 placed on a repositionable sample holder 132. The resulting time-dependent, interfererometric image of a tissue layer, positioned at a tissue-sample depth that is defined by an optical length of the sample arm that is equal to that of the reference arm, is registered with an optical detector 140 such as a CMOS camera (for example, at a 1 kHz frame rate within a time-window of 2 seconds). The thickness of this particular tissue layer is also specifically defined via coherence-gating (interferometric gating) of light at the detector 140 in that a registered interferogram is formed with the use of light 124 scattered only at the depths of the sample 130 that are defined by coherence length of light 110. (Indeed, interference between light distributions of the sample and reference arms occurs at the detector plane when the optical path lengths of the reference and sample arms are matched to within the coherence length.) As a result, the interferogram associated with each depth of the sample 130 is substantially free of contributions of light scattered from other depths in the biological tissue outside of the tissue layer defined by the interferometric set up. In one embodiment, a low coherence length laser source is used.

Time-resolved images are measured over a finite time period, for example over 1-10 seconds to measure laser speckle fluctuations caused by Brownian motion displacements of light scattering particles at each depth. By scanning the collimated illumination beam across the sample or translating the stage large regions of interest of the tissue can be evaluated.

Optically-acquired interferometric data representing such interferometric image is further processed with a data-acquisition and processing system 144. (A separate measurement of the laser speckle optical irradiance defined by the sample tissue 130 can be optionally performed with the use of the embodiment 100 when light 114 in the reference arm is blocked, i.e. when the reference arm of the interferometer is disengaged). Imaging data representing a 2D interferometric pattern and a 2D laser speckle (LS) pattern, produced by the (interferometrically defined) tissue layer of the sample 130 within the field of view of the lens 128, are further processed by the pre-programmed data processing system 144 to determine a 2D map of distribution of mechanical parameter(s) of the tissue sample with cellular resolution afforded by the LS imaging.

To add an axial dimension to the LS microrheometric measurement, the depth-dependent (with interferometrically-defined resolution of a few microns, for example of about 1 to about 20 microns) time-varying data is acquired, generally, by scanning an optical component of either the sample or reference arm of the device 100. In one example, the axial scanning through the tissue sample 130 can be enabled by sequentially changing a distance between the objective 128 and the tissue sample 130 (such as by repositioning the sample holder 132 with respect to the lens 128 as shown with an arrow 132') and thereby refocusing light traversing the sample arm of the interferometer at different depths within the sample 130. In another example, the sample 130 is illuminated through the lens 128 with a substantially defocused light and the determination of a depth at which a given tissue layer is chosen for interferometric imaging is carried out by readjustment of the variable optical delay line 116, whereby its length is changed by a predetermined incremental amount which, in a specific case, may be defined by the coherence length of light 110. (Alternately, interferograms can be obtained by scanning over multiple wavelengths and depth-resolved images are reconstructed from interferograms that are recorded at multiple wavelengths.) In any instance, each of the acquired sets of data represents a coherence-gated 2D interferogram and is associated with a corresponding depth of the biological tissue sample 130.

Further, the acquired tissue-depth dependent sets of 2D interferometric data are mapped into a 3D data set in relation with the corresponding tissue depth at which such 2D data sets were measure. From the 3D data set, the pre-programmed data processing system 144 determines a 3D distribution of stiffness of the ECM sensed by cells of the tissue sample 130.

The interferograms acquired with an embodiment of the LSM system such as the embodiment of FIG. 1A are further processed to reconstruct 2D images corresponding to multiple depths of the sample 130 with the use of mathematical formalisms well established for holographic image reconstruction. See, for example, Schnars et al., in *Measurement Sci. Tech.*, 2002; 13:R-85-R101); Cuche et al., in *Appl. Opt.* 2000; 39; 4070-4075); Hariharan (Optical holography: Principles, techniques, and application, Cambridge Univ. Press, 1996); and Marquet P. et al., in *Opt Letts.* 2005; 30:468-470; and Montfort F. et al., in *Applied Opt.* 2006; 45:8209-8217. Descriptions of mathematical formalisms for holographic image reconstruction taught in the abovementioned publications are incorporated herein by reference. A reconstruction algorithm of the present invention includes, in relevant part, filtering an interferogram (associated with light 124 scattered by a tissue layer at particular depth of the tissue sample 130) in Fourier domain to at least eliminate the unwanted zero-order diffraction and conjugate images, thereby forming a filtered interferogram. Because an interferogram can be considered a diffraction grating (as far as a wavefront incident onto the interferogram in concerned), a product of the filtered interferogram and the complex amplitude of the light-beam in the reference arm of the interferometer (such as the embodiment 100) is formed from which the 2D image is extracted, under the Fresnel diffraction approximation. A sequence of time-varying 2D images corresponding to tissue layers located at different tissue sample depths are stitched together to form a time-varying 3D-image array containing optical data that represent both microstructural and speckle information about the tissue sample 130.

In one instance, for example, the time-varying viscoelastic modulus characteristic is derived for each value of optical delay (established by the appropriate alignment of the reference arm of the interferometer of FIG. 1B) based on the acquired optical data representing irradiance fluctuations across the registered laser speckle field, from a speckle intensity decorrelation function $g_2(t)$ that characterizes the rate of speckle intensity fluctuations and is empirically expressed, in terms of the MSD $\langle \Delta r^2(t) \rangle$ of light-scattering particles, as:

$$g_2(t) = \beta^2 \exp\left(-2\gamma\sqrt{k^2\langle\Delta r^2(t)\rangle + \frac{3\mu_a}{\mu_s(1-g)}}\right) + 1 == \quad (1)$$

$$\beta^2 \exp\left(-2\gamma\sqrt{k^2 r_0^2(1-e^{-t/\tau_D})} + \frac{3\mu_a}{\mu_s(1-g)}\right) + 1$$

where k is the wave number in the blood sample, $\gamma$ is an experimental parameter related to the size(s) of scattering particle(s) of the tissue sample and polarization state of light, $\beta$ is a parameter corresponding to the degree of coherence of light detected after being scattered by the tissue sample, and $$\frac{3\mu_a}{\mu_s(1-g)}$$

defines the optical properties of the sample (via $\mu_a$, which relates to an absorption coefficient of the tissue sample, and $\mu_s$, which relates to the scattering coefficient of the tissue sample).

In order to experimentally determine the $g_2(t)$ value corresponding to optical irradiance detected at a particular pixel of the detector 140, the normalized cross-correlation (NCC) of a chosen 3D array of data is computed in the Fourier domain. The maximum NCC value corresponding to that particular pixel is then determined, and $g_2(t)$ is defined by averaging several cross-correlation functions that evolve in time, Optionally, to account for the contribution of static time-independent component of irradiance of light scattered by the sample, the averaged $g_2(t)$ value is normalized by the time-averaged irradiance.

An embodiment of the algorithm further includes determination of the viscoelastic modulus from the MSD data, for each pixel. For the specific model of Eq. (1), for example, $G^*(\omega)$ is determined with the use of a modified algebraic form of the generalized Stokes-Einstein equation that directly relates the MSD of particles in motion to the frequency-dependent bulk viscoelastic modulus $G^*(\omega)$, of the material, via $$|G^*(\omega)| = \frac{kT}{\pi a \langle \Delta r^2(1/\omega)\rangle \Gamma(1+\alpha(\omega))} \Big|_{t=1/\omega} \quad (2)$$

where a is the characteristic size of a scattering particle, $\tau$ is the gamma function, and $\langle \Delta r^2(1/\omega)\rangle$ is the magnitude of the MSD at $t=1/\omega$. The value of $\alpha(\omega)$ is given by $$\alpha(\omega) = \frac{d\ln\langle\Delta r^2(t)\rangle}{d\ln(t)}\Big|_{t=1/\omega} \quad (3)$$

In order to determine a 3D distribution of micromechanical properties of the tissue sample, at each pixel the speckle intensity decorrelation, $g_2(t)$, is calculated from the coherence-gated normalized cross-correlation in three-dimensions between the 3D image matrix measured using the interferometric system at time $t=t_0$, with each subsequent time-varying 3D image matrix measured at times $t_i>t_0$. At each pixel, the magnitude of $G^*(\omega)$ is measured using empirical methods described above. The resulting 3D array of discrete $|G^*(\omega)|$ values for each frequency $\omega$ is further processed using spatial filtering and image interpolation techniques to form 3D parameter maps representing a volumetric distribution of tissue sample viscoelasticity.

Optionally, this 3D distribution of the stiffness characteristic of cellular microenvironment is further mapped or transformed into visually perceivable images (such as color-maps, for example) that demonstrate to the user viscoelastic behavior of the tissue sample on cellular level. Accordingly, 3D maps of micromechanical and microstructural characteristics of the tissue sample and corresponding 3D maps of frequency-modulated $G^*(\omega)$ are optionally displayed at a display 146. Contrast of the created color-maps is indicative of micromechanical differences between portions of the mapped tissue.

Figure 2A:
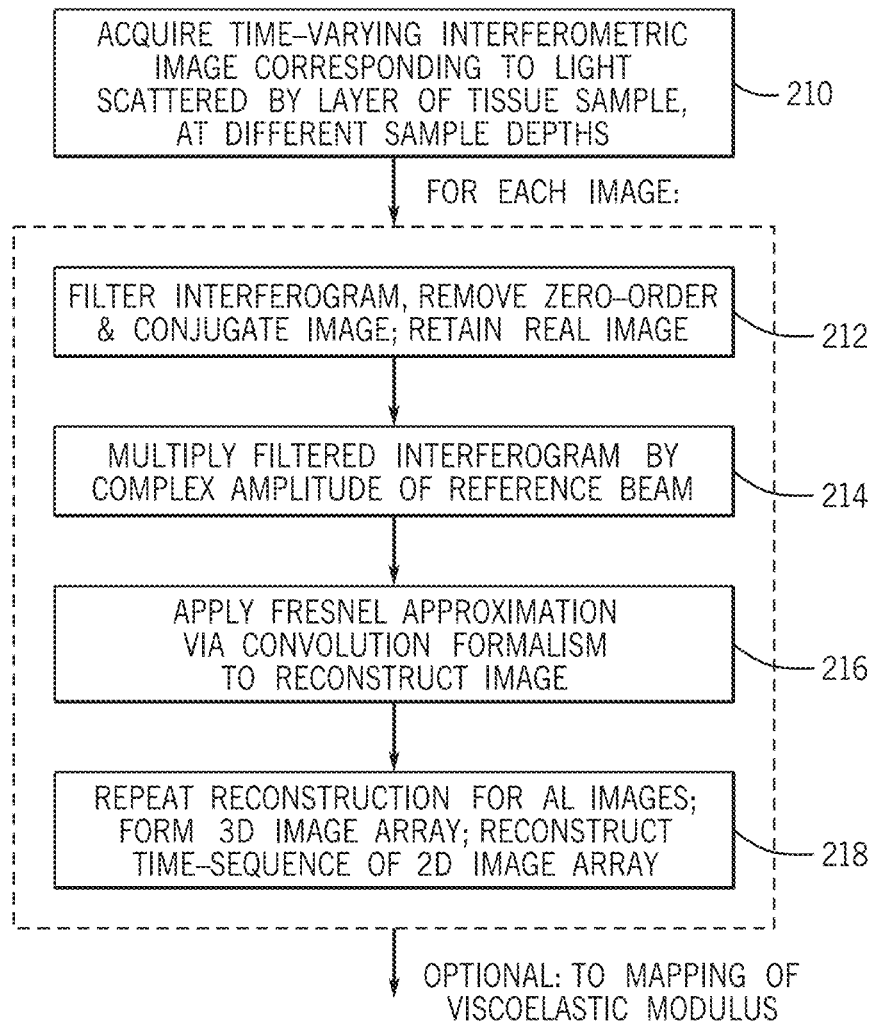
FIG. 2A is a flow-chart illustrating an embodiment of the algorithm for reconstruction of an interferogram for use with an embodiment of the invention.
Figure 2B:
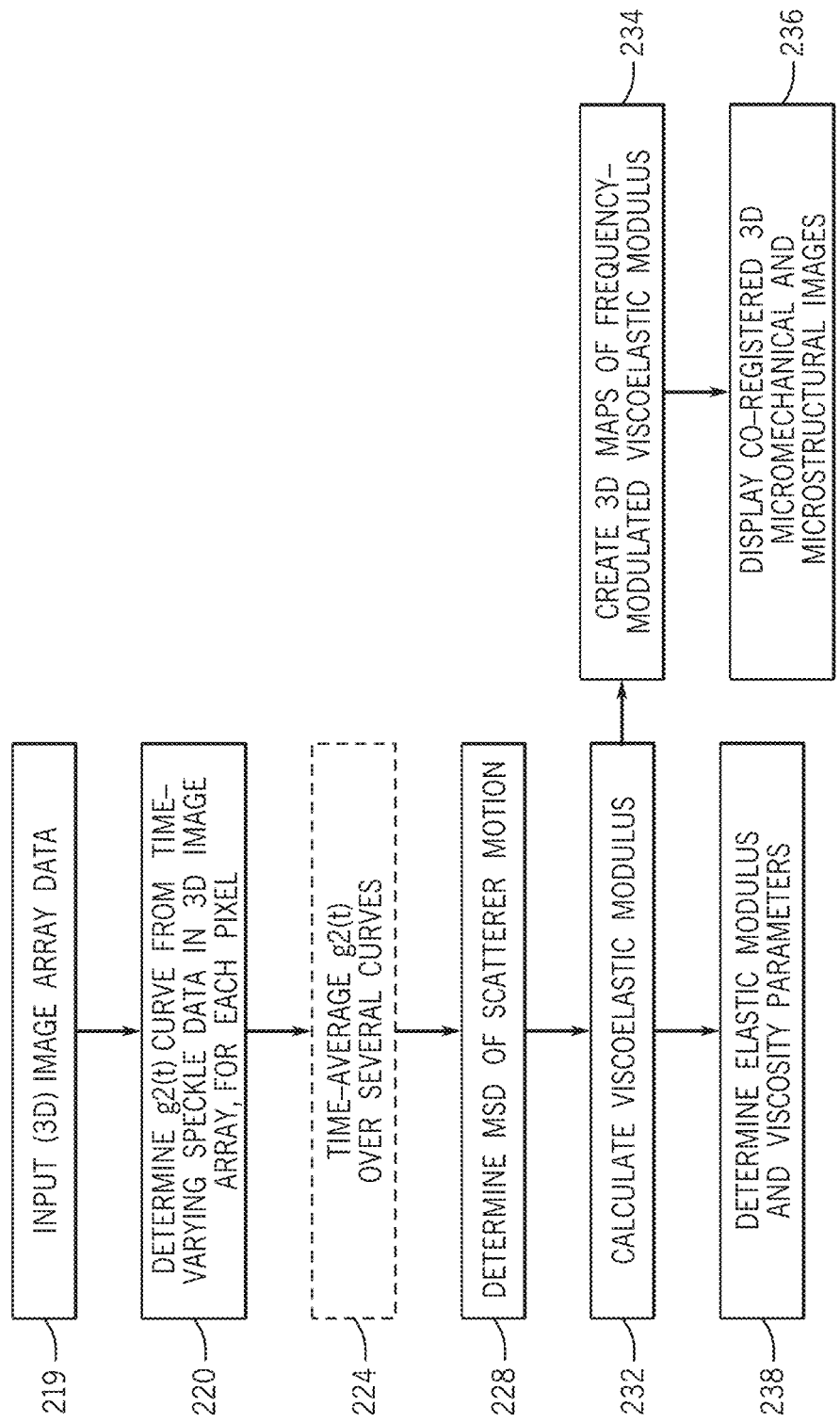
FIG. 2B is a flow-chart illustrating an embodiment of the algorithm for mapping of three-dimensional (3D) distribution of a viscoelastic modulus, of a tissue sample, acquired with the use of an embodiment of the invention, displayed in FIG. 1B.

FIGS. 2A and 2B offer flow-charts that respectively represent embodiments of a method of the invention related to a hologram reconstruction and 3D viscoelastic modulus mapping. Here, major steps of data-processing algorithms of the invention are depicted. In reference to FIG. 2A, for example, at step 210 optical data representing a time-varying interferometric image corresponding to light scattered by a tissue layer that is defined by the instantaneous optical parameters of the employed interferometer and the coherence length of light used for imaging. The acquired optical data is further processed, for example with a computer processor, to spatially filter the interferogram, at step 212, to determine a product the spatially-filtered interferogram with a complex amplitude of the reference beam, at step 214, and to reconstruct the interferometric image at step 216. Such data processing is repeated for each of the interferometric 2D data sets that are further grouped into a 3D data set associating the 2D data sets with respectively corresponding depths of the biological tissue at which tissue layers are located, 218. After, the algorithm may proceed further to mapping of the viscoelastic modulus parameter. In accordance with the flow-chart of FIG. 2B, the 3D interferometric data array is received by the processor at step 219. From the received 3D data array, the decorrelation curves are determined for each pixel of the detector at step 220 and corresponding time-averages values of decorrelation distributions are calculated at step 224. At step 228, the MSD of motion of scatterers of the tissue sample are determined, followed by the calculation of the viscoelastic modulus at step 232. The obtained values of the viscoelastic modulus are optionally mapped into 3D arrays, at step 234, and further displayed, at step 236, as visually-perceivable volumetric representations to the user, optionally together with 3D images of micromechanical characteristics of the tissue sample. Alternatively or in addition, the volumetric elastic modulus and viscosity parameters are determined from the viscoelastic modulus at step 238.

Target operation characteristics of an embodiment of the invention such as the embodiment 100 of FIG. 1 are summarized in Table 1.

Figure 3A:
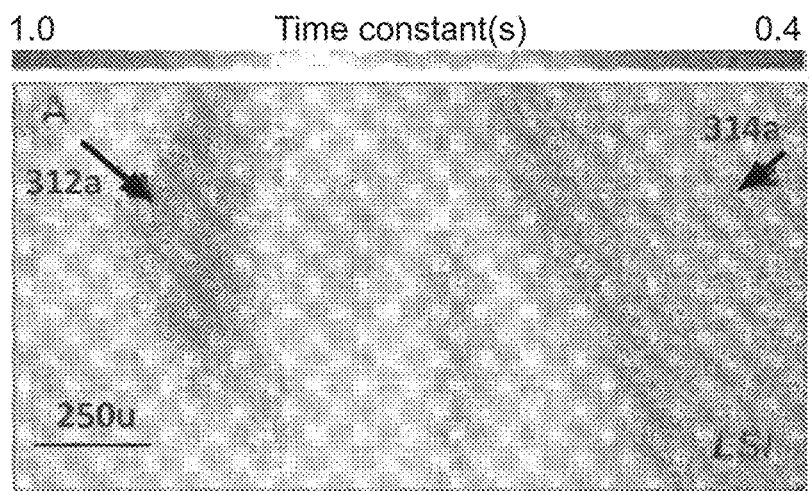
FIGS. 3A, 3B, and 3C are images of a specific tissue sample acquired with the use of three different imaging modalities, and correspondence between identified related portions of these images.
Figure 3B:
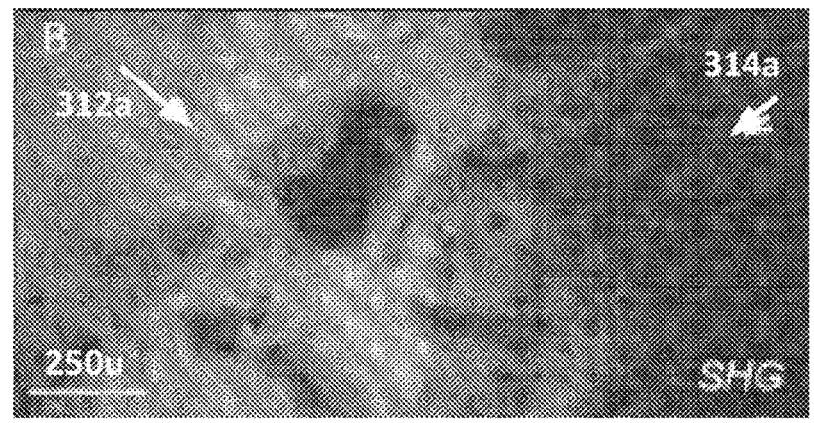
Figure 3C:

FIGS. 3A, 3B, and 3C provide co-registered images of a human breast tissue with cancer (carcinoma in situ) acquired with bright-field microscopy (FIG. 3C), with the use of second-harmonic frequency imaging, (FIG. 3B), and a color-map of viscoelasticity of the breast tumor tissue obtained with LS-imaging (FIG. 3A). Regions of stiffness, observable in FIG. 3A in red and indicated with an arrow 310a, correlate with the presence of collagen networks in the image of FIG. 3B and indicated with an arrow 314a. Blue regions (indicating low viscosity tissue) of FIG. 3A marked with and arrow 310b are corroborated by imaging of fat-droplets present in the area 314b of FIG. 3C.

Figure 4C:
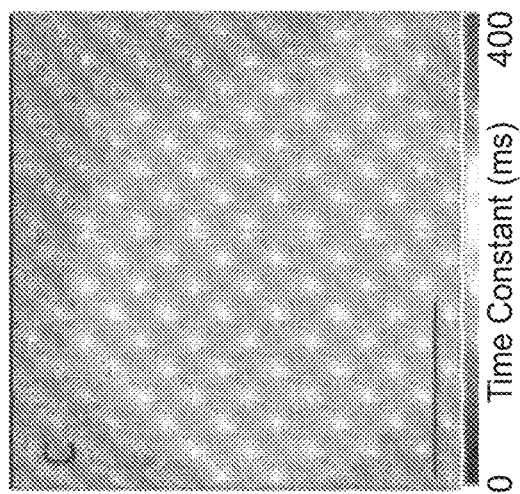
FIGS. 4A, 4B, and 4C are images of a 3D ovarian cancer nodule.
Figure 4B:
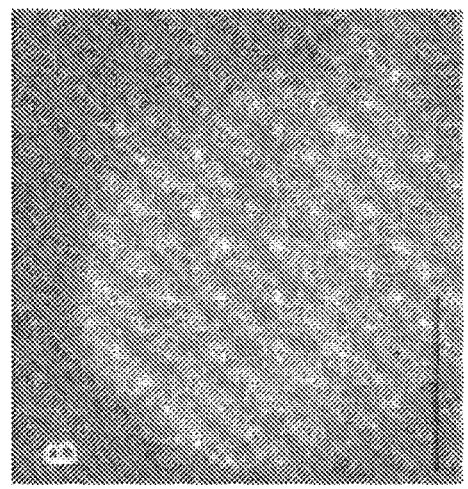
Figure 4A:
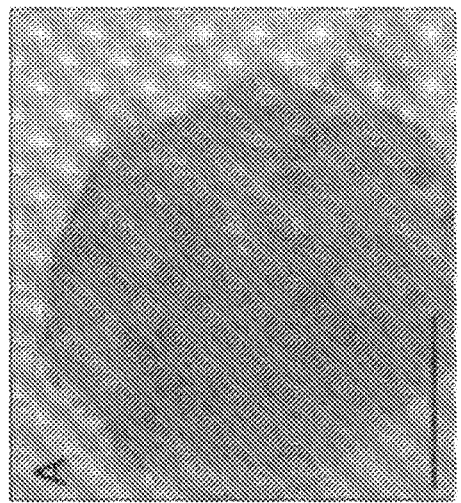

FIGS. 4A, 4B, and 4C illustrate feasibility of laser-speckle based analysis for micromechanical evaluation of 3D ovarian cancer model. FIG. 4A presents a bright-field microscopy image of a multicellular 3D ovarian cancer nodule, while FIG. 4B provides a corresponding a snap-shot image of a corresponding laser speckle pattern. FIG. 4C is a reconstructed color-map showing that the cancer nodule is significantly stiffer than the surrounding ECM, thereby demonstrating that the proposed system and method for evaluation of biological tissue possess sufficient measurement sensitivity.

TABLE 1

| Operational Characteristic | (Range of) Value(s) |
| --- | --- |
| Spatial Resolution | ~1 um (axial), ~2 um (lateral, transverse) |
| Measurement Depth | ~300 um |
| Field of View (FOV) | ~300 um |
| Working distance | 10 mm |
| Data Storage Rate | ~500 MB/sec |
| Range of Measured G* | about 0.001 Pa to about 1 kPa |
| Accuracy | Correlation: R > 0.7, p < 0.05; deviation of HLSM data from that of mechanical microrheometer not to exceed 10% |
| Range of Frequency ω | about 0.01 KHz to about 1 kHz |
| Frame Rate | ~1 kHz |
| Imaging time per frame | Sample dependent (for example, ~1 to 2 s for softer samples of <10 kPa; ~10 s for firmer sample of ~10 kPa) |
| Sensitivity (an measurable increment of G*) | about 0.001 Pa |
| Reproducibility | about 90% or higher |

It is appreciated that, in further reference to FIG. 1B, the data acquisition and processing system 144 optionally includes a processor controlled by instructions stored in a memory and programmed to at least store the optical data, analyze the interferograms, carry out the calculation of viscoelastic characteristics of the tissue sample and the determination of the stiffness parameters and their time-evolution based on such viscoelastic characteristics, as well as effectuate creating of color-coded maps of stiffness microstructure as discussed above. In addition, while the invention may be embodied in software, the functions and algorithms necessary to implement the invention may optionally or alternatively be embodied in part or in whole using firmware and/or hardware components known in the art.

Laser speckle micro-rheology (LSM) is a novel optical approach capable of non-contact, non-destructive, micromechanical analysis of tissue. LSM enables evaluating the depth-integrated spatially-varying shear viscoelastic modulus, $G^*(x,y,\omega)$, across the specimen with unprecedented resolution and unparalleled speed compared to currently available mechanical testing devices such as the mechanical rheometer and AFM-based indentation. In an LSM instrument, the specimen, such as, for instance, the tissue, the cell culture system, or the embryonic entity, is illuminated with a coherent collimated beam of light. Alternatively, an expanded beam may be used to illuminate the sample.

For instance, the beam may be directed towards the sample as follows. A non-polarized He—Ne laser beam may be coupled into a single mode optical fiber (SMF). The output of the SMF may be collimated using a fiber coupler. It can then be linearly polarized and passed through a beam expander and focused by a lens at the back focal plane an infinity-corrected objective lens. This creates a collimated beam at the front of the objective. The specimen is placed on a motorized x-y stage, mounted on a manual precision z-stage beneath the objective. The z-stage is manually adjusted such that the specimen luminal surface is leveled at the front focal plane of the objective. This can be verified by acquiring bright field images using white light illumination. The use of an infinity-corrected objective lens allows for placement of a beam splitter between the objective lens and the tube lens. The beam splitter bends the illumination beam and redirects it towards the sample. It may also be used to facilitate a multi-modal microscopy system that combines LSM with, for example, second harmonic generation microscopy and/or fluorescent microscopy.

In exemplary implementations of LSR, a coherent laser beam illuminates the sample and light rays are scattered multiple times by endogenous particles within the specimen. In other words, once the specimen is illuminated, light rays interact with intrinsic light scattering particles across the illuminated volume before being absorbed, transmitted through, or back-scattered. A high-speed CMOS camera, for example, then collects the back-scattered light. The back-scattered light rays pass through the same objective lens. A tube lens can then be used to form an image at the, for example, CMOS or CCD sensor of a high-speed sensitive camera. Alternatively, the light rays may be collected in transmission geometry. The detector may also be replaced by an array of photo-diodes. Since light rays travel along paths of different lengths, they possess different optical phases when they impinge on the CMOS sensor. Consequently, their contractive and destructive interference can create a grainy, fluctuating intensity pattern of dark and bright spots, known as the speckle pattern, with each dark or bright spot referred to as a speckle spot. Speckle fluctuations are highly sensitive to Brownian displacements of scattering particles, in turn influenced by the viscoelastic susceptibility of the surrounding medium and the microenvironment, and are analyzed via the speckle intensity autocorrelation curve, $g_2(t)$.

For example, cross-correlation analysis of speckle frames may be used to yield the speckle intensity autocorrelation function, $g_2(t)$. An exemplary LSR approach for providing an index of tissue viscoelasticity in situ involves measuring the time constant of laser speckle intensity fluctuations. In other words, by fitting an exponential curve to $g_2(t)$, and calculating the speckle decorrelation time constant, $\tau$, the rate of speckle fluctuations can be quantified. In compliant samples, intrinsic particles undergo extensive Brownian excursions and frequently modify the trajectories of photons scattered from the sample to induce rapidly fluctuating speckle patterns. Rigid substrates, on the other hand, restrict Brownian movements and elicit only minute speckle modulations. We have previously demonstrated that speckle decorrelation time constant, $\tau$, exhibits a strong, statistically significant correlation with $G^*(\omega)$ over a wide range of moduli for both phantoms (r=0.79, p<10', G*: 320 mPa to 10 kPa) and tissues (r=0.88, p<10', G*: 60 mPa to 600 kPa). Moreover, we have established that LSM successfully extracts the $G^*(\omega)$ from speckle fluctuations in a number of soft viscoelastic materials and biological fluids.

As previously discussed, LSR and other micro-rheology studies have shown that $G^*(\omega)$ can be successfully extracted by measuring the mean square displacements (MSD) of Brownian particles in soft homogeneous materials of low viscoelastic moduli such as colloids, gels, polymer solutions, and bio-fluids with known optical properties. These prior studies have been limited to highly compliant or soft materials with viscoelastic moduli below a few kilopascals. We have recently proposed a processing scheme to accurately deduce $G^*(\omega)$ from the $g_2(t)$. In this scheme, temporally resolved and temporally averaged analyses of speckle frame series return the mean square displacements (MSD) of scattering particles and their average sphere-equivalent radius a. The generalized Stokes-Einstein relation (GSER) is then used to extract the $G^*(\omega)$ as:

$$G^*(\omega) = \frac{K_B T}{\pi a \langle \Delta r^2(1/\omega) \rangle \Gamma(1 + \alpha(1/\omega))} \bigg|_{t=1/\omega} \quad (4)$$

Here, $K_B$ is the Boltzman constant, T is the temperature (in Kelvins), $\alpha$ is the log-log slope of MSD at $t=1/\omega$, and $\Gamma$ is the gamma function. The standard Stokes-Einstein equation relates the diffusion coefficient of spherical particles in a simple Newtonian fluid to its viscosity. The GSER has been initially proposed as an ad-hoc extension of the standard equation, relating the mean-square displacements of particles in a viscoelastic media to $G^*(\omega)$, but it later found firmer theoretical grounds. Despite its major utility, GSER has been primarily used for rheological studies of soft emulsions, colloidal suspensions, gels, and polymer solutions of relatively low moduli, with strong viscous component.

Laser Speckle Rheology (LSM) for Evaluating the Viscoelastic Properties of Hydrogel Scaffolds: In line with and further to the above discussion, LSM experiments for evaluation of viscoelastic properties of hydrogel scaffolds will now be discussed. Natural and synthetic hydrogel scaffolds exhibit distinct viscoelastic properties at various length scales and deformation rates. LSM offers a non-contact optical approach for evaluating the frequency-dependent viscoelastic properties of hydrogels. As discussed above, in LSM, a coherent laser beam may be used to illuminate a specimen, and a high-speed camera may be used to acquire the time-varying speckle images. Cross-correlation analysis of frames returns the speckle intensity autocorrelation function, $g_2(t)$, from which the frequency-dependent viscoelastic modulus, $G^*(\omega)$, is deduced. As will be further discussed, the capability of LSM for evaluating the viscoelastic properties of hydrogels over a large range of moduli, using conventional mechanical rheometry and atomic force microscopy (AFM)-based indentation as reference-standards, has been demonstrated. Results demonstrate a strong correlation between $|G^*(\omega)|$ values measured by LSR and mechanical rheometry (r=0.95, p<$10^{-9}$), and z-test analysis reports that moduli values measured by the two methods are substantially identical (p>0.08) over a large range (47 Pa to 36 kPa). In addition, $|G^*(\omega)|$ values measured by LSR correlate well with indentation moduli, E, reported by AFM (r=0.92, p<$10^{-7}$). Further, spatially-resolved moduli measurements in micro-patterned substrates demonstrate that LSR combines the strengths of conventional rheology and micro-indentation in assessing hydrogel viscoelastic properties at multiple frequencies and small length-scales.

As mentioned above, biomaterials and hydrogels are increasingly used in tissue engineering, regenerative medicine, drug-delivery, and mechanobiology research owing to their unique biocompatibility, tunable compliance, deformability and stress resilience. To fully integrate into biological systems, these biomimetic scaffolds exhibit distinct mechanical properties, similar to natural tissues at potential sites of implantation. Due to their large water content, tissues and hydrogels are viscoelastic, exhibiting both solid-like and liquid-like traits at different deformation rates and length-scales. This complex mechanical behavior is best defined by the frequency-dependent shear viscoelastic modulus discussed above (i.e., $G^*(\omega)=G'(\omega)+iG''(\omega)$). Here $G'(\omega)$ and $G''(\omega)$ are the elastic and viscous moduli, representing the solid-like and fluid-like features respectively, and $\omega$ is the deformation frequency. The macro-scale viscoelastic properties of tissues and biomimetic scaffolds enables them to withstand physiological and hemodynamic loads, yet exhibit sufficient flexibility. The micro-scale properties, on the other hand, influence the mechanical support provided to cells, impart mechanical cues to direct cellular growth and differentiation, control the diffusion of oxygen and nutrients, and regulate the release of bio-molecules and drugs. Thus, there is a need to quantify the viscoelastic properties of tissue scaffolds and biomimetic gels in their native state at multiple length-scales and deformation frequencies in a non-destructive fashion without contact or sample manipulation.

Therefore, here, we investigate, validate, and demonstrate the extended dynamic range of LSM measurements in viscoelastic gel substrates exhibiting a wide range of $G^*(\omega)$, compared to previous studies, similar to normal and pathological tissues as well as synthetic and engineered tissue scaffoldings and biomaterials. Using conventional mechanical rheometry and AFM as commercially available standards, we further investigate the ability of LSM approach for evaluation of gels with biologically relevant viscoelastic properties at both bulk and micro-scales. In addition, we demonstrate the utility of LSM for micromechanical mapping of phantom constructs and biological tissue. To this end, we first prepare homogeneous agarose, polyacrylamide (PA), and polyethylene glycol di-acrylate (PEGDA) hydrogels with varied optical properties and scattering particle size distributions, spanning a large range of moduli (47 Pa-36 kPa), pertinent to natural and synthetic tissues. Despite the large water content within low density polymer network, these hydrogels are markedly more viscoelastic than primarily viscous silicone colloids, lipid emulsions, and hydrophobic silicone-based PDMS polymers, previously evaluated by LSM.

Below, the LSR framework will be detailed and validated for quantifying the frequency-dependent viscoelastic behavior of hydrogels exhibiting an extended range of viscoelastic moduli significantly larger than prior studies.

LSR measurements of the frequency-dependent $G^*(\omega)$ curves of the hydrogels are compared with the results of rotational rheometry, the conventional standard for evaluating the bulk $G^*(\omega)$. While mechanical rheometry provides information on the viscoelastic behavior of a sample at multiple oscillation frequencies, it fails to assess the local viscoelastic heterogeneities at the microscale. The commercially available standard for probing the local mechanical properties at small scales is the AFM-based indentation. Nonetheless, the indentation modulus, E, evaluated by AFM, represents solely the elastic behavior at a single indentation rate, and does not fully reflect the frequency-dependent viscoelasticity needed for characterizing viscoelastic hydrogel and biomimetic scaffolds. The LSR approach described here aims to bridge the strengths of both of the above conventional techniques by providing frequency-dependent measurements of viscoelastic moduli $G^*(\omega)$ akin to mechanical rheometry yet with high spatial resolution similar to AFM. To fully examine the capacity of LSM for evaluating the frequency-dependent $|G^*(\omega)|$ at micro-scale, we also fabricate composite PDMS-PEGDA substrates, exhibiting micro-patterned features of distinct viscoelastic properties. Spatially-resolved 2D maps of $|G^*(\omega)|$ across the micro-patterned substrates are evaluated by LSM and compared to the conventional rheology measurements of the PDMS and PEGDA components. The results detailed below establish that LSR encompasses the desired traits of both conventional rheology and micro-indentation techniques, and evaluates the $|G^*(\omega)|$, at multiple frequencies and length-scales, without requiring sample contact or manipulation.

Homogeneous viscoelastic hydrogel preparation and casting: To test the capability of LSM in evaluating shear moduli of viscoelastic gels, three sets of gels were prepared, composed of different constituent materials that covered a wide range of viscoelastic properties pertinent to mechanical properties of normal and pathological tissues, as well as synthetic and engineered tissue scaffolds, and biomaterials. Each set contained 6 gels, with shear moduli covering the dynamic range of interest.

Agarose gels were prepared at concentrations of 0.5%, 1%, 1.5%, 2%, 2.5%, and 3%. For each gel, 9 ml of deionized water was transferred to a 100 ml beaker, containing a magnetic stirring bead. Low gelling point agarose powder (Sigma-Aldrich Co. LLC., St. Louis Mo., USA) was weighed (100 mg per 1% gel) using a precision scale. The powder was slowly sprinkled into the beaker, while stirring at 500 rpm to avoid clumping. The beaker weight prior to heating was recorded. The beaker was covered by a petri dish lid and the solution was brought to boil using the hot plate. It was left to boil, stirring continuously until no particulate agarose was visible and the solution appeared transparent. Hot deionized water was used to return the beaker to initial weight and to maintain the initial weights of solutions. Finally, 1 ml intra-lipid solution (1% final volume) was added to the beaker, while stirring. The precursor solution was poured into a 35 mm diameter Petri dish and left at room temperature until fully cured. Alternatively, the petri dish could be placed on ice to reduce the curing time to a few minutes. The shear moduli of agarose gels grow with concentration covering the range of $G^*$: 162 Pa to 28 kPa at $\omega=1$ Hz.

Polyethylene glycol de-acrylate (PEGDA) gels of 6%, 8%, 9%, 10%, 12%, and 15%, were fabricating by creating a 9 ml solution of diluted PEGDA solution (Sigma-Aldrich, molecular weight: Mn 575) in phosphate buffer saline (PBS) at the corresponding concentrations. Solutions were completed with 1 ml of intralipid and 1% w/v of photo-initiator (DAROCUR 1173, Ciba Specialty Chemical, Switzerland). About 200 µl of precursor solutions was pipetted into an imaging chamber with a cylindrical opening to house the solution (diameter of 9 mm, depth of 2 mm) and a transparent polycarbonate optical window for LSR measurements. The chamber was placed within 1 cm of a high power UV curing LED system (beam diameter 12 mm, $\lambda=365$ nm, 175 mW/cm$^2$, Thorlabs, N.J.) and illuminated for 3 minutes. Despite close proximity UV LED and the chamber, the Gaussian beam profile created a stiffness gradient across the sample, with central areas being slightly more elastic than peripheral regions, as confirmed by LSR and AFM-based indentation. The shear moduli of PEGDA gels is proportionate to concentration covering the range of $G^*$: 1 kPa to 36 kPa at $\omega=1$ Hz.

Polyacrylamide gels of varying viscoelastic properties were prepared using 40% acrylamide and 2% N,N' methylene-bis-acrylamide stock solutions (Sigma-Aldrich Co. LLC., St. Louis Mo., USA), following well-established protocols. Briefly, the required volume fractions of acrylamide and bis-acrylamide in a 5 ml final precursor mixture were calculated based on the concentrations of available stock solutions and the desired concentration of acrylamide and bis-acrylamide in the final gels. The acrylamide and bis-acrylamide concentration pairs were as follows: (3%, 1%), (7.5%, 0.05%), (7.5%, 0.2%), (7.5%, 0.6%), (10%, 2%), and (20%, 2.5%). The precursor solutions were brought to a 5 ml final volume by adding 500 µl intralipid, 1250 µl of Tris-HCl stock buffer (pH 8.8), and an appropriate volume of deionized water. To polymerize the solution, 5 µl of tetramethylethylenediamine (TEMED) (Sigma-Aldrich Co. LLC., St. Louis Mo., USA) and 25 5 µl of 10% ammonium persulfate (APS) were added as catalyzer and initiator, respectively. The shear moduli of polyacrylamide (PA) gels grew with both acrylamide and bis-acrylamide concentrations. The shear moduli of PA gels ranged between 150 Pa-30 kPa at $\omega=1$ Hz.

Micro-Fabricated Composite PDMS-PEGDA Substrates Preparation: Established methods for creating the micro-fabricated phantom were used. A photomask, featuring bars of assorted widths (i.e. 250, 200, 150, 100, 80, 60, 50, 30, and 10 µm) was sketched in Solidworks (DS SolidWorks, MA) and printed at high resolution (CAD/Art Services, OR). To create the mold, a 5" silicon wafer was solvent-cleaned and plasma-treated to remove residues (Technics 500-II Plasma Etcher). A 400 µm-thick layer of SU8-2100 photoresist (MicroChem, MA) was spin-coated on the wafer (Headway, Tex.). To engrave the patterns, the wafer was exposed to UV through the photomask within a mask-aligner (MJB3, SUSS MicroTech, Germany), and developed. To prepare the PDMS, resin and curing agent (Sylgard® 184 silicone elastomer, Dow Corning, Belgium) were mixed in 10:1 ratio. To differentiate PDMS from PEGDA, carbon powder (430 nm diameter, Sigma Aldrich) was added in 0.5% concentration, prior to centrifugal mixing (THINKY ARE-250, Japan). The PDMS was slowly poured on the mold, degassed in a vacuum chamber, and cured for 2 hours at 60 degrees Celsius. It was then gently peeled off and cut into blocks. Protruded bars on the PDMS bonded to a glass coverslip by plasma treatment. PEGDA 5% and 10% solutions were drawn to the spacing between PDMS and glass via capillary action and cured by UV illumination. The final micro-fabricated phantoms featured stiff PDMS bars (G*=10.8±2.1 kPa at 1 Hz) in a soft PEGDA 5% (G*=275±122 Pa at 1 Hz) as well as moderately stiff PEGDA 10% (G*=6.5±1.5 kPa at 1 Hz) backgrounds.

Human Breast Tissue Specimens: Apart from synthetic hydrogels, assorted de-identified human breast lesions with distinct diagnosis from 50 patients undergoing lumpectomy or mastectomy at Massachusetts General Hospital were collected. The specimens were kept in phosphate buffer saline (PBS) at 4 degrees Celsius briefly before testing. The samples were imaged within few hours following surgery using LSM and second harmonic generation microscopy (SHG). SHG was used to visualize the collagen fibers within tissue. Collagen is the most abundant protein macromolecule in tissue scaffolding and is the major contributor to tissue tensile strength and stiffness.

Laser Speckle Microrheology Testing: In one implementation, LSM was used to evaluate the volume-averaged viscoelastic moduli of homogeneous viscoelastic gels and the tissue specimens. The exemplary optical setup depicted in FIG. 5 can be used to capture time-varying laser speckle frame series of samples. For example, light from a randomly polarized Helium-Neon laser 505 (632 nm wavelength, 45 mW, JDSU, CA), for example, was polarized for instance by passing through a linear polarizer 510, and then expanded for example 10× (ten times) by using for example a beam expander 515. The beam was then focused by using for instance a lens 520 and its path is bent by a 50:50 beam splitter 525 and focused to a for example a 50 µm spot at the luminal surface of the sample 530 (situated on stage 535). The focused beam geometry helps ensure maximum light penetration within the sample 530 and facilitates evaluation of the diffuse reflectance profile. A high-speed camera 540, such as for instance a Basler, Ace acA2000-340 km (Germany), secured to an imaging lens 545, such as for instance a MLH-10×, (Computar, N.C.) and a linear polarizer filter 550 collects the back-scattered rays in both parallel and cross-polarized states with respect to illumination. The iris in the imaging lens adjusted the pixel to speckle ratio. The linear polarizer, in front of the imaging lens, allowed capturing speckle images at both parallel and cross polarized states. Minimized specular reflection in cross-polarized collection provides fully developed high-contrast speckle patterns exhibiting the full magnitude of intensity fluctuations. The co-polarized acquisition, on the other hand, is imperative for particle sizing. The high-speed camera 540 allows recording of the rapid speckle fluctuations elicited from soft viscoelastic materials. Data acquired by the camera 540 may be communicated to a computer 560 or dedicated processing hardware, including a processor to conduct processing and provide feedback via a display or otherwise conveyed as reports, such as will be described. Further details of the optical setup are discussed below. For example, speckle frames may be acquired at 739 fps, over an ROI of 510×510 pixels, for at least 5 seconds, and transferred to the computer via, for instance, a CameraLink interface.

Figure 7:
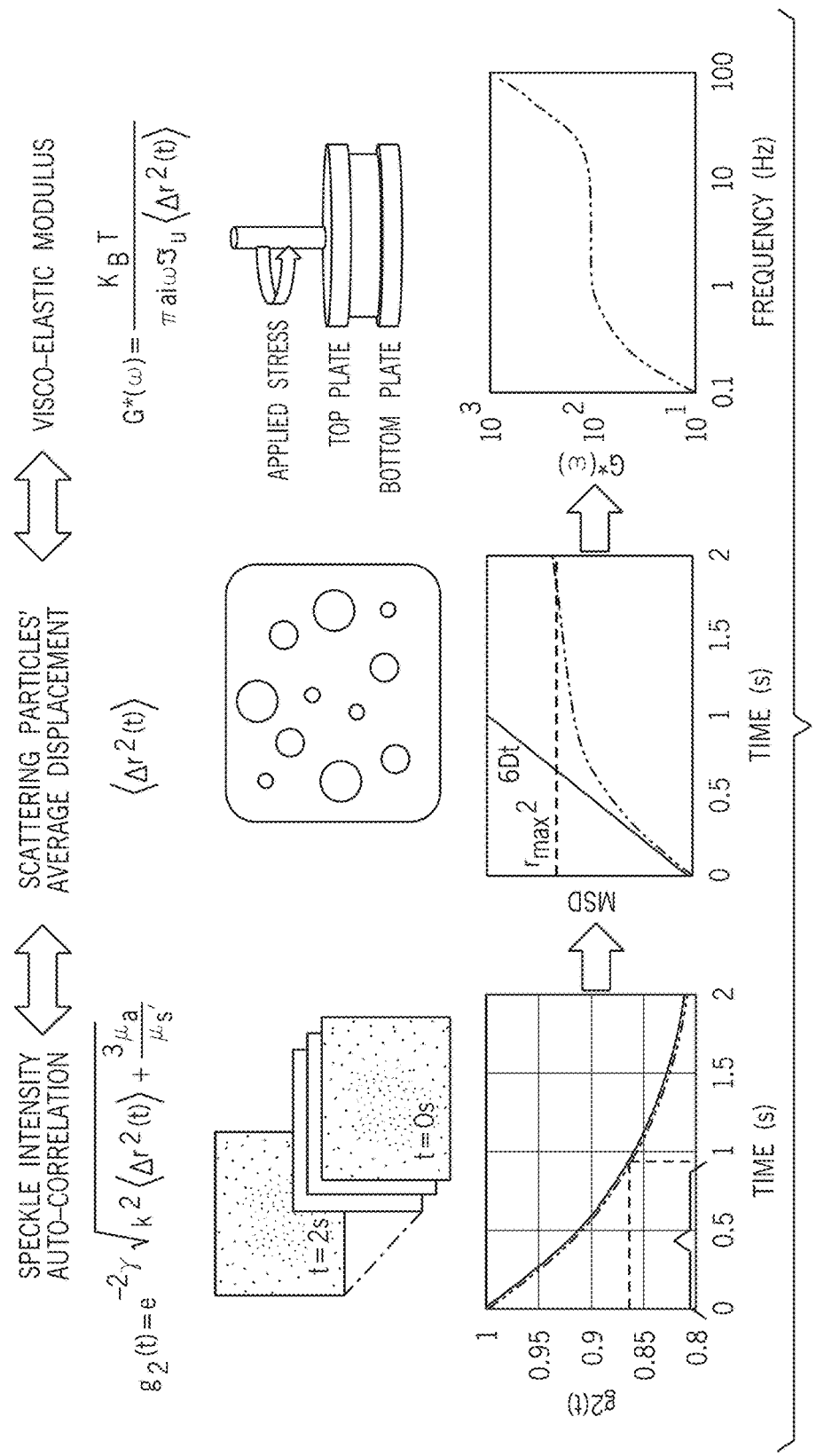
FIG. 7 represents the general operating principles corresponding with LSM.
Figure 8:
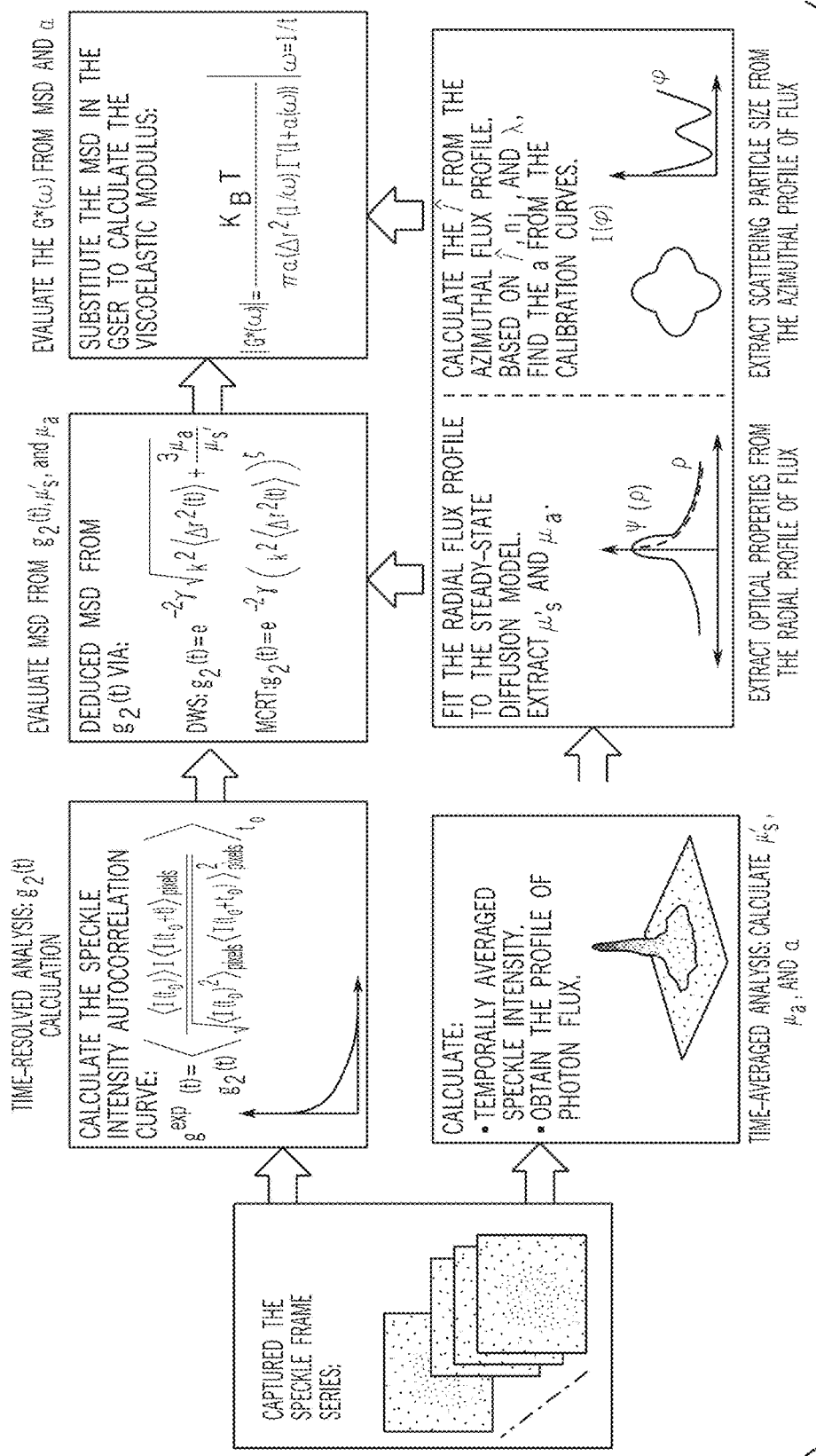
FIG. 8 provides a block diagram of an exemplary LSM processing algorithm for evaluating the volume averaged shear viscoelastic modulus, $G^*$.
Figure 22:
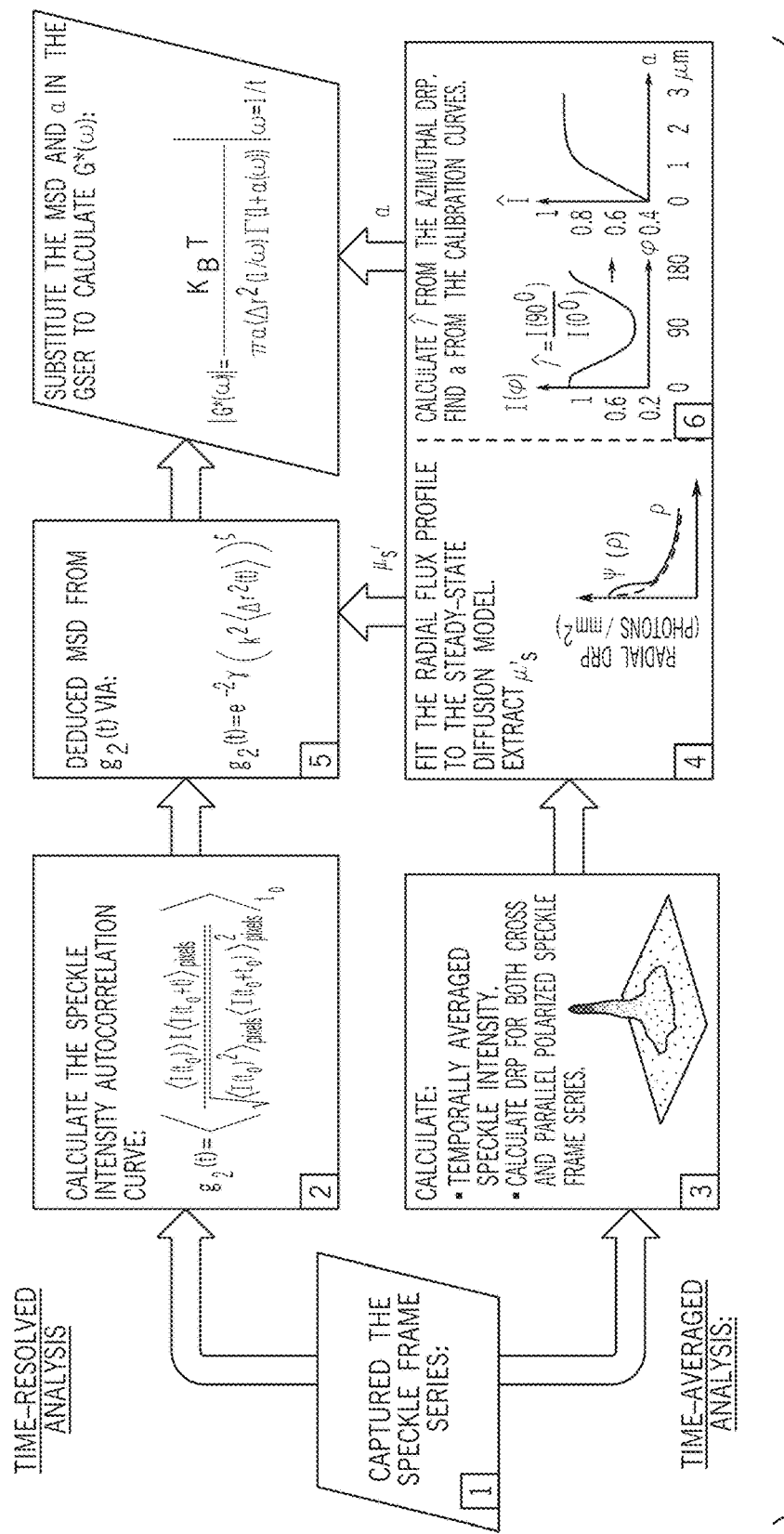
FIG. 22 provides a schematic flowchart of an exemplary LSR processing process in accordance with the present disclosure.

The LSM principles are displayed in FIG. 7. FIG. 8 represents an exemplary LSM processing algorithm suited to the setup depicted in FIG. 5. More specifically, to evaluate the G*(ω), speckle frames may be processed, for example, as outlined in the flowchart of FIG. 22. Cross-correlating the first speckle frame with subsequent frames returned the speckle intensity auto-correlation function, $g_2(t)$ (FIG. 22, box 2). Sufficient statistical accuracy can be achieved in calculating the $g_2(t)$ curves through spatial and temporal averaging over the entire frame and across multiple curves evolving in time. For example, spatial averaging over the entire ROI and temporal averaging of multiple evolving $g_2(t)$ curves may be used to achieve sufficient statistical accuracy.

In order to extract the G*(ω) from the speckle frame series, the contribution of optical properties and scattering particle size distribution to speckle fluctuations should preferably be taken into account. To evaluate the optical properties of specimens, i.e. absorption and reduced scattering coefficients ($\mu_a$ and $\mu_s'$), speckle images are temporally averaged and intensity values are converted to relative photon flux as a function of radial distance from the focus point. A model curve, derived from light diffusion approximation, is fitted to the radial diffuse reflectance profile (DRP) to calculate the optical properties. Following compensation for the influence of $\mu_a$ and $\mu_s'$ on speckle fluctuations, the mean square displacements (MSDs) of scattering particles is deduced from $g_2(t)$. For example, temporal averaging of speckle frames provides the DRP at both parallel and cross polarization states (FIG. 22, box 3). Subsequently, $\mu_s'$ is experimentally calculated by fitting a model derived from diffusion theory to the radial cross-polarized DRP (FIG. 22, Box 4). The $\mu_s'$ determines the γ and ζ parameters in the modified equation, $g_2(t)=\exp(-2\gamma (k^2<\Delta r^2(t)>)\zeta)$ used to deduce the MSD (FIG. 22, Box 5).

Next, the average radius of scattering particles, a, is obtained from the azimuth-angle dependence of DRP, acquired at parallel-polarized state, with respect to illumination. More specifically, the ratio of parallel-polarized DRP along short and long axes, i.e. $\hat{I}=I(\varphi=90°)/I(\varphi=0°)$, is compared with a calibration curve to evaluate the average radius of scattering particles, a (FIG. 22, box 6). Finally, MSD and a are substituted in GSER (Eqn. 4) to calculate the G*(ω) (FIG. 22, box 7).

Figure 6:
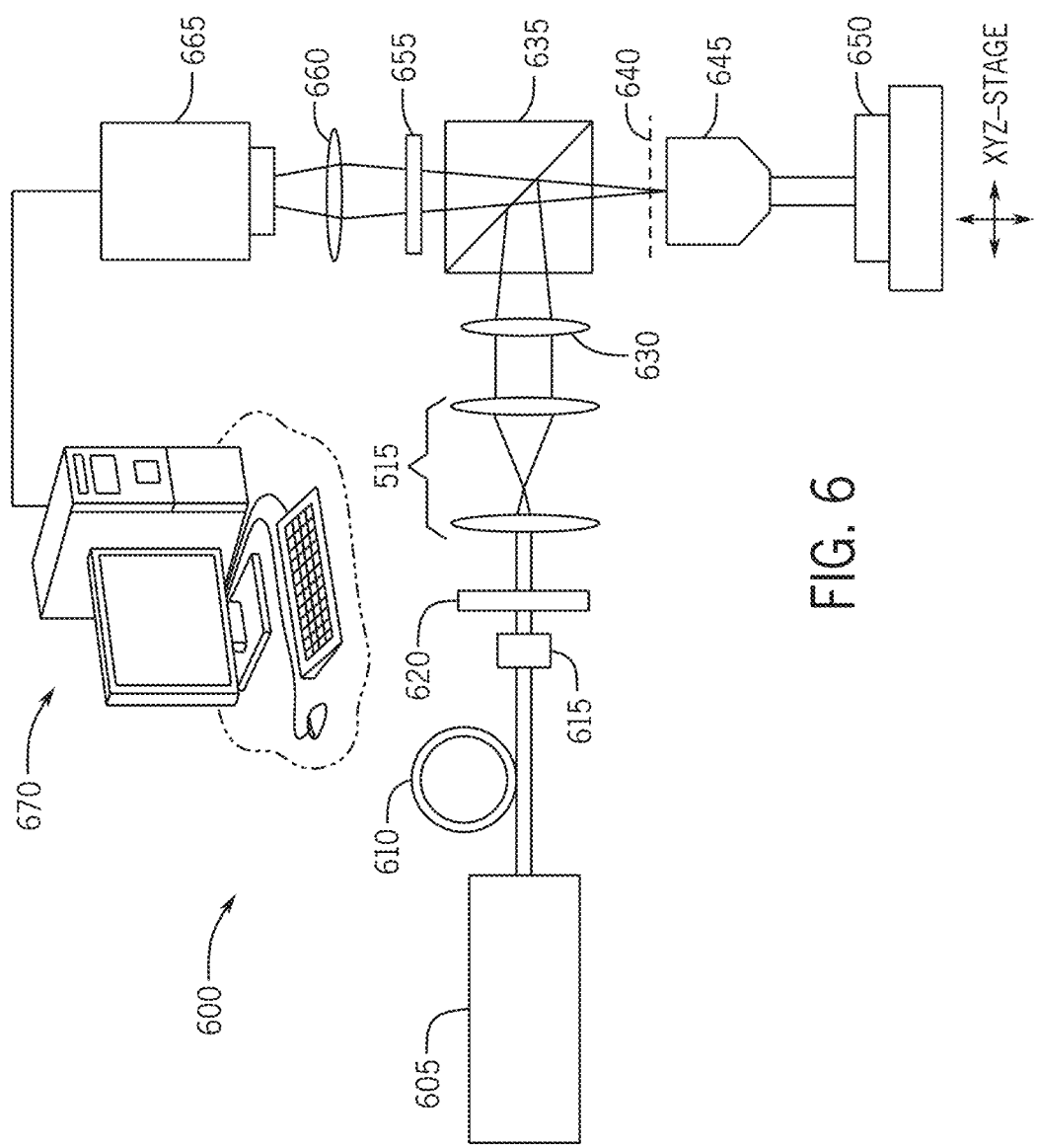
FIG. 6 is another exemplary LSM optical setup that can be used to evaluate the high resolution 2D map of $G^*(\omega)$ in micro-fabricated phantom construct and human tissue specimens.

In another embodiment, LSM is used to evaluate the high resolution 2D map of G*(ω) in micro-fabricated phantom construct and human tissue specimens. This can be accomplished using, for example, the exemplary implementation 600 depicted in FIG. 6. The beam from a randomly polarized Helium-Neon laser 605 (632 nm wavelength, 45 mW, JDSU, Milpitas, Calif., USA), for example, is coupled to a single mode fiber 610 and fiber coupler 615. The fiber output is collimated, passed through a linear polarizer 620, expanded (10×, for example) using beam expander 625, and brought to focus by a lens 630 and a 50:50 beam-splitter 635 at the back-focal plane 640 of an infinity corrected objective lens 650. The light back-scattered by the sample 650 were collected in 180 degree back-scattering geometry through the same objective 645, and was imaged by a tube lens 660 at the sensor of a high speed CMOS camera 665 (Basler, Ace acA2000-340 km, Germany). The linear polarizing filter 655, placed in front of the imaging lens aperture, enabled capturing speckle images at both parallel and cross-polarized states. An iris, embedded within the collection optics, helped ensure adjustable pixel-to-speckle ratio. Speckle fluctuations, induced by thermal Brownian displacements of scattering particles, were captured at the frame rate of at least 250 frames per second (fps). Speckle images were transferred to the computer 670 (via, for instance, a CameraLink cable).

Figure 5:
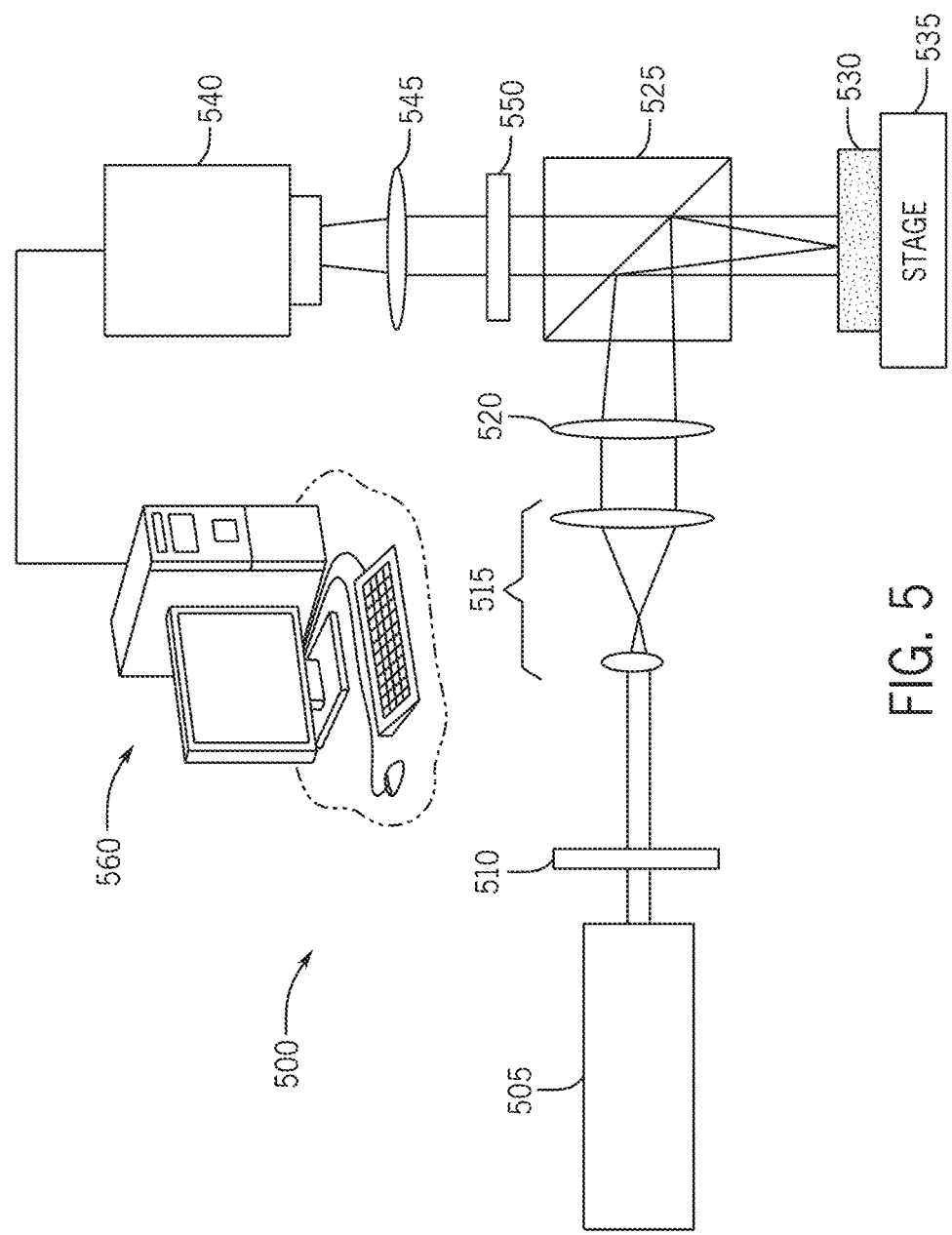
FIG. 5 is an exemplary laser speckle microrheology (LSM) optical setup that can be used to capture time-varying laser speckle frame series of samples. A randomly polarized laser beam may be directed through a linear polarizer and collimated by a beam expander. A lens and a 50:50 beam splitter can bring the beam to, e.g., a 50 μm focal spot on the sample surface. Time series of both parallel and cross-polarized, back-scattered speckle patterns can be captured by a detector (such as a CMOS camera), through a polarizing filter and an imaging lens. The iris within the imaging lens can adjust the pixel to speckle ratio.
Figure 9:
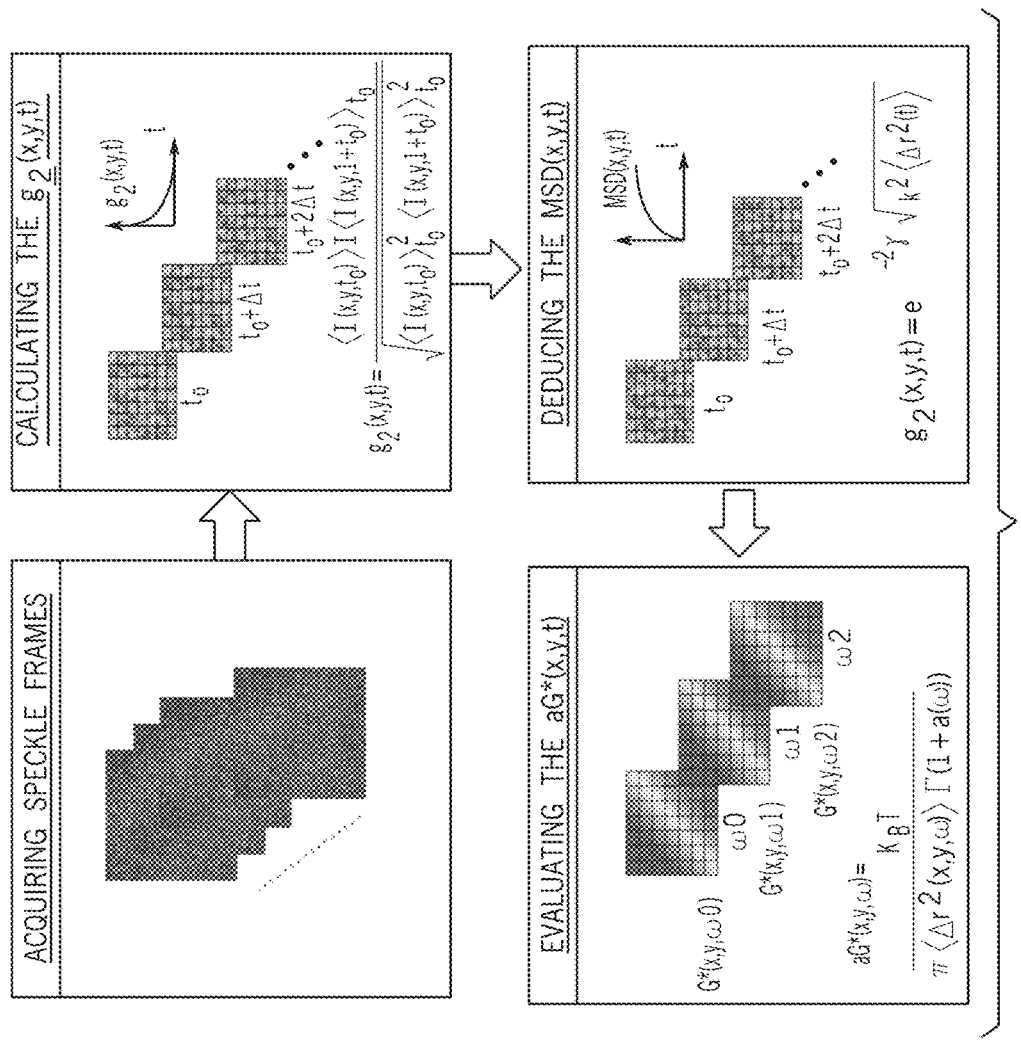
FIG. 9 depicts an exemplary LSM processing algorithm for micromechanical mapping.

Alternatively, to evaluate the spatially-resolved 2D map of G*(ω) in the micro-fabricated phantom and human tissue specimens, the focusing lens in FIG. 5 may be removed from the setup to enable expanded beam illumination. Moreover, an imaging lens may be replaced with an objective, for example a 10×, Olympus, and a tube lens, with a focal length such as 175 mm, to acquire high-resolution, magnified speckle images. The FOV may cover for example a 500×500 μm² area, corresponding to for instance 1000×1000 pixels. The phantoms and tissue may then be mounted on a translational stage and scanned at for example 450 μm steps. At each scanning location, speckle images are acquired at for instance 250 fps lasting for example 1 second. Spatially-resolved $g_2(t)$ curves for individual pixel of the frame series are obtained by limiting the spatial averaging to a for instance a 25×25 Gaussian window of neighboring pixels. As such, spatiotemporal correlation analysis of speckle frames yields the speckle intensity auto-correlation, $g_2(x,y,t) = \exp[-3.4\sqrt{(k^2 MSD(x,y,t) + 3\mu_a/\mu_s')}]$. Here MSD(x,y,t) is the mean square displacements of particles, and $\mu_a$ and $\mu_s'$ are optical absorption and reduced scattering coefficients, respectively, of tissue. Alternatively one may wish to skip correcting for the role of optical properties. In this case, conventional equation, i.e., $g_2(t) = \exp(-3.3 (k^2 <\Delta r^2(t)>)^{0.5})$, is used to deduce the MSD for individual pixels. Subsequently, spatially-resolved G*(ω) values are calculated by replacing the MSD and known a values in Eqn. 4. More specifically, the MSD(x,y,t), extracted from $g_2(x,y,t)$, is replaced in the generalized Stokes-Einstein relation to yield the depth-integrated viscoelastic modulus, $G^*(x,y,\omega) = K_B T/[j\omega a FT(MSD(x,y,t))]$, where $K_B$ is the Boltzman constant, T is temperature in Kelvins, a is particle size, ω is angular frequency, and FT is the Fourier transform. FIG. 9 represents an exemplary LSM processing algorithm suited to the setup depicted in FIG. 5.

Mechanical Rheology: The frequency-dependent viscoelastic moduli, G*(ω), of gel substrates were measured using a strain-controlled AR-G2 rheometer (TA Instruments, New Castle, Del.). To evaluate the PEGDA gels, cured using a UV illumination system within an imaging chamber, the rheometer was operated at a parallel plate geometry with a top plate diameter of 8 mm. The gels were taken out of the imaging chamber and placed at the center of the bottom plate. The top plate was lowered in 50 μm steps until it securely came to contact with the sample. This was verified by monitoring the normal force exerted on the sample. A frequency-sweep oscillation procedure was conducted, using a strain percentage of 0.1% as the control variable. The elastic, viscous, and viscoelastic moduli, i.e. G', G'', and G*, respectively, were measured over the oscillation frequency range of 0.1 to 100 Hz at 25 degrees Celsius. Similarly, for highly viscoelastic agarose and PA gels, a biopsy punch was used to cut out a cylindrical piece with 8 mm diameter out of the gels cured in 35 mm diameter petri dishes. The gels were then evaluated using the 8 mm parallel plate geometry, as described above.

Operating the rheometer at 8 mm diameter parallel plate geometry was not conducive for softer gels, i.e. Agarose 0.5%-1.5%, and PA (A3%, B1%), (A7.5%, B0.05%), and (A7.5%, B0.2%). This was because transferring the specimens from the petri dish to the rheometer bottom plate was challenging. In other words, cutting the samples to 8 mm disks were impractical. Moreover, the small contact area of this geometry obviated the possibility of probing higher frequencies, especially for softer samples. As a result, the 40 mm diameter top plate was employed and the precursor solutions for softer agarose and PA gels were directly pipetted on the rheometer bottom plate. Subsequently, the 40 mm diameter top plate was lowered until the solution was sandwiched between the two plates. Moisture traps were placed around the sample to prevent drying. Repeated frequency sweep procedures were conducted every 30 minutes and G', G'', and G*, were measured over the oscillation frequency range of 0.1 to 100 Hz at 25 degrees Celsius. The tests stopped when no further growth was observed in the evaluated moduli, indicating that the gel has fully cured.

Figure 10:
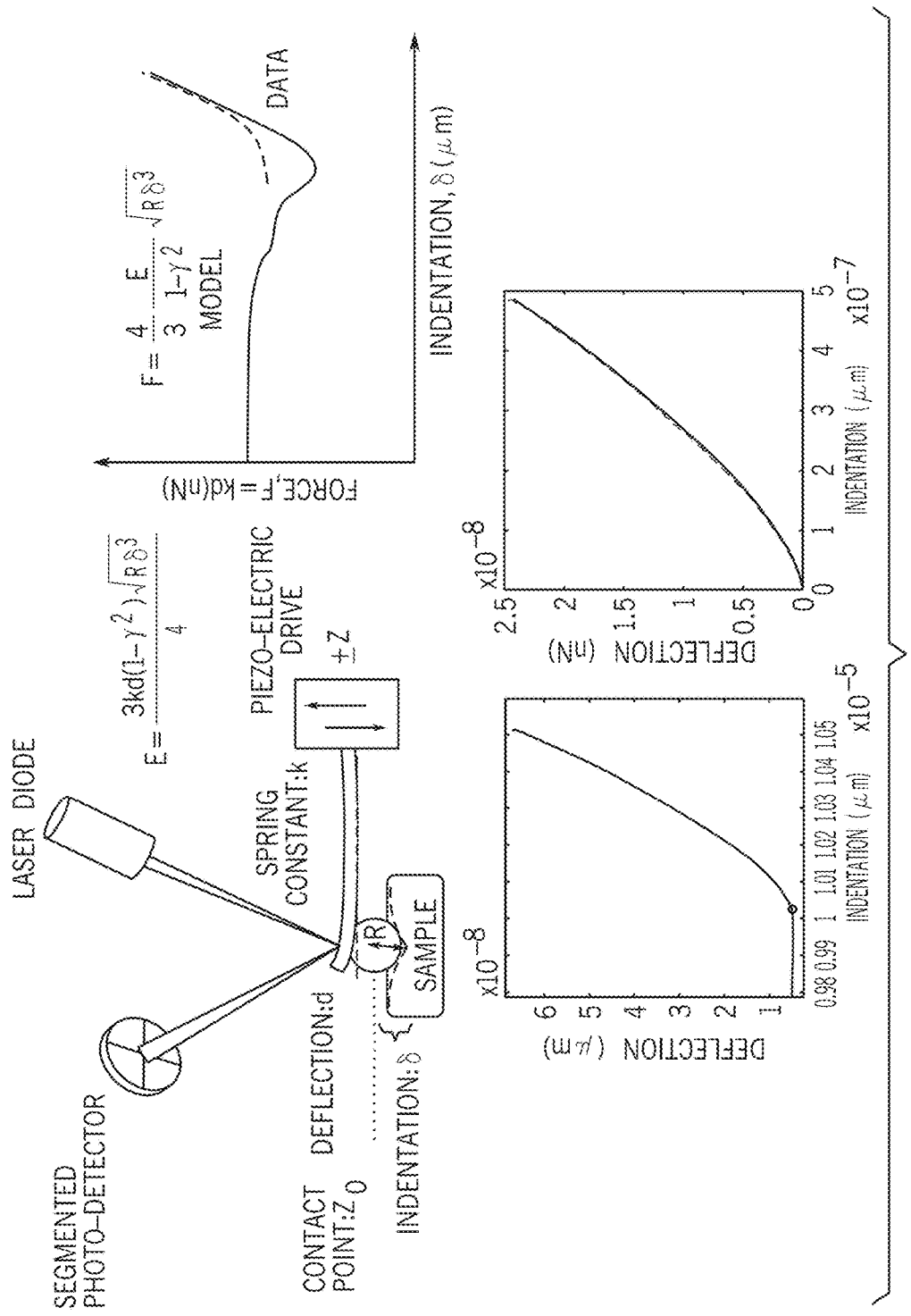
FIG. 10 depicts a typical force-displacement curve and the best-fit curve from the standard Hertz model for atomic force microscopy.

AFM-Based Micro-Indentation: The indentation moduli of hydrogels were quantified using an Asylum MFP3D atomic force microscope (Asylum Research, Santa Barbara, Calif.), mounted on an inverted optical microscope. Polystyrene colloidal beads (having a diameter of 25 μm) were glued to the tip of AFM cantilevers (Novascan, Ames, Iowa) to enable micro-scale indentation. More specifically, we used polystyrene colloidal probe tips with radius R~12.5 μm (Polysciences, PA) attached to tip-less cantilevers with nominal spring constants of k~0.12 N/m. The colloidal probes were attached to the cantilever via lift-off process. For each probe tip, the exact spring constants of the cantilevers were directly measured using thermal calibration method. The relationship between the detected voltage and the applied force was calibrated by bringing the cantilever in contact with a glass slide and calculating the slope of the voltage-displacement curve. The displacement, d, was translated to force, F, using Hooke's law (i.e., F=kd). The indentation was performed under a force control scheme, (max force ~20 nN), limiting the indentation depths to 1 μm. The tip displacement was obtained by subtracting the cantilever deflection from vertical movement of the piezoelectric stage. Each hydrogel was indented at multiple locations with three force curves acquired per location. An indentation velocity of 2 μm/s helped ensure probing the elastic modulus at lower rate, close to equilibrium condition. The Hertz model was fit to the force-displacement curve to obtain the indentation modulus, E. An indentation velocity of 2 μm/s helped ensure evaluating the indentation modulus at close to equilibrium condition. A typical force-displacement curve and the best-fit curve from the standard Hertz model are shown in FIG. 10.

Results, LSM of Homogeneous Viscoelastic Hydrogels and Tissue Specimens: Three sets of agarose, polyethylene glycol di-acrylate (PEGDA), and polyacrylamide (PA) gels, covering a wide range of viscoelastic properties (G*(ω)): 47 Pa to 36 kPa, at 1 Hz) were prepared and tested using LSM. The evaluated substrates included: agarose gels (0.5% to 3% vw, N=6), PEGDA gels (6% to 15% vw, N=6), and PA gels (Acrylamide 3%, Bis-acrylamide 1% to Acrylamide 20%, Bis-acrylamide 2.5%, N=6). These gels were selected in our studies since they have been extensively incorporated within in vitro culture systems to study the influence of ECM stiffness on cellular behavior. Moreover, these gels have found widespread use in basic cellular mechanobiology, translational tissue engineering, and drug delivery research. The choice of G* range was based on values reported for various biomimetic scaffolds. Moreover, the choice of G* range was based on normal and pathological tissue shear moduli reported for a number of diseases, including atherosclerosis (1 to 30 kPa), breast carcinoma (2 to 40 kPa), IPF (1 to 20 kPa), and scleroderma (2 to 50 kPa, depending on the skin site). For each sample, $G^*(\omega)$ was measured using LSM and conventional rheology. Moreover, indentation modulus $|E|$ was obtained by AFM operated in force-mapping mode. To render the samples sufficiently scattering and maintain resemblance to scattering tissues, intralipid, for example Lyposyn™ III, 10%, Hospira, Ill., was added at 1% w/v to all specimens. The precursor solutions for agarose and PA gels were poured in 40 mm diameter petri dishes and left at room temperature until cured. The PEGDA mixtures were pipetted into silicon imaging chambers (diameter 9 mm, depth 2 mm), placed within 1 cm from a UV gun, and illuminated for 3 minutes (irradiance 170 W/cm2).

The LSM optical hardware setup and processing flow-chart are depicted in FIGS. 5 and 22, respectively. As described above, referring to FIG. 5, an excitation source 505, such as a polarized helium-neon laser (632 nm), can be focused on a sample 530 and the back-reflected speckle patterns imaged by the camera 540 through a polarizer 550 and an imaging lens 545. As further described above, information acquired by the system, including speckle frame series, can be acquired in this way and then analyzed or otherwise processed by a computer or other hardware including a processor 560.

Specifically, referring to FIG. 22, box 1 corresponds to the capturing of speckle frame series. For example, speckle images may be acquired at both parallel and perpendicular polarization states. As will be described, both a time resolved analysis 2200 and a time-averaged analysis 2202 are performed. The time resolved analysis 2200 begins at box 2 where the first speckle frame is cross-correlated with subsequent frames to return a speckle intensity auto-correlation function, $g_2(t)$, as described above. The time-averaged analysis 2202 begins at box 3 with temporal averaging of speckle frames to yield the DRP at both parallel and cross polarization states. At box 4, the $\mu_s'$ is evaluated via curve-fitting to the radial cross-polarized DRP, which is delivered, via box 5, to deduce MSD. More particularly, at box 5, optical properties determine the $\gamma$ and $\zeta$ parameters in $g_2(t) = \exp(-2\gamma (k^2 <\Delta r^2(t)>)^\zeta)$ and enable deducing the MSD. In parallel, at box 6, the ratio of parallel-polarized DRP along short and long axes (i.e. $\hat{I} = I\{\varphi=90°\}/I\{\varphi=0°\}$), is compared with a calibration curve to evaluate the average radius of scattering particles, a. This is delivered, at box 7, where the MSD and a are substituted in the generalized Stokes-Einstein relation (GSER) to calculate the $G^*(\omega)$.

Experimentally, in one configuration, speckle frames of 510×510 pixels were acquired at 739 frames per seconds (fps), for over 5 seconds at several points across the samples. Referring again to FIG. 22, temporal cross-correlation analysis of speckle frames returned the speckle intensity autocorrelation function, $g_2(t)$, as described above with respect to box 2.

In another configuration and for human breast tissue specimens, speckle frames of 1000×1000 pixels were acquired at a frame rate of 250 fps, for at least 2 seconds at multiple points across the surface. The speckle frame series acquired at cross-polarized state were processed as described earlier to obtain the $g_2(t)$ curves and the radial DRP.

Figure 11A:
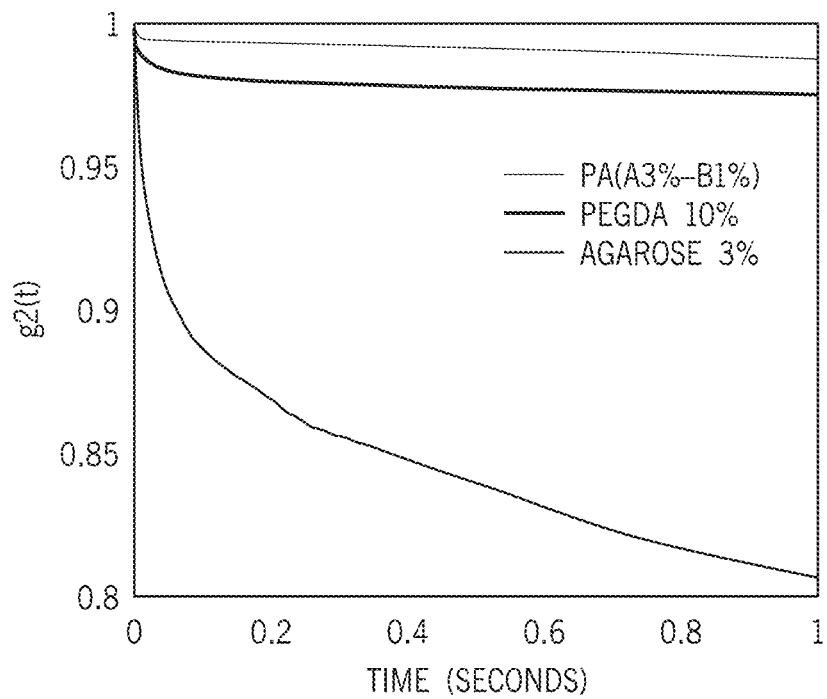
FIG. 11A provides speckle intensity correlation curves for three representative viscoelastic gels.
Figure 23A:
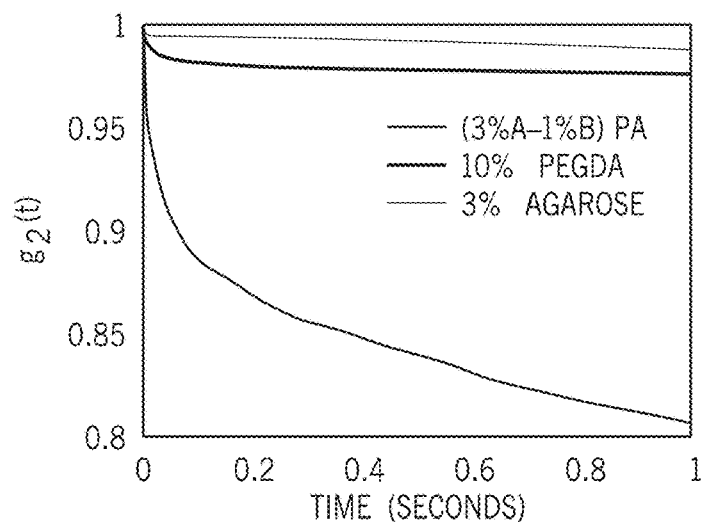
FIG. 23A provides speckle intensity autocorrelation curves, $g_2(t)$, for three representative hydrogels.

FIG. 11A displays speckle intensity correlation curves, $g_2(t)$, for three representative gels, namely agarose 3%, PA (A3%, B1%), and PEGDA 10%. Similarly, FIG. 23A provides the $g_2(t)$ curves for the same three representative gels, namely (3% A-1% B) PA, 10% PEGDA, and 3% agarose. As shown, the curve corresponding to (3% A-1% B) PA decayed considerably faster than 10% PEGDA and 3% agarose and plateaued at much lower value. In contrast, the $g_2(t)$ curve of 3% agarose decayed very slowly and plateaued at a significantly higher level. Thus, Brownian dynamics seemed to be much faster in (3% A-1% B) PA, indicating that this gel was the softest, with the lowest modulus. In contrast, particle trajectories were highly restricted in 3% agarose, implying that this gel was the most rigid one. Thus, it seems that the PA (A3%, B1%) is the softest, less elastic gel among all, and agarose 3% is the most rigid, highly elastic one. Yet, variations in optical properties could modify the $g_2(t)$ curves independent of sample viscoelasticity, and may lead to inaccurate MSD quantification. This is because the rate of speckle fluctuations is modulated by both the extent of particle displacements, and the number of scattering events encountered in optical paths. In specimens of similar viscoelastic properties, the number of scattering interactions was proportionate to the reduced scattering coefficients $\mu_s'$. Thus, $g_2(t)$ curves decayed more rapidly when $\mu_s'$ increased.

In contrast, number of scattering particles implicated in returning rays decreased with absorption coefficient, $\mu_a$, leading to slowly decorrelating $g_2(t)$ curves. Therefore, to precisely evaluate the viscoelastic properties, the influence of $\mu_a$ and $\mu_s'$ was quantified and compensated for.

Figure 11B:
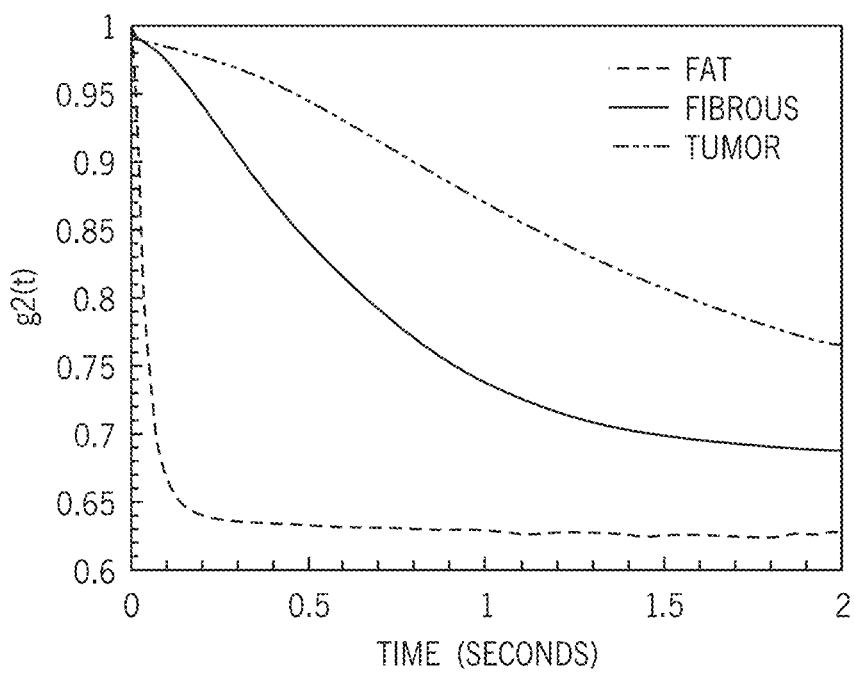
FIG. 11B provides speckle intensity correlation curves for three representative human breast tissue specimens.

FIG. 11B displays speckle intensity correlation curves, $g_2(t)$ for three representative human breast tissue specimens, namely fatty adipose, fibrous, and an invasive ductal carcinoma tumor specimen. As can be seen, the $g_2(t)$ curve corresponding to the fatty tissue decays considerably faster than the fibrous and tumor specimens, and plateaus at much lower value. In contrast the $g_2(t)$ curve of the malignant tumor decays very slowly and plateaus at a significantly higher level. Thus, it is readily inferred that the fat is the softest sample among all, and the tumor is the most rigid, highly elastic one.

Figure 12A:
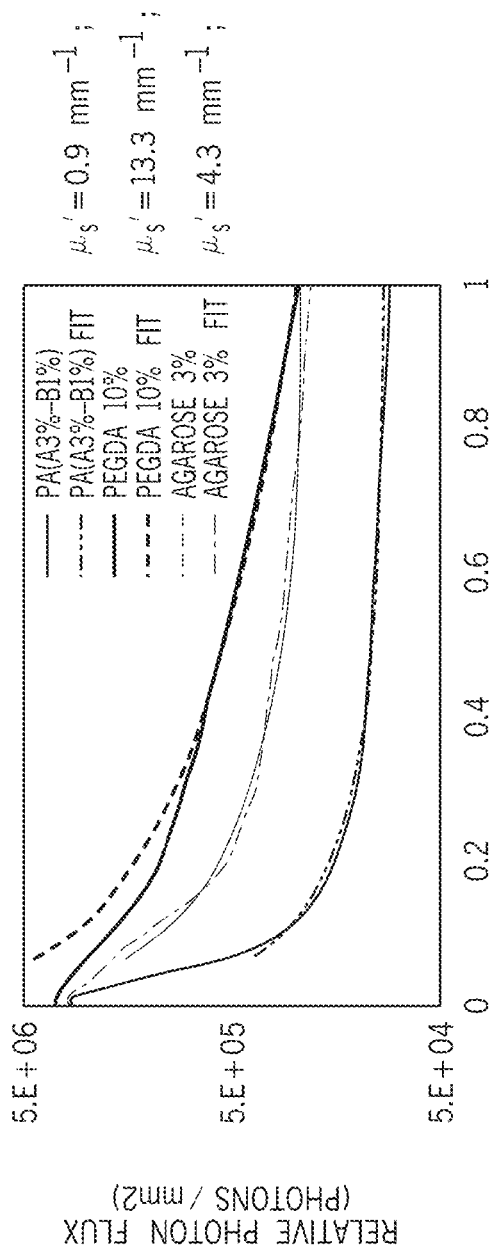
FIG. 12A provides the radial diffuse reflectance profiles (DRPs) of representative viscoelastic gels.
Figure 23B:
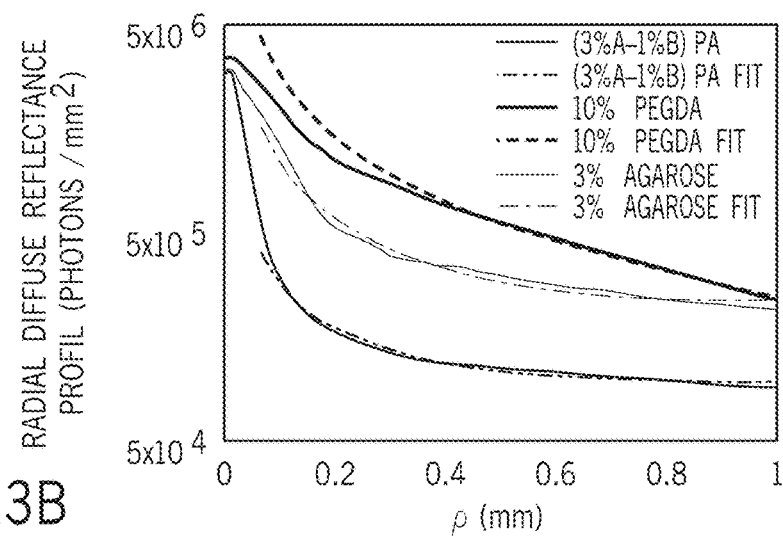
FIG. 23B provides the radial DRP of the representative gels of FIG. 23A, obtained from temporally-averaged speckle frame series (solid lines). A model function, based on diffusion theory, is fitted to the DRP curves (dashed lines) to evaluate the sample optical properties.

Both Brownian particles' displacements and optical properties contribute to speckle fluctuations and influence the $g_2(t)$ decay rates. Hence, to deduce MSD values from $g_2(t)$ curves, we estimate the optical properties of these samples. As described above with respect to box 3, the cross-polarized speckle images were time-averaged and the diffuse reflectance profile (DRP) as a function of distance from the illumination spot was measured. With the assumption that $\mu_a \sim 0$, we fitted a model obtained from light diffusion approximation to the radial DRP curve and experimentally calculated the $\mu_s'$ (FIG. 22, boxes 3 and 4). The radial DRP of the representative gels are depicted in FIG. 12A. Moreover, the radial DRP of (3% A-1% B) PA, 10% PEGDA, and 3% agarose are also shown in FIG. 23B along with the fitted curves, revealing distinct $\mu_s'$ values of 0.9, 13.3, and 4.3 mm$^{-1}$, respectively. More specifically, comparison of the peak of radial DRP curves indicates that the PEGDA 10% is highly scattering compared to the agarose 3% and PA (A3%, B1%) gels. Curve-fitting to radial DRP curves confirms that $\mu_a = 0$ for all gels and us is equal to 0.9, 13.3, and 4.3 mm$^{-1}$ for PA (A3%, B1%), PEGDA 10%, and agarose 3%, respectively. Despite substantially identical intra-lipid concentrations in all viscoelastic gels, the samples exhibit different optical appearance, likely due to differences in refractive index mismatch and curing protocols, as discussed later. For example, the stronger scattering from PEGDA and agarose gels are likely due to UV radiation and heating.

Figure 12B:
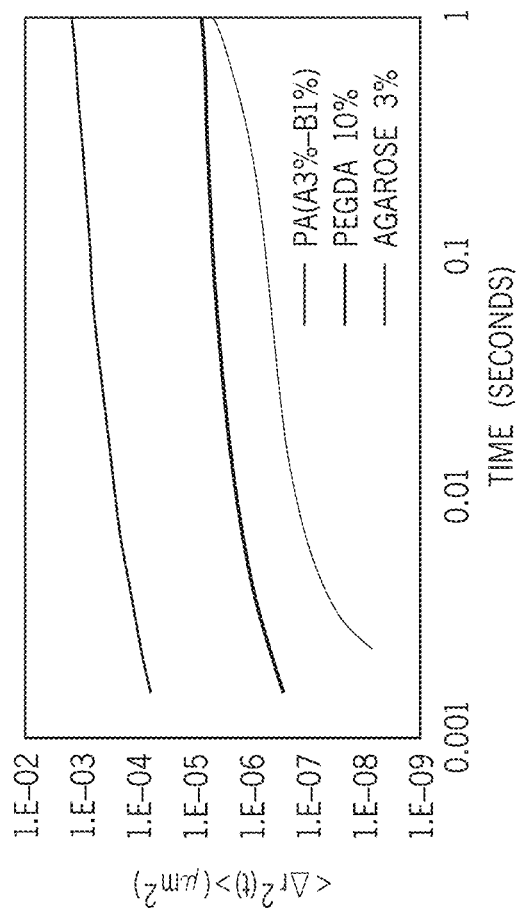
FIG. 12B provides the mean square displacements (MSDs) of Brownian particles in viscoelastic gels.

Given $\mu_a$ and $\mu_s'$, the $g_2(t)$ curves were uniquely expressed in terms of the MSD of Brownian particles (FIG. 22, box 5). To derive the MSD values, $<\Delta r^2(\tau)>$, from $g_2(t)$ in moderately scattering samples of negligible absorption, the following equation can be used: $g_2(t)=\exp(-2\gamma(k^2<\Delta r^2(t)>)^\zeta)$. Here $\gamma$ and $\zeta$ were empirical variables, related to $\mu_s'$, and k was the wavenumber. Thus, MSD values are deduced from $g_2(t)$ curves, using the above empirical equation obtained from Correlation-Transfer Monte-Carlo Ray Tracing (CT-MCRT) simulation of light transport in a medium of the corresponding $\mu_s'$ values. FIG. 12B displays the MSD of Brownian particles in the aforementioned gels. Moreover, FIG. 23C also displays the MSD of intralipid particles within the representative gels. Extended MSD trajectories were observed in the (3% A-1% B) PA, as opposed to 10% PEGDA and 3% agarose specimens. In other words, as can be seen, the scattering particles experience extended trajectories in the PA (A3%, B1%) gel. However, these movements are extremely limited in the PEGDA 10% and agarose 3% specimens. The acute sensitivity of LSR to particle displacements of a few angstroms was evident within the highly viscoelastic 3% agarose. Unlike a simple linear trend in purely viscous fluids, the MSD curves of FIG. 22C, exhibited non-trivial behaviors, reflecting the complex viscoelastic nature of the microenvironment.

The extent and scale of Brownian displacements are related to the scattering particle size and the viscoelastic susceptibility of the microenvironment. Thus, to extract the $G^*(\omega)$, both MSD and scattering particle size should be known (see Eqn. 4). In other words, since for given viscoelastic and optical properties, smaller intrinsic scattering particles have greater MSD trajectories, the average size, a, of light scattering particles should be estimated beforehand to enable deducing the absolute magnitude of $G^*(\omega)$. We have previously reported a straightforward approach that enables estimating the scattering particle size from azimuth angle dependence of DRP patterns, collected in the parallel-polarization state.

Figure 13A:
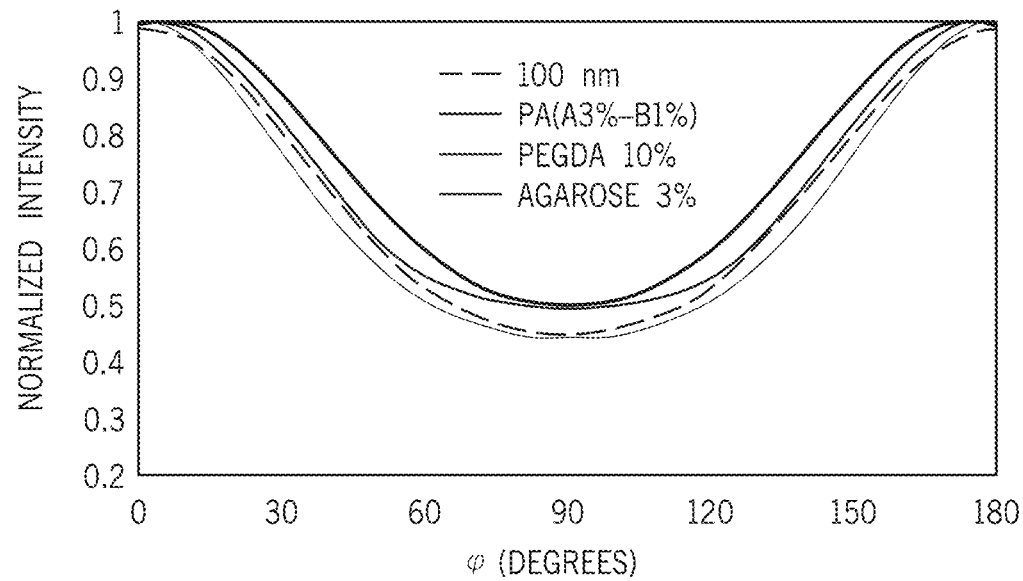
FIG. 13A provides normalized intensity values versus azimuth angle for three viscoelastic gels.

The approach of evaluating the average radii of scattering particles, a, from the speckle frame series, is depicted in FIG. 22, box 6). Co-polarized speckle images may be temporally averaged and converted to relative DRP as a function of azimuth-angle. We then calculated the ratio of DRP across short and long axes, i.e. $\hat{I}=I(\varphi=90°)/I(\varphi=0°)$, and compared it with a calibration curve to identify the corresponding a. FIG. 13A displays the normalized intensity values versus azimuth angle for all three gels. The theoretical curve corresponding to a scattering sample with a scattering particle radius of 100 nm is also displayed (gray, dashed line). Moreover, FIGS. 24A-D show co-polarized DRP images and the relative DRP versus azimuth angle for (3% A-1% B) PA, 10% PEGDA, and 3% agarose. The $\hat{I}$ values of 0.48, 0.46, and 0.45, respectively, corresponding to a~100 nm for all gels, consistent with previous reports on the particle size distribution of intralipid, as discussed later. The MSD evaluated above and a=100 nm were then replaced in the generalized Stokes-Einstein relation (GSER) to derive $G^*(\omega)$ as shown in FIG. 2, box 7 (Eqn. 4).

Figure 13B:
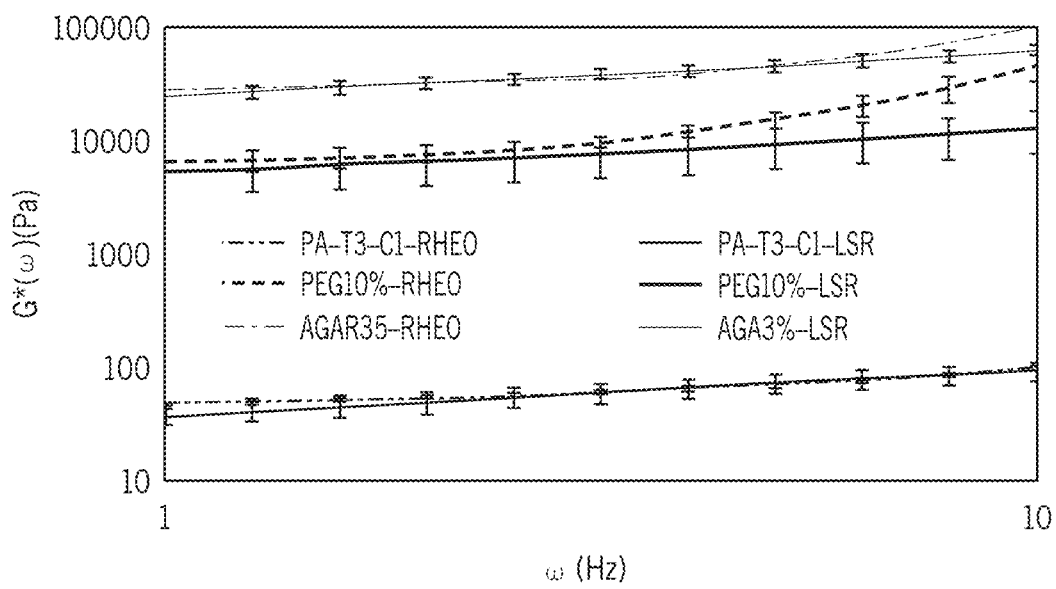
FIG. 13B provides the frequency-dependent viscoelastic modulus ($G^*(\omega)$) curves obtained from LSM and conventional mechanical rheology for representative viscoelastic gels.
Figure 14:
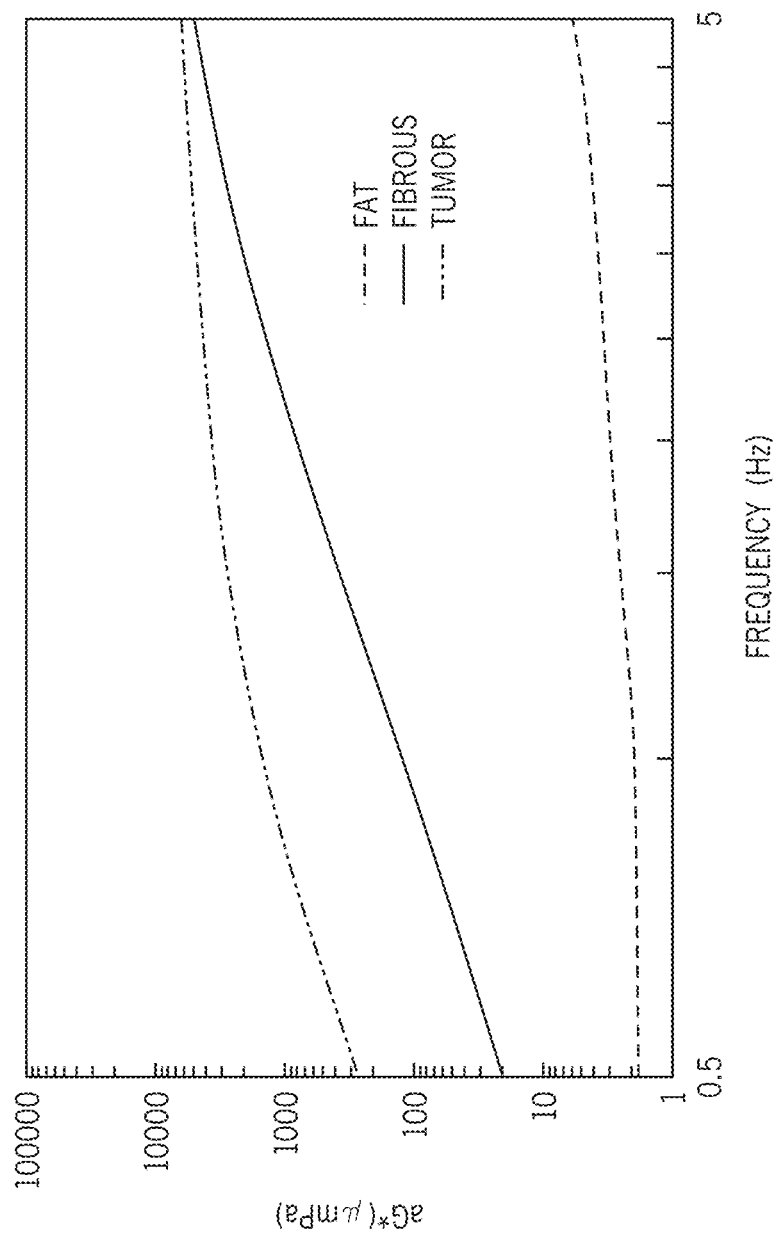
FIG. 14 provides volume-averaged $G^*$ of fatty, fibrous, and malignant human breast tissue.
Figure 25A:
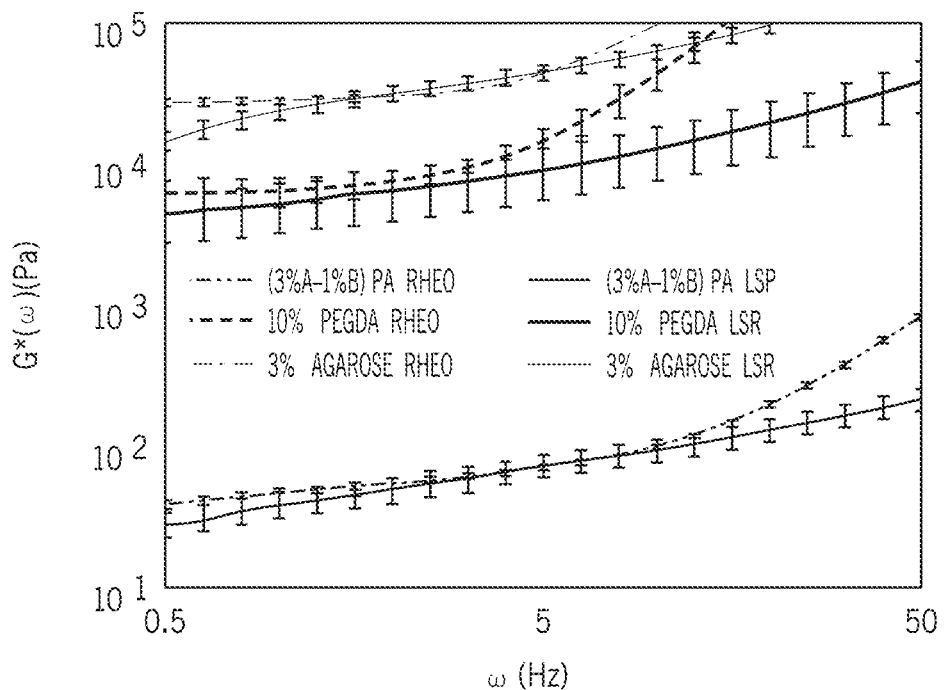
FIG. 25A provides the complex viscoelastic modulus, $G^*(\omega)$, curves obtained from LSR (solid lines) and mechanical rheometry (dashed line) for (3% A-1% B) PA, 10% PEGDA, and 3% agarose. Close correspondence is observed between the two measurements over the frequency range of 0.5-10 Hz. Deviations at higher frequencies are due to emergence of inertial effects in conventional rheology, which can make the results unreliable. Divergences at frequencies below 0.1 Hz are caused by the significant influence of compressional, rather than shear fluctuations of the hydrogel network, on the slow Brownian dynamics at these frequencies.

Comparison with Mechanical Rheometry: LSR measurements of $G^*(\omega)$ in homogeneous hydrogels were compared with mechanical rheometry results. Mechanical rheometry is a traditional standard for evaluating bulk $G^*(\omega)$, by destructively shearing the specimen between two plates and calculating the stress to strain ratio at few deformation frequencies. FIG. 13B displays the $G^*(\omega)$ curves obtained from LSM (solid lines) and conventional mechanical rheology (dashed line) for the 3 representative gels over the frequency range of 1 to 10 Hz. Similarly, FIG. 25A shows the $G^*(\omega)$ curves obtained from LSR (solid lines) compared with those evaluated by a mechanical rheometer (ARG2, TA Instruments, DE, dashed lines) for the 3 representative hydrogels. Similar to rheometry, LSR accurately detected the relative differences in the viscoelastic compliance of the hydrogels. Furthermore, the absolute magnitudes of $G^*(\omega)$, obtained from LSR, closely agreed with mechanical rheometry, particularly within 0.5-10 Hz range. For instance, $G^*(\omega)$ values measured by LSR at 1 Hz for (3% A-1% B) PA, 10% PEGDA, and 3% agarose were: 39±7 Pa, 5.3±2 kPa, and 22.6±2.9 kPa, respectively. For the same gels, mechanical rheometry reported similar values of 47±2 Pa, 6.5±1.5 kPa, and 28.1±1.3 kPa, at 1 Hz. Above 10 Hz mechanical rheometry became unreliable due to tool inertia, as discussed later. This was more evident in 10% PEGDA and 3% agarose gels, for which we used a smaller rheometer top plate (8 mm diameter). Using a larger 40 mm tool for mechanical rheometry of (3% A-1% B) PA increased the contact area and partially alleviated the inertial effect, as evidenced by the smaller deviations of rheometry measurements from the LSR results. At low frequencies (<0.5 Hz) the LSR-derived moduli deviated from mechanical rheometry because the slow Brownian dynamics at these frequencies were largely caused by compressional, but not shear fluctuations of the hydrogel network. In other words, at lower frequencies, thermally-driven scattering particles are modulated by both shear and longitudinal modes of the viscoelastic network. Thus, the evaluated $G^*$ values may deviate from those obtained using rotational shear rheology, as discussed later. Similarly FIG. 14 depicts the $G^*(\omega)$ curves obtained from LSM for the 3 representative human tissue specimens over the frequency range of 0.5 to 5 Hz. It can be seen that the fatty adipose is the softest specimen and the tumor is the most rigid one.

Figure 15A:
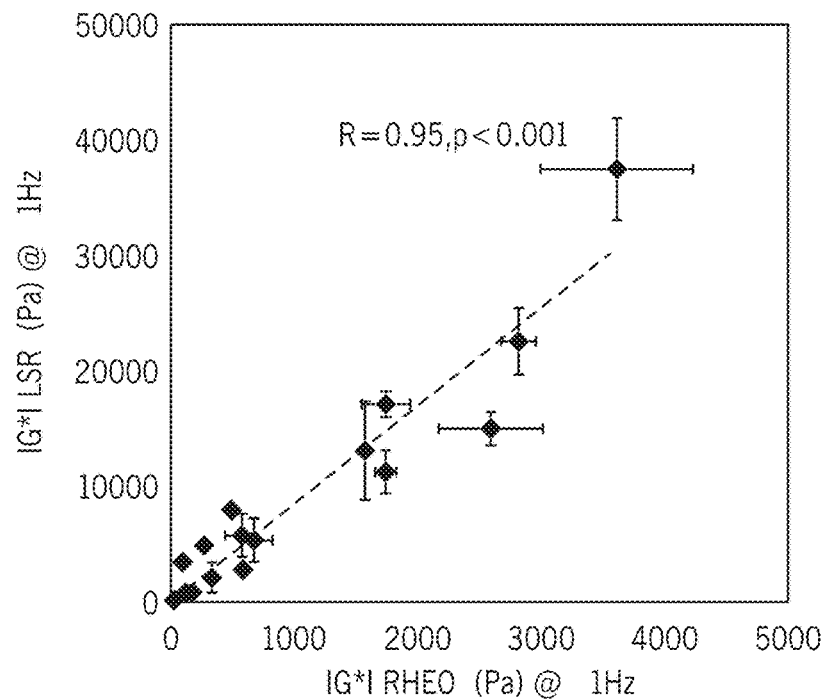
FIGS. 15A and 15B provide scatter diagram for $G^*$, derived from LSM, versus $G^*$ and indentation modulus (E) evaluated using a mechanical rheometer and atomic force microscopy (AFM), respectively. More particularly.
Figure 25B:
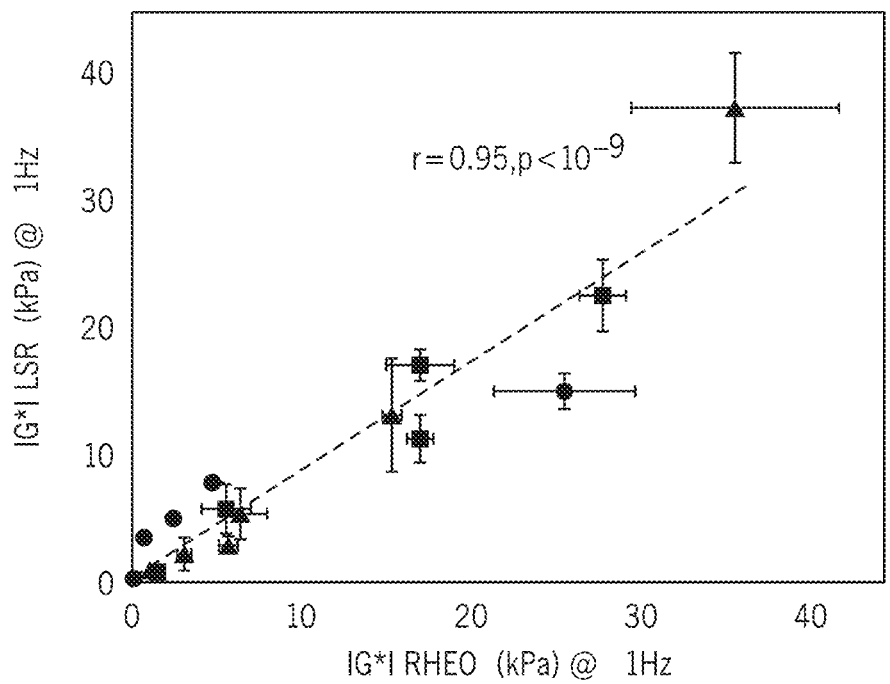
FIG. 25B provides a scatter diagram of $|G^*(\omega)|$ evaluated at 1 Hz obtained from LSR and conventional rheology for all the gels (N=18, PA gels: circles, PEGDA gels: triangles, agarose gels: squares). A strong, statistically significant correlation is observed between the two measurements over the moduli range of 47 mPa to 36 kPa (r=0.95, p<$10^{-9}$). Z-test analysis confirmed that the difference between LSR and rheometry measurements is insignificant (p=0.08).

FIG. 15A and FIG. 25B depict the scatter diagram of |G*| at 1 Hz evaluated by LSM and conventional rheology (N=18). A strong, statistically significant correlation (r=0.95, p<$10^{-9}$) was observed between LSR and mechanical rheometry across the whole moduli range from the softest hydrogel at 47 Pa ((3% A-1% B) PA) to the most rigid one at 36 kPa (15% PEGDA). Furthermore, z-test analyses indicated that differences between moduli measured by LSR were not significantly different from those measured by mechanical rheometry (p≥0.08), demonstrating the accuracy of LSR in quantifying the frequency-dependent $G^*(\omega)$ over multiple decades of moduli from a few Pa to tens of kPa.

Figure 15B:
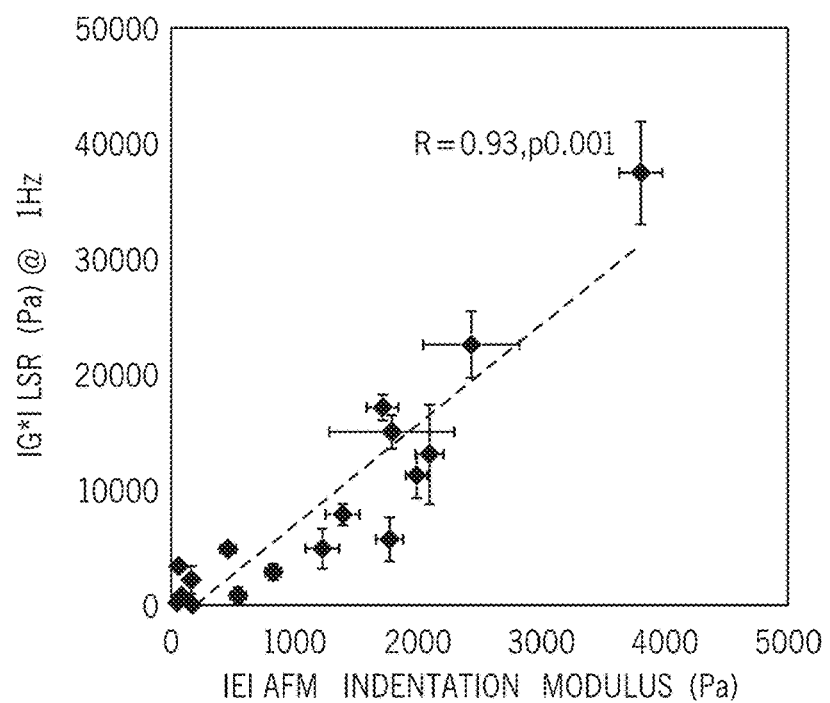
Figure 26A:
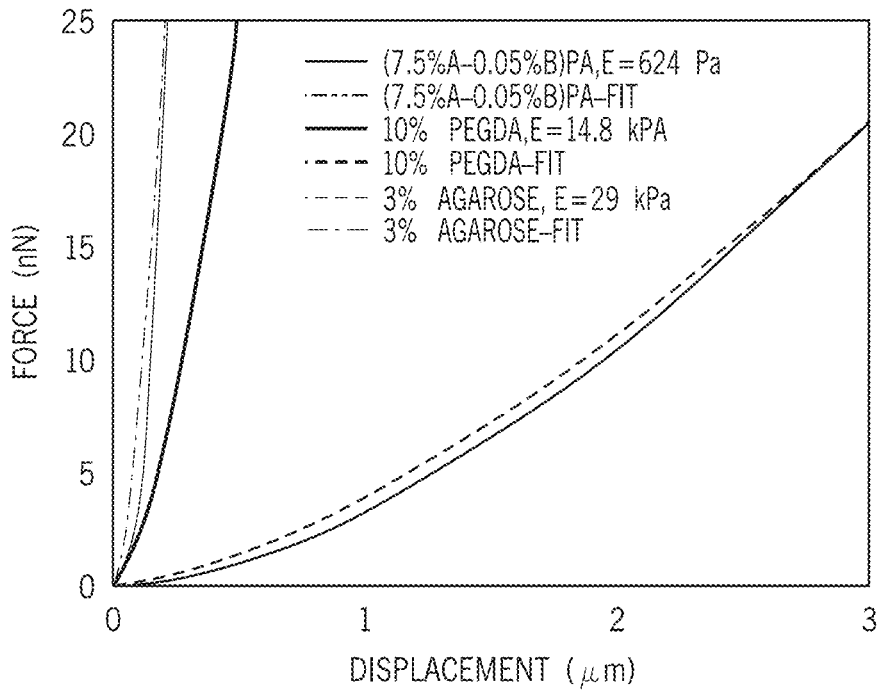
FIG. 26A provides typical force-distance curves for representative hydrogels. The corresponding best fitted curves (bottom two), obtained using the Hertzian model are also displayed.
Figure 26B:
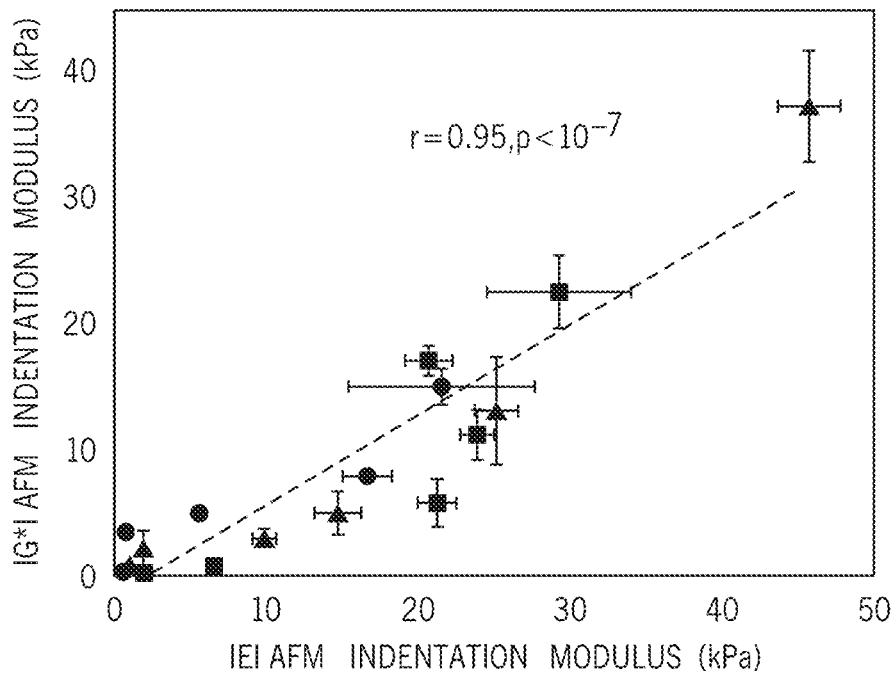
FIG. 26B provides a scatter diagram of $|G^*(\omega)|$ values at 1 Hz obtained from LSR and the indentation modulus, E, measured by AFM at an indentation rate of 2 μm/s for viscoelastic gels (N=17, PA gels: circles, PEGDA gels: triangles, agarose gels: squares). Linear regression analysis declares a strong, statistically significant correlation (r=0.92, p<10$^{-7}$) for E: 624 Pa to 46 kPa.
Figure 27A:
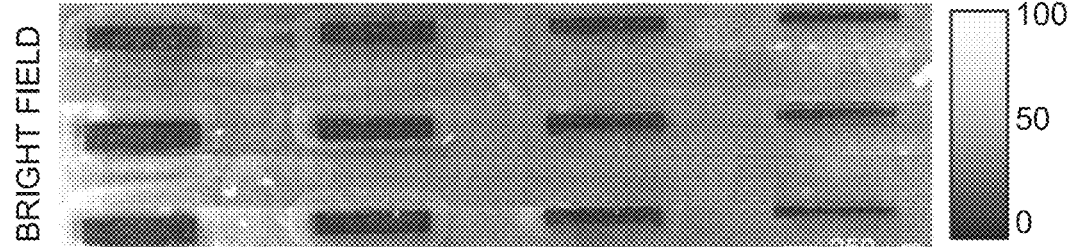
FIG. 27A provides a bright field image of an exemplary micro-fabricated composite PDMS-PEGDA phantom. A total of 12 PDMS bars are visible within the PEGDA background. The bars in successive columns are 1 mm long and 200, 150, 100, and 80 µm wide, respectively.
Figure 27B:
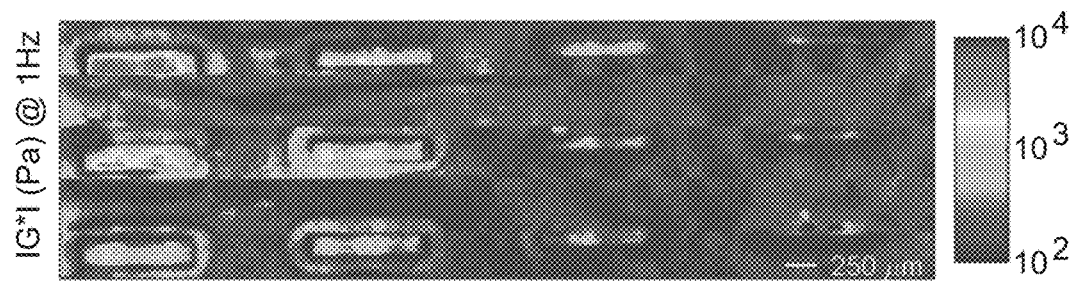
FIG. 27B provides spatially-resolved G*, evaluated at 1 Hz. In the color-bar, the moduli range of 100 Pa to 10 kPa are represented by blue to red hues. The 80 µm wide bars are barely visible at 1 Hz.
Figure 27C:
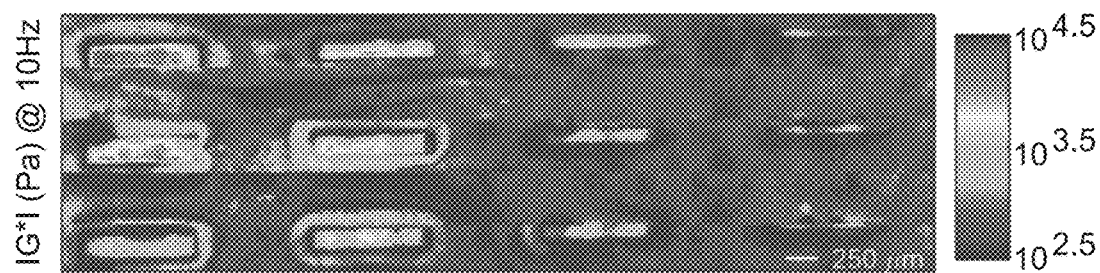
FIG. 27C provides partially-resolved G*, evaluated at 10 Hz. In the color-bar, the moduli range of 300 Pa to 300 kPa are represented by blue to red hues. The 80 µm wide stiff bars are distinguished within the plain soft PEGDA 5% background.
Figure 27D:
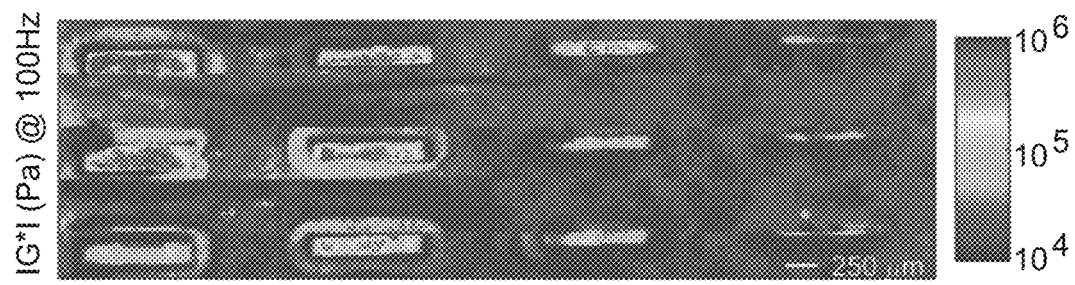
FIG. 27D provides spatially-resolved G*, evaluated at 100 Hz. In the color-bar, the moduli range of 10 kPa to 1 MPa are represented by blue to red hues. Significant contrast is observed between stiff PDMS bars and the PEGDA 5% background at all length-scales.
Figure 28A:
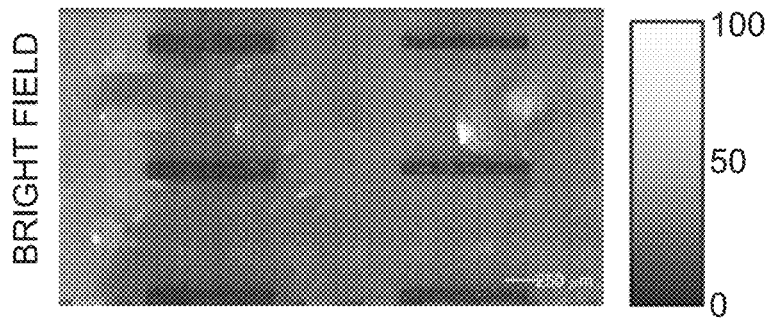
FIG. 28A provides a bright field image of the micro-fabricated composite PDMS-PEGDA 10% phantom. A total of 6 PDMS bars are visible within the PEGDA background. The bars in successive columns are 1 mm long, and 100 and 80 µm wide, respectively.
Figure 28B:
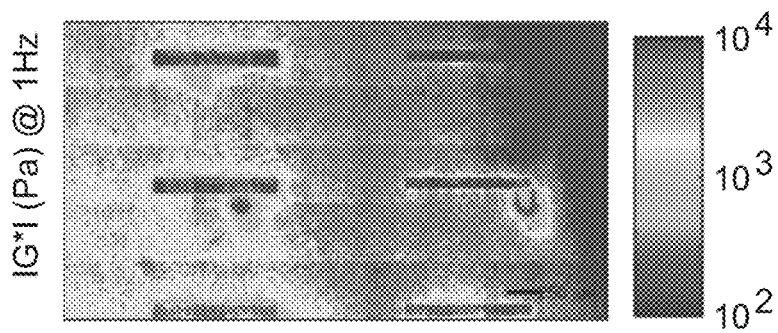
FIG. 28B provides spatially-resolved G*, evaluated at 1 Hz. In the color-bar, the moduli range of 100 Pa to 10 kPa are represented by blue to red hues.
Figure 28C:
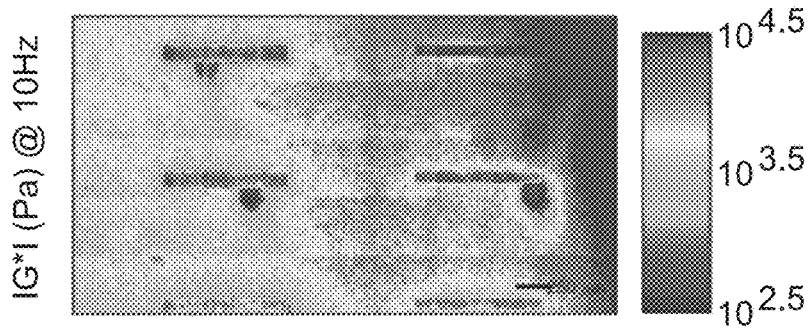
FIG. 28C provides spatially-resolved G*, evaluated at 10 Hz. In the color-bar, the moduli range of 300 Pa to 300 kPa are represented by blue to red hues.
Figure 28D:
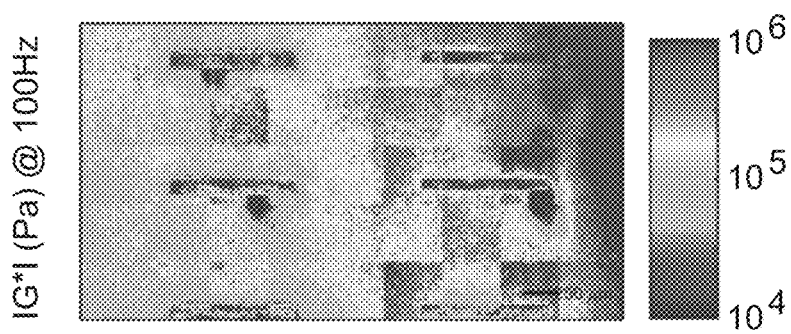
FIG. 28D provides spatially-resolved G*, evaluated at 100 Hz. In the color-bar, the moduli range of 10 kPa to 1 MPa are represented by blue to red hues. Compared to FIG. 27, the contrast between PDMS bars and the PEGDA 10% background is reduced at all length-scales and frequencies. Moreover, higher stiffness of the gel constituents prevent leakage between various compartments and leads to more defined borders and increased homogeneity of moduli within the bars.

Comparison With AFM-Based Indentation: The viscoelastic modulus at the micro-scale experienced by cells may not be identical to macro-scale properties of scaffolds. Thus, approaches that measure micro-scale mechanical properties provide unique advantages for cell-scaffold studies. The current reference standard for measuring micro-scale properties is AFM-based indentation. Therefore, we further assessed the relationship between |$G^*(\omega)$| evaluated by LSR and micro-indentation moduli, E, evaluated by AFM-based indentation in the above hydrogels. To obtain AFM measurements, the specimens were indented by a small cantilevered-probe and E was calculated by fitting the Hertz model to the curve displaying the applied force versus cantilever displacement. The (3% A-1% B) PA gel was too soft and adhesive for indentation and had to be excluded from the analysis. As such, AFM measurements were conducted on a total of 17 out of 18 prepared hydrogels. FIG. 26A displays the typical force-displacement curves for (7.5% A-0.05% B) PA, 3% agarose, and 10% PEGDA gels at the approach rate of 2 μm/s. The rapidly increasing force in 3% agarose and 10% PEGDA, compared to (7.5% A-0.05% B) PA, pointed to the higher elastic moduli of these gels. The E was calculated as 624±27 Pa, 14.8±1.5 kPa, and 29.2±4.7 kPa for (7.5% A-0.05% B) PA, 10% PEGDA, and 3% agarose, respectively. FIG. 15B and FIG. 26B display the scatter diagram of LSR-measured $|G^*(\omega)|$ values at 1 Hz evaluated using LSM and the indentation modulus, $|E|$, evaluated by AFM at the approach rate of 2 μm/s for all viscoelastic gels, except the PA, A3%, and B1% (N=17). Results of linear regression analysis demonstrate a statistically significant correlation (r=0.92, p<$10^{-7}$) between the two measurements for E: 624 Pa-46 kPa, establishing that $|G^*(\omega)|$ measured by LSR were closely related with E measured by AFM. Results depicted in FIGS. 15A and 15B demonstrate the capability of LSM in evaluating both bulk and micro-scale viscoelastic properties of tissue and biomaterials.

Micro-Mechanical Mapping of $G^*(\omega)$ Using LSM: We further examined the capability of LSR for merging the advantages of standard mechanical rheometry that measures frequency-dependent viscoelastic behavior with mechanical mapping of spatial heterogeneities at the micro-scale. Soft lithography techniques were used to construct substrates with heterogeneous viscoelastic features of tens of microns in size. A composite PDMS-PEGDA gel was microfabricated, featuring stiff PDMS bars of assorted widths surrounded by soft PEGDA 5% hydrogel. For micromechanical assessment of viscoelastic properties, the substrate was illuminated by an expanded beam and scanned at 450 μm steps in transverse direction. Speckle images were acquired at 250 fps, for 1 second, through an objective lens (10×, NA=0.25, Olympus). Spatio-temporal processing of speckle frames returned the $g_2(t)$ curve for individual pixels from which spatially-resolved $G^*(\omega)$ was deduced, as explained above. FIGS. 27A-D display the bright-field image and the 2D spatially-resolved LSR color-map of $|G^*(\omega)|$ within the micro-patterned substrate at 1, 10, and 100 Hz. The PDMS bars in successive columns of FIG. 27A were 1 mm long, and 200, 150, 100, and 80 μm wide, respectively. The color-bars in FIGS. 27B-D were scaled to provide the highest contrast at the corresponding frequencies. The regions of increased stiffness in $G^*$ maps coincided with PDMS bars in the bright field image, whereas softer regions corresponded to PEGDA 5% background. The increased stiffness of PEGDA 5% around the bars was likely due to drying, and closely mirrored similar features in the bright-field image. Comparison of FIGS. 7B-D revealed that the $G^*$ map, evaluated at 100 Hz, exhibited the highest contrast and resolution. The modest resolution and contrast of $G^*$ color maps at low frequencies was due to reduced spatial and temporal averaging employed in calculating the pixel-wise $g_2(t)$ curves, at longer decorrelation times, which in turn limited the statistical accuracy of MSDs at longer times, and $G^*$ at lower frequencies. Comparison of mechanical rheometry measurements with $G^*$ color-maps yielded similar values: $G^*$ (at 1 Hz) for PEGDA 5% was 275±122 Pa by rheometry and 272±0.9 Pa by LSR; and for PDMS was 10.8±2.1 kPa by rheometry and 7±0.03 kPa by LSR. From FIGS. 27A-D, it was clear that LSR conveniently resolved even the smallest 80 μm-wide stiffer PDMS bars from the soft PEGDA 5% background. Moreover, heterogeneous moduli were identified within the bars, demonstrating the resolution and sensitivity of LSR to variations in $G^*$ at length scales of a few 10 μm. These heterogeneities were likely caused by variations in casting of PDMS elastomer within the soft background and the leakage of soft PEGDA gel to the PDMS compartments. A test phantom was also constructed, with smaller differences between the moduli of the bars and the background gel, composed of PEGDA 10% ($G^*$=6.5±1.5 kPa at 1 Hz) and PDMS ($G^*$=10.8±2.1 kPa at 1 Hz) (see FIGS. 28A-D). These gels were stiffer and hence easier to cast. Thus, the composite gel exhibited more defined borders and the bars appeared less heterogeneous. Moreover, since the difference between the moduli of the background and the bars was smaller, the contrast between the two sections was reduced. These results demonstrated the capability of LSR to render spatially heterogeneous, frequency-dependent viscoelastic properties of materials with micro-scale resolution and high sensitivity to moduli differences.

Figure 29B:
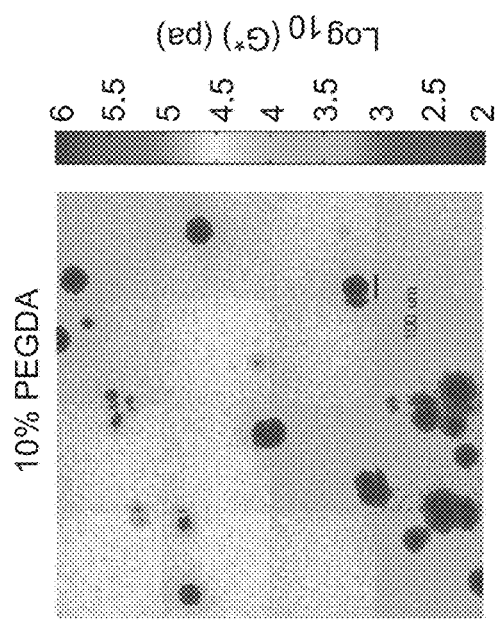
FIG. 29B provides spatially-resolved G*, evaluated at 100 Hz for the plane 10% PEGDA gel. In the color-bar, the moduli range of 100 Pa to 1 MPa are represented by blue to red hues.
Figure 29A:
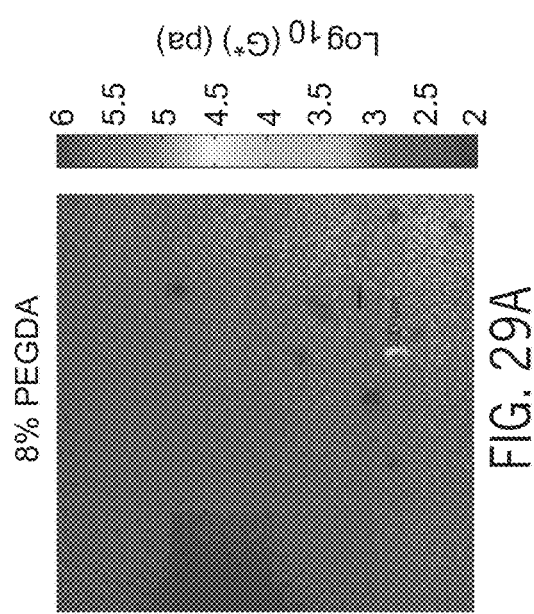
FIG. 29A provides spatially-resolved G*, evaluated at 100 Hz for the plane 8% PEGDA gel. In the color-bar, the moduli range of 100 Pa to 1 MPa are represented by blue to red hues.
Figure 29C:
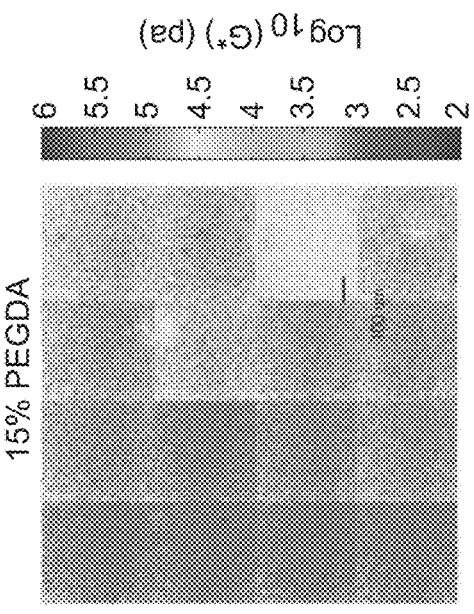
FIG. 29C provides spatially-resolved G*, evaluated at 100 Hz for the plane 15% PEGDA gel. In the color-bar, the moduli range of 100 Pa to 1 MPa are represented by blue to red hues.

To further examined the capability of LSM for merging the advantages of standard mechanical rheometry that measures frequency-dependent viscoelastic behavior with mechanical mapping of spatial heterogeneities at the micro-scale, we also evaluated the 2D viscoelasticity profile of PEGDA gels. FIGS. 29 A-C display the spatial 2D distribution of $G^*$ across the surface of PEGDA gels with polymer concentrations of 8%, 10%, and 15%. The spatial maps reveal the gradients of stiffness and viscoelasticity over the scanned area, which is likely created due to non-uniform, Guassian distribution of UV illumination system. The $G^*$ maps further reveal that the overall $G^*$ is dependent on the polymer concentrations and the PEGDA gels become stiffer as the polymer concentration increases. Moreover, the maps display small regions of reduced stiffness, within the low concentration gels that likely correspond to pools of water within the large pores of the gels. From the size of the pools it is readily inferred that the passive LSM embodiment is able to resolve mechanical features as small as a few 10 s of microns within mechanically heterogeneous materials.

Next we demonstrated the utility of LSM in evaluating the micromechanical properties of tissue specimens. Collagen is the most abundant fibrous protein in the tumor ECM and the main contributor to the tensile strength. Therefore, the accuracy of LSM images can be verified through co-registration with collagen content. Toward this end, we use second harmonic generation imaging in combination with confocal microscopy to obtain the tissue collagen content. SHG is a non-linear two-photon microscopy scheme that relies on the susceptibility of the specimen to generate second harmonic light from the incident illumination. The non-centrosymmetric structure of collagen fibers creates a strong SHG signal when illuminated at 780 nm. Second harmonic light is exactly half the wavelength of illuminated light (frequency-doubled). $G^*(\omega)$ maps obtained from LSM were co-registered with SHG images. Compliant regions in $G^*(\omega)$ maps, evaluated by LSM, corresponded to low SHG signal and adipose tissue. Likewise, rigid regions identified by LSM matched high SHG signal induced by desmoplastic collagen accumulation.

Figure 17:
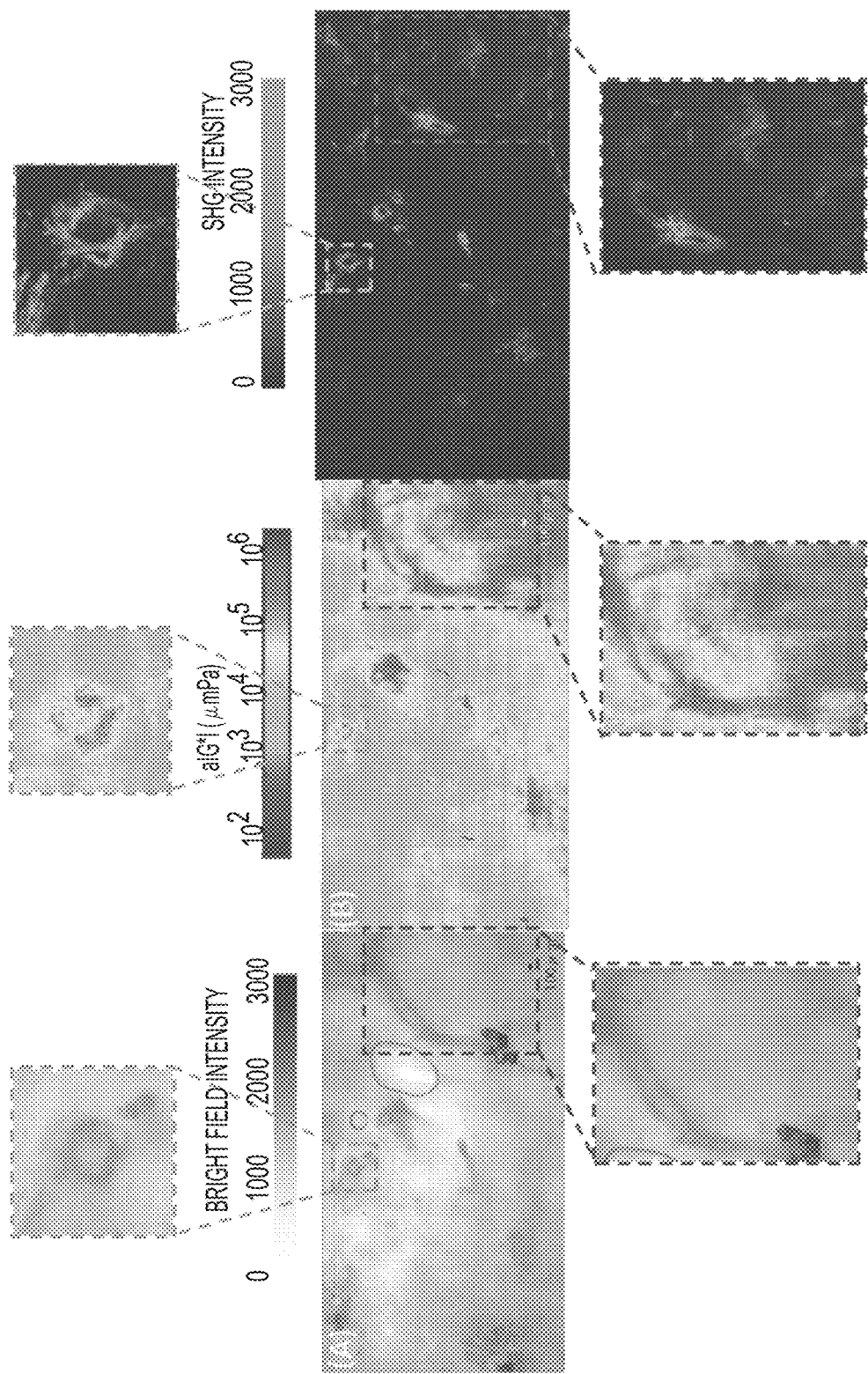
FIG. 17 provides bright field images (left), LSM $G^*$ maps (middle), and second harmonic generation microscopy (SHG) signal (right) for a low-grade invasive ductal carcinoma specimen.

FIG. 17 displays the bright field images (panel A on the left), the LSM $G^*$ maps (panel B in the middle), and the SHG signal (panel C on the right) for a low-grade invasive ductal carcinoma specimen. As cab be seen, LSM can identify small micromechanical features such as blood vessels and ducts, which exhibit distinct elasticity compared to the neighboring tissue. It can also visualize regions of high and low collagen concentration, as highlighted in magnified sections (at the top and bottom).

Figure 18:
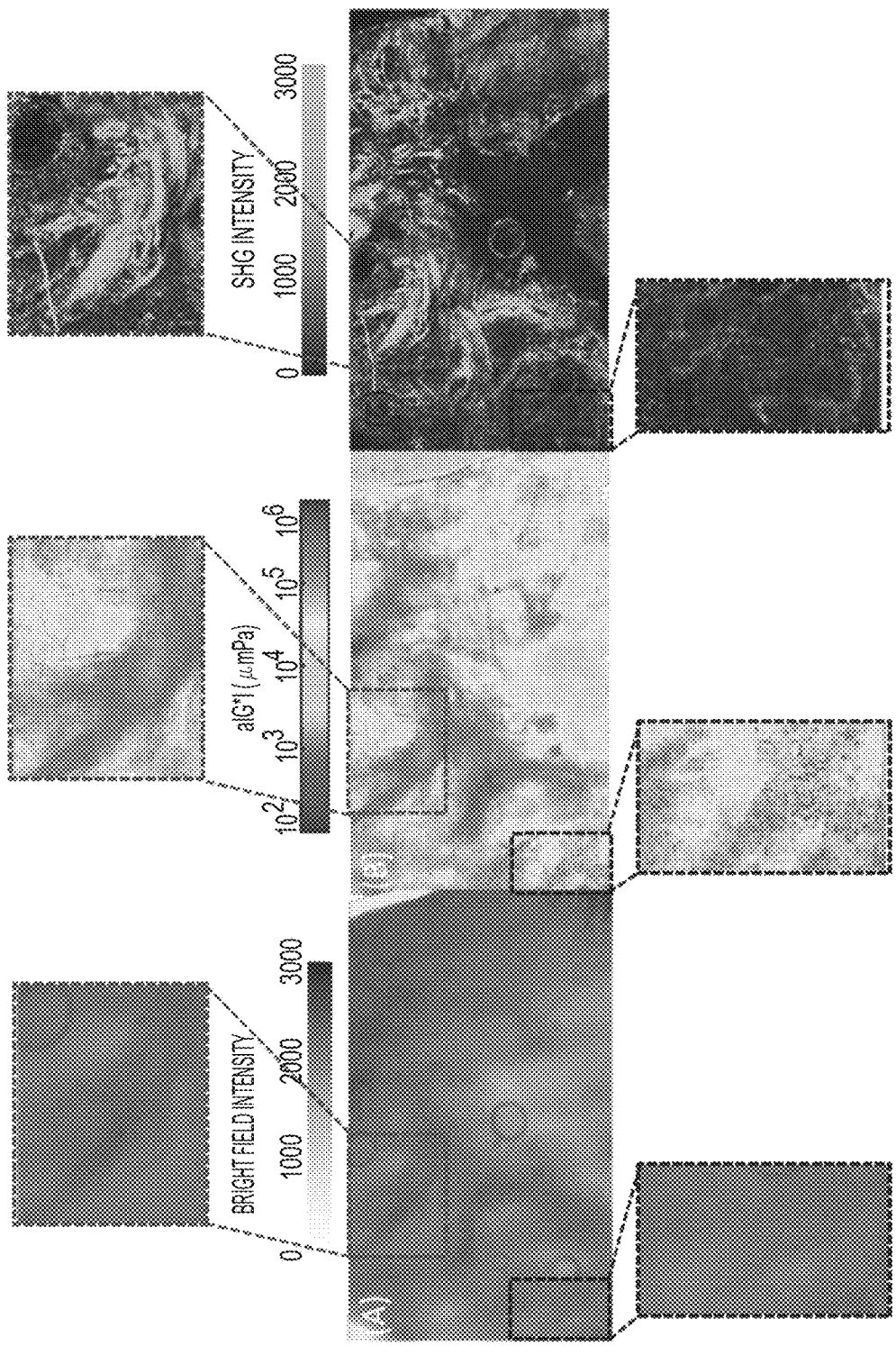
FIG. 18 provides bright field images (left), LSM $G^*$ maps (middle), and SHG signal (right) for a high-grade invasive ductal carcinoma specimen.

FIG. 18 displays the bright field images (panel A on the left), the LSM $G^*$ maps (panel B in the middle), and the SHG signal (panel C on the right) for a high-grade invasive ductal carcinoma specimen. Bundled and thickened collagen fibers are readily visible in the magnified section. Additionally, fatty adipose tissue in the bright field image correlates with regions of lower $G^*$ and dimmer SHG signal intensity.

Figure 19:
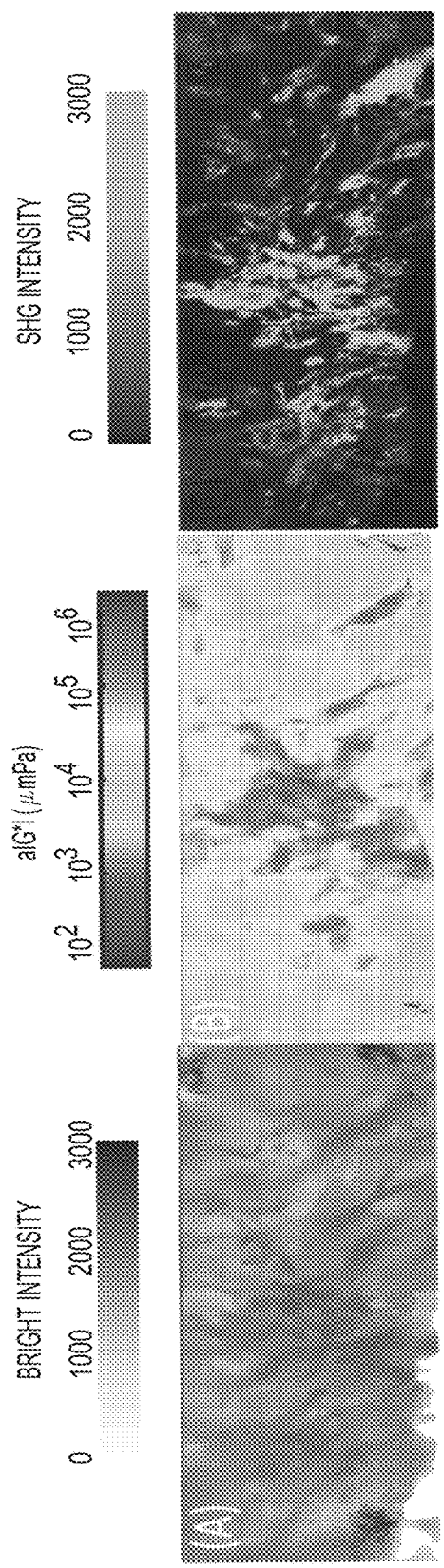
FIG. 19 provides bright field images (left), LSM $G^*$ maps (middle), and SHG signal (right) for an invasive lobular carcinoma specimen.

FIG. 19 displays the bright field images (panel A on the left), the LSM G* maps (panel B in the middle), and the SHG signal (panel C on the right) for an invasive lobular carcinoma specimen. The specific signature of collagen arrangement in lobular carcinoma is readily apparent in the LSM and SHG images.

Figure 20:
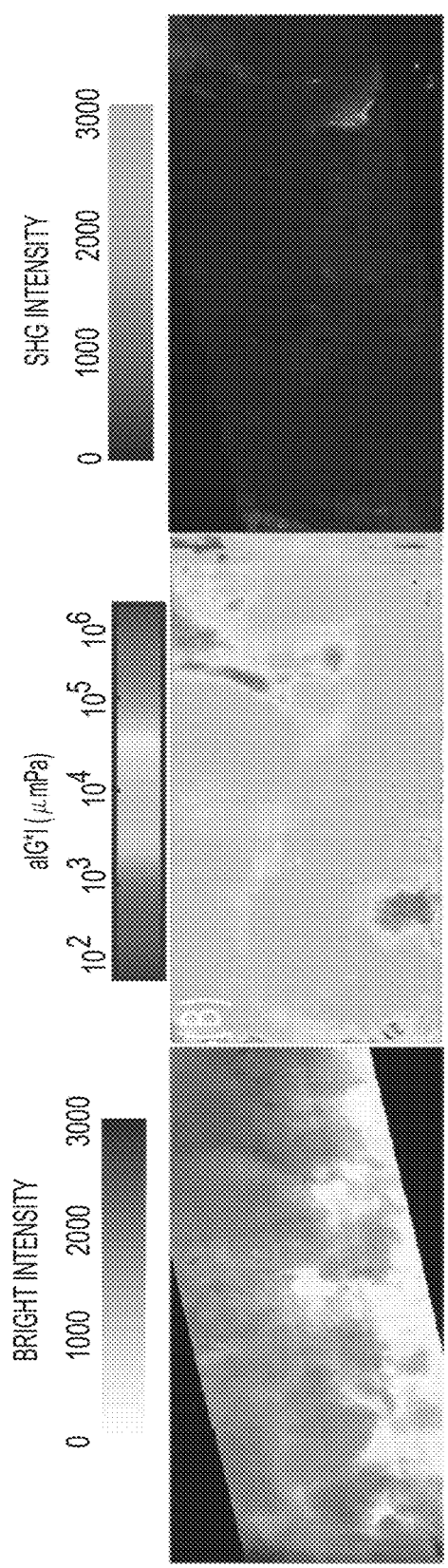
FIG. 20 provides bright field images (left), LSM $G^*$ maps (middle), and SHG signal (right) for an invasive ductal carcinoma specimen with a majority of mass composed of cellular mucinous.

FIG. 20 displays the bright field images (panel A on the left), the LSM G* maps (panel B in the middle), and the SHG signal (panel C on the right) for an invasive ductal carcinoma specimen with a majority of mass composed of cellular mucinous. This is a rare form of invasive ductal carcinoma, where tumor is composed of neoplastic cells floating in mucin lakes. As such the tumors tend to be primarily viscous and relatively soft.

Figure 21:
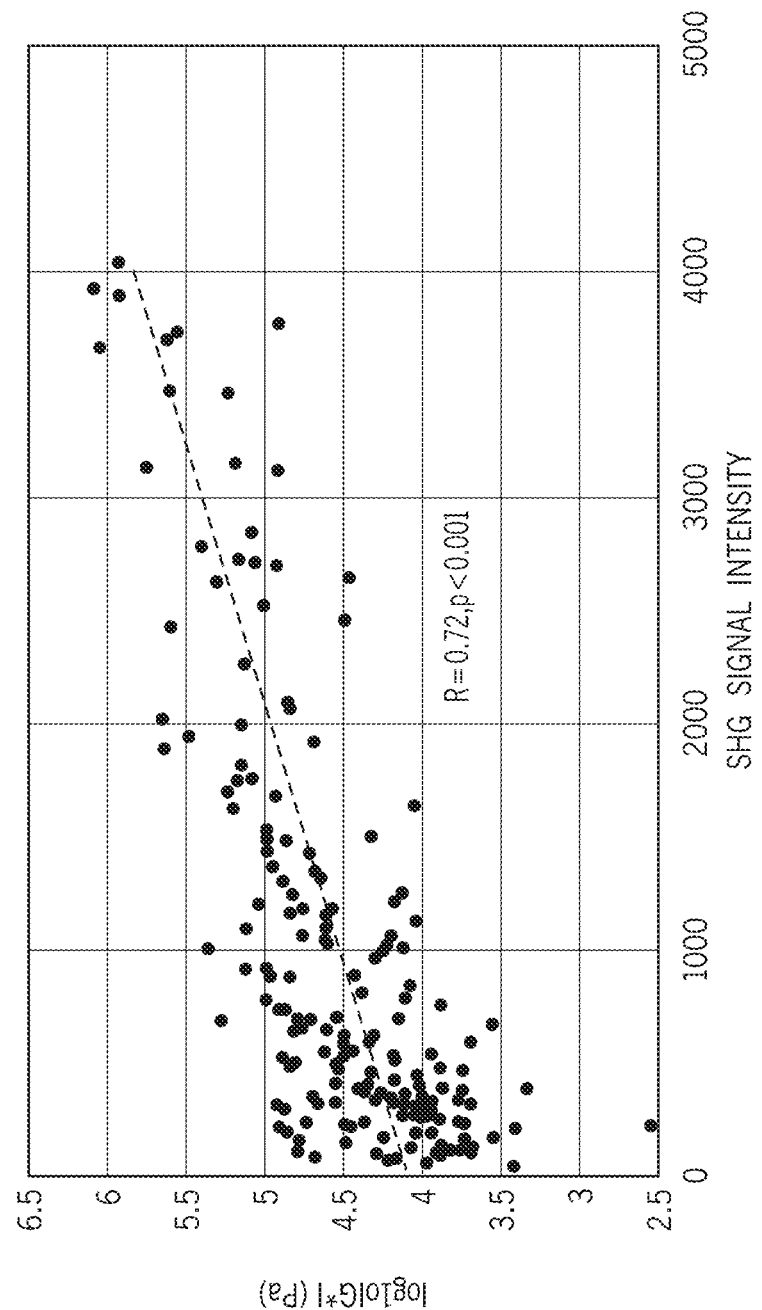
FIG. 21 provides the results of a regression analysis between $G^*$ values obtained by LSM and SHG signal intensity in specimens collected from 18 patients.

FIG. 21 displays the results of a regression analysis between G* values obtained by LSM and SHG signal intensity in specimens collected from 18 patients. The scatter diagram demonstrated a strong, statistically significant correlation between $G^*(\omega)$ and SHG signal (R=0.72, p<0.001). These findings highlight the ability of LSM to quantify the micro-mechanical signature of ECM in breast tumors at micro-scale resolution.

Discussion of LSM for Evaluating the Viscoelastic Properties of Hydrogel Scaffolds: Here we detailed the LSR framework for measuring the viscoelastic properties of hydrogels with unknown optical properties and scattering sizes and tested its accuracy via comparison with standard mechanical rheometry and AFM-based indentation. As shown, there is close agreement between LSR and rheometry, confirming that LSR accurately quantifies the complex frequency-dependent viscoelastic modulus, a metric representing both the viscous and elastic traits, over a wide range of deformation frequencies encountered in physiological processes and multiple decades of moduli. To establish the competence of LSR with the AFM-based indentation, the standard for micromechanical testing, we also demonstrated the correlation between the viscoelastic moduli, evaluated by LSR, and the indentation moduli, evaluated by AFM. Subsequently we showed that LSR resolves frequency-dependent viscoelastic moduli of micro-fabricated mechanical features in specialized gel substrates with high resolution and contrast. Taken together, these results proved that LSR merges the advantages of conventional rheometry for measuring frequency dependent viscoelastic behavior with the opportunity for micro-mechanical mapping afforded by AFM via a non-contact, all-optical approach.

We readily inferred the relative differences in viscoelastic properties of homogeneous hydrogels from the speckle fluctuations rates quantified by the $g_2(t)$ curves of FIG. 23A. The partially non-fluctuating speckle patterns of highly viscoelastic 3% agarose and 10% PEGDA were implicated in the higher plateau of $g_2(t)$ curves and revealed the substantial rigidity of the gel matrix entrapping intralipid particles. Still, to derive the bulk $|G^*(\omega)|$, LSR quantified and compensated for variations in optical properties. We maintained similar intralipid concentrations (1% w/v) in the hydrogels, thus one would expect identical optical properties of $\mu_a=0$ and $\mu_s' \sim 1$ mm$^{-1}$. Yet, DRP curves of FIG. 23B, obtained from time-averaged speckle frames, revealed substantially different $\mu_s'$ values caused by variations in curing processes and constituent materials. For instance, the partially demulsified intralipid particles in heated agarose solutions may have floated and re-coalesced to increase the $\mu_s'$ (4.3-17.5 mm$^{-1}$) in these samples. We also observed that the polymerization of low molecular weights (Mn=575) PEGDA increased the refractive index mismatch between the infused water and the emerging gel meshwork, creating a turbid hydrogel with increased $\mu_s'$ (10.4-15.3 mm$^{-1}$). In contrast, PA gels were transparent and the intralipid particles were evenly distributed in the polymer network, leading to $\mu_s'$ of 1 mm$^{-1}$, as would be expected.

Since the hydrogels in the hydrogel comparison were primarily scattering, $\mu_a$ was assumed to be effectively negligible, and only $\mu_s'$ was deduced from the logarithmic slope of DRP. This approach provided a reasonable approximation of the depth-integrated optical properties within the illuminated volume. In materials with heterogeneous and depth-varying scattering, the radially-resolved DRP may be measured to exploit photons remitted further away from the illumination spot that likely return from deeper regions. Accordingly, spatially-resolved optical properties may be extracted, assuming that DRP follows a piecewise model, with the slope of segments at distinct distances from the illumination center reflecting the optical properties of different layers. While in the current study, $\mu_a \sim 0$, for samples with non-negligible $\mu_a$, such as in blood, both $\mu_a$ and $\mu_s'$ can be estimated from the DRP.

Figure 23C:
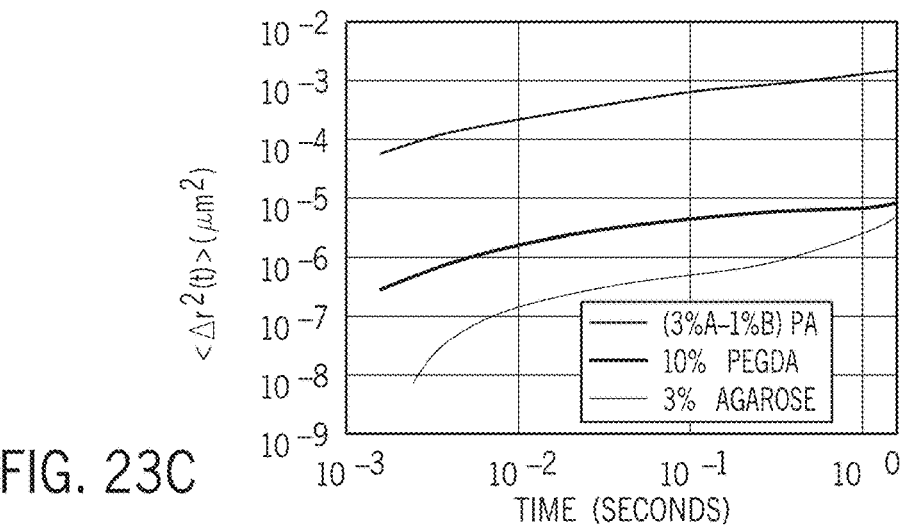
FIG. 23C provides the MSDs of intralipid particles within the hydrogels of FIG. 23A, obtained by replacing the $g_2(t)$ curves of FIG. 23A and the optical properties of the gels in the equation, derived from Correlation-Transfer Monte-Carlo Ray Tracing (CT-MCRT).
Figure 24A:
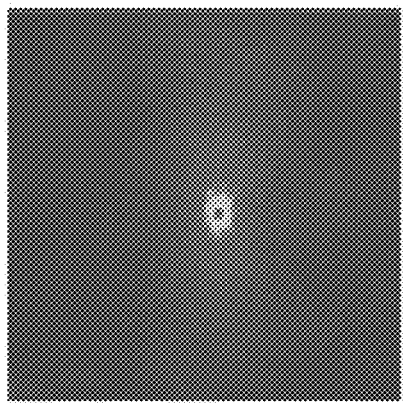
FIG. 24A provides the DRP of (3%-A, 1%-B) polyacrylamide (PA) gel obtained from temporally averaged speckle frame series, collected in parallel-polarized state with respect to illumination beam.
Figure 24B:
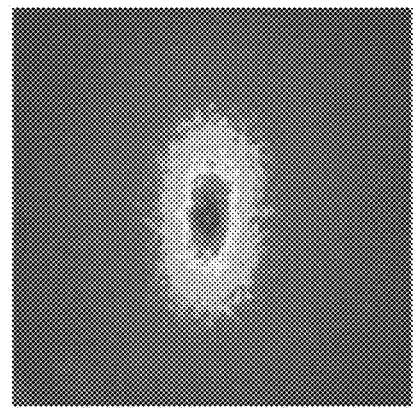
FIG. 24B provides the DRP of 10% polyethylene glycol diacrylate (PEGDA) gel obtained from temporally averaged speckle frame series, collected in parallel-polarized state with respect to illumination beam.
Figure 24C:
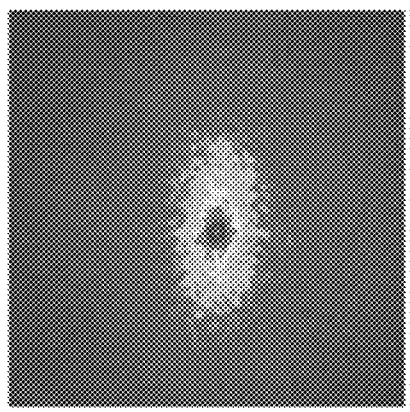
FIG. 24C provides the DRP of 3% agarose gel obtained from temporally averaged speckle frame series, collected in parallel-polarized state with respect to illumination beam.
Figure 24D:
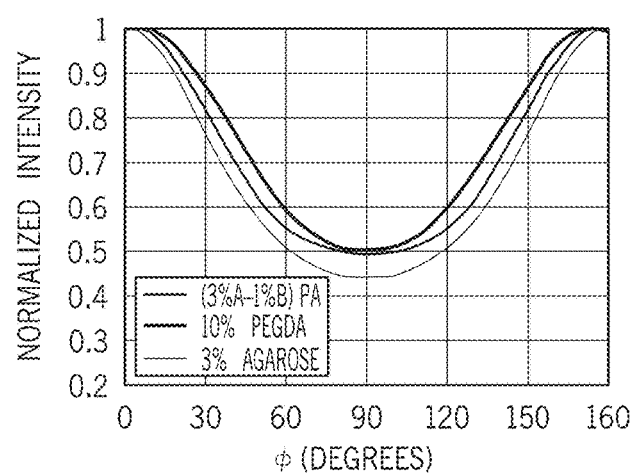
FIG. 24D provides normalized DRP values versus azimuth angle for the three gels of FIGS. 25A-C.

Next, we used a modified expression derived from our prior correlation-transfer Monte-Carlo ray tracing methods, to deduce the MSD curves of FIG. 23C (see Methods below). These curves were neither linearly growing as in purely viscous fluids nor flat similar to elastic solids, and represented the more complex viscoelastic behavior of hydrogels. For these porous gels that incorporated particles, the overall MSD was estimated to be a weighted average of the displacements of particles within the pores as well as the fibers. The MSD of probe particles at early time scales, was primarily diffusive and reflected the local hydrodynamics of the pores, whereas at longer times it converged to the MSD of fibers, which portrayed the bulk viscoelasticity of the gel meshwork. In such complex realistic gels, the MSD exhibited multiple relaxation times, commensurate with the structure of the gel.

Consequently, knowledge of scattering particle size was important for deducing the $G^*(\omega)$ from the MSD (Eqn. 4). The intralipid emulsions have a well-established size distribution. Published reports using dynamic light scattering (DLS) and electron microscopy studies estimate a mean radius of a ~100 nm for intralipid particles. We exploited a DLS-based particle sizer (ZetaSizer, Malvern Instruments, UK) to confirm that a=100 nm. Our experimental derivation of a=100 nm from the co-polarized DRP patterns (FIG. 22, box 6, and FIG. 24) matched these results.

The bulk $G^*(\omega)$ of homogeneous hydrogels can be obtained through replacing the MSD and a in Equation 4. We observed a close agreement between LSR and conventional rheometry measurements at 0.5-10 Hz frequencies and over moduli range of 47 Pa-36 kPa. LSR results were derived via Brownian dynamics induced by both shear and compressional thermal fluctuations. Compressional fluctuations dominated at low frequencies, causing LSR measurements to deviate from shear-based mechanical rheometry. This low frequency limit depended on the viscoelastic susceptibility and the microstructure of the specific material and varied from 0.01-0.1 Hz for primarily viscous biofluids, investigated in our prior work, to 0.1 Hz, for hydrogels evaluated here (see FIG. 25A). The upper frequency limit however was reached when inertial effects prevented sufficient straining of the specimen. In mechanical rheometry, at frequencies above 10 Hz, the strain waves generated by rheometer tool failed to penetrate across the gap between the parallel plates of the rheometer tool and merely sheared the sample surface, overestimating the high-frequency modulus. By contrast, in LSR the inertial effects only dominated when the penetration depth of shear waves became comparable to the scattering particle size. Therefore, the sub-micron sized scattering particles extended the onset of inertial effects beyond several hundreds of kHz, opening a new window of frequencies inaccessible to mechanical rheometry. The practical upper limit was further tied to the camera frame rate. In the current study, a frame rate of 739 fps limited the highest measurable frequency to below 100 Hz. By employing acquisition speeds of a few 100 kfps, higher frequencies, in the order of 105 Hz may be achieved.

Besides spanning a wide range of frequencies, LSR measured a considerable extent of moduli. We previously showed that LSR accurately quantified the moduli of extremely soft biofluids (on the order of a few mPa). The size of scattering particles, a, the ability to resolve their infinitesimal motions, $\delta_r$, and the thermal energy, $K_BT$, set the upper limit of moduli accessible to LSR to $KBT/(\delta_r^2 a)$. We clarified that the highly sensitive multi-speckle detection enabled resolving displacements of $\delta_r \sim Å$, as seen in FIG. 23C, leading to an upper limit of tens of kPa. For predominantly elastic materials, however, the nearly frozen speckle potentially returns a $g_2(t)$ curve that plateaus at unity and an MSD that flattens to zero, implying that thermal energy is inadequate for provoking a detectable displacement. Alternatively, intrinsic thermal fluctuations could be complemented with external stress fields to elicit detectable strains in considerably stiffer materials. The strong, statistically significant correlation between LSR and rheometry in hydrogels of unknown optical properties and particle sizes, observed in FIGS. 25A and B, paves the path for biomechanical evaluation of natural and synthetic tissue scaffolds with assorted composition, morphology, and microstructure.

Because a metric of interest is the viscoelastic modulus, here we sought to establish the ability of LSR to accurately quantify the G*. Nevertheless, since the only commercially available standard for micro-scale mechanical testing is AFM, we also investigated the correlation between LSR and AFM measurements. The high correspondence between |G*| measured by LSR at 1 Hz, and the indentation modulus, E, evaluated by AFM (FIG. 26B) suggested that LSR closely mirrors the micro-scale stress-strain measurements. Using various indentation rates in AFM could partially elucidate the frequency-dependence of E. However, the commercial AFM fell short in quantifying the complex, dynamic |E*| (similar to G* in LSR) unless coupled with a high-frequency actuator. Still, the contact-based AFM was not conducive to mechanical evaluation of soft and adhesive specimens, such as the (3% A-1% B) PA. In contrast, the non-contact nature of LSR permitted for evaluating adhesive and highly compliant materials, not easily assessed by AFM.

Spatially-resolved LSR measurements in the micro-fabricated phantom established the capacity of this new tool for evaluating the viscoelastic compliance at multiple frequencies and length scales to accommodate probing local mechanical heterogeneities (FIG. 27). In exemplary LSR systems, using a 10×, 0.25 NA objective, set the speckle grain size to 1.5 μm (airy disk) which was imaged on a 3×3 pixel array (pixel/speckle=9). Using a 25×25 Gaussian window for calculating the spatially-resolved $g_2(t)$ curves, the calculated lateral resolution for G* mapping (FIG. 27) was equal to 12.5 Through serpentine scanning and high-speed image acquisition, LSR could survey a 1 $cm^2$ area, with resolution of 12.5 μm within 20 minutes. AFM can potentially evaluate a map of static E through scanning the sample surface in steps and acquiring force-displacement curves at each location. However, obtaining each curve could take a few seconds, which would result in measurement times of several hours to evaluate a similar 1 $cm^2$ area. Moreover, the contact-based, invasive, and manipulative nature of AFM restrict the possibility of evaluating mechanical properties of cell-culture systems, under sterile conditions. Further, we have previously shown that due to the susceptibility of $g_2(t)$ curves to sub-wavelength scattering particle displacements, LSR is sensitive to moduli changes as small as $\Delta G^*=0.5$ Pa. Thus, LSR may likely be used to evaluate dynamic changes that occur due to ECM remodeling in biomimetic systems with high measurement sensitivity. For example, increasing the CMOS sensor bit depth from 8 to 16, acquiring more speckle spots, and/or collecting longer optical paths susceptible to rapid decorrelations could improve the LSR sensitivity to intensity fluctuations and slightly extend its dynamic range. Given its high spatial resolution and multi-frequency measurement capabilities, LSR provides a unique approach for investigating and developing synthetic tissue scaffolds. It also provides biologists with a new imaging tool to address key questions concerning the mechanosensitive regulation of cell morphology, physiology, and behavior by ECM components.

Constructing the micro-fabricated phantom with heterogeneities in the order of a few 10 s of microns was motivated by our goal to experimentally evaluate the resolution of the passive, depth-integrated LSM systems and demonstrate that features of distinct mechanical properties can be visualized with a spatial resolution of 10 s of μms. The size of features was chosen to demonstrate the potential application of this novel technology in evaluating the biomechanical properties of extracellular matrix at length scales relevant to a cluster of a few cells. The results of FIGS. 27 and 28 clearly demonstrate the success of LSR technology in achieving this goal. Nevertheless, since soft lithography techniques suffer from an inherent limitation on the aspect ratio (width/depth) of the features that can be engraved on the silicon wafer, fabricating a phantom with more refined features is extremely challenging and pose a limitation on using such phantoms to experimentally verify the calculated resolution of LSM system.

In FIGS. 27 and 28, heterogeneous moduli are observed within the bars. This demonstrates the resolution and sensitivity of the passive LSM to variations in the viscoelastic modulus at length scales in the order of a few 10 s of microns. These heterogeneities are likely caused due to small variations in mixing, pouring, curing, and peeling of PDMS elastomers, in the process of soft lithography, as well as irregularities in plasma bonding of PDMS and glass coverslip, which may lead to the leakage of PEGDA to the spaces were the glass has failed to properly attach to the PDMS.

Results of FIG. 28 represent LSM measurements obtained from a micro-fabricated phantoms with smaller differences between the modulus of the bars and the background gel. FIGS. 28 A-D display the bright-field image and the 2D spatially-resolved LSR color-map of |G*(ω)| within the micro-patterned substrate, composed of PEGDA 10% (G*=6.5±1.5 kPa@ 1 Hz) and PDMS (G*10.8±2.1 kPa @ 1 Hz) at 1, 10, and 100 Hz. Since both PEGDA10% and PDMS gels are stiff, they are easier to cast and microfabricate. Therefore, it is less challenging to outline the two materials and more defined borders and higher resolution is achieved in assembly of the composite material as observed in both bright field and LSR images. In addition, the bars also appear less heterogeneous, likely due to consistency in casting the PEGDA10%-PDMS phantom, and reduced leakage between the compartments given the stiffer gels. Moreover, since the difference between the moduli of the background and the bars are smaller, the contrast between the two sections is reduced, as evidenced by yellow to dark orange hue of the background which is closer to the red hue of the bars. As such, compared to FIG. 27, the background PEGDA 10% gel exhibits higher G* at all frequencies in FIG. 28, and these results establish that small differences in mechanical contrast can be detected using LSR.

While the invention is described through the above-described examples of embodiments, it will be understood by those of ordinary skill in the art that modifications to, and variations of, the illustrated embodiments may be made without departing from the inventive concepts disclosed herein. For example, and in further reference to FIG. 1, while the use of an interferometer in acquitting the optical data provides sufficient rejection of multiply scattered light, additional filtering can be optionally provided by optional use of the polarization-sensitive light detection. To this end, appropriate polarization optics, for instance a polarization beam splitter, can be additionally incorporated into an embodiment. As another modification, for accurate determination of $G(\omega)$, time-averaging of $g_2(t)$ distributions may be required. In addition to time averaging, spatial averaging of $g_2(t)$ over neighboring pixels can be conducted or, alternatively, to maintain high spatial resolution for $G(\omega)$ mapping, time averaging can be conducted over longer durations. In order to mitigate artifacts of motion within the measurements system such as the system of FIG. 1, sample 130 can be will be secured on a vibration-isolated platform and, alternatively or in addition, time-averaging and Fourier domain filtering of $g_2(t)$ distributions can be implemented to remove residual instabilities. In another related embodiment, the frequency dependent modulus is determined through the decorrelation-time constant, $\tau$, that is determined from $g_2(t)$ curves at each pixel or, alternatively or in addition, over neighboring pixels from the time-varying 3D speckle image series. For example, the time constant $\tau$ can be measured by fitting a single of multiple exponential functions to measure the rate of laser speckle fluctuations.

Various disclosed aspects and features of the invention may be combined in ways not listed above. Accordingly, the invention should not be viewed as being limited to the disclosed embodiment(s).

In the realistic cell systems, the concentration of scattering particles, and in turn the optical properties, will be heterogeneous, varying spatially and with depth. In the depth-integrated passive LSM system, where laser coherence length is long, and the reference arm is removed, we use the steady-state diffusion approximation to evaluate the average $\mu_s'$ over the illuminated volume, which extends several mean free path lengths, $l^*=1/\mu_s'$, in both transverse and axial directions'. This approach provides a reasonable first order approximation of the diffuse reflectance profile (DRP) of the illuminated volume. Thus, the measured optical properties are integrated over the illumination depth for each beam location. To enable evaluating the optical properties within a spatially heterogeneous media, the focused laser beam may be scanned transversally in fine steps across the sample to enable estimating the depth-integrated, but laterally resolved, $\mu_s'$. However, if spatial heterogeneities exist along the depth, such as for instance in layered tissues and cell systems, additional processing steps may be taken to extract the depth-resolved optical properties as detailed below.

In particular, we and others have demonstrated that the light diffusion approximation remains valid even in the case of multi-layered tissue and may be used to describe the propagation of photon flux. The diffusion properties of light propagation and Monte-Carlo ray tracing simulations illustrate that the photons returning from deeper regions within the tissue have a higher probability of being remitted farther away from the illumination beam entry point. We have exploited the light remitted from the vicinity of the illumination spot to estimate the optical properties of the superficial layer in bi-layer models of tissue. Others have derived an alternative equation for the DRP curve as a function of the optical properties within the layers beneath the surface. Accordingly, the DRP follows a piecewise model, with the slope of segments at different radial distances from the illumination point representing the optical properties of a certain depth below the surface. As such, at distances close to illumination center, the slope of the DRP curve reflects the optical properties of the superficial layer, whereas at distances further away from the source, the DRP slope is more influenced by the optical properties of the deeper layers. The contribution of layers to the DRP at each radial distance depends on both the thicknesses of layers and the relative differences of optical properties along the depth. We have also previously exploited this fact to map the laser speckle fluctuations at different distances from the illumination beam to the specific depths below the surface and obtained indices of viscoelasticity in bilayer tissues such as for instance necrotic core fibroatheroma (NCFA) plaques, with a stiffer fibrous layer, overlying a low viscosity lipid pool. Therefore, both DRP and speckle intensity autocorrelation, $g_2(t)$, may be evaluated as a function of radial distance from the illumination center. The radial variations of DRP return the optical properties along the depth of the tissue. The resultant optical properties, together with radially-dependent $g_2(t)$, then will likely yield the MSD for distinct tissue layers and in turn the G*. In this way, knowledge of optical properties and speckle dynamics as a function of depth, in principle will likely minimize the potential errors in estimating the G* of individual layers.

While the long-coherence passive LSM system and its processing algorithm could provide an elegant and simple way to assess depth-resolved optical and mechanical properties, the measurement of the DRP exploits multiple scattering within the tissue to calculate optical properties and therefore will likely limit the depth resolution. Alternatively, coherence-gated methods, such as for instance the 100 embodiment, may be used to acquire speckle patterns or a single speckle spot at selected depths within the tissue with respect to a scanning reference arm as in holographic microscopy or low coherence interferometric methods to probe local speckle dynamics. Using such coherence-gated methods, speckle intensity fluctuations may be measured to provide depth-resolved mechanical properties with improved depth-resolution.

Some of the key biological questions and mechanobiological hypotheses call for evaluating mechanical properties with high-spatial resolution. Currently, the majority of hypotheses in mechanobiology and mechanotransduction, are developed based on bulk rheology measurements of gel scaffolds usually obtained by standard mechanical testing, prior to cell seeding. These measurements, however, are unable to quantify spatial heterogeneities and dynamic changes that may occur over time, thus provide only a static snapshot of the role of bulk mechanical properties in regulating cell morphology, growth, proliferation, and migration. AFM-based techniques may enable researchers to probe the stiffness at sub-micron resolutions over superficial tissue layers. However, these measurements are contact-based, invasive, only measure over small scan area (<100×100 μm), and require long measurement times (several hours for mapping), thus restricting the possibility of evaluating mechanical properties within the pericellular matrix (PMC) of cell-culture systems, under sterile conditions. In our opinion, given its capability for non-contact evaluation of mechanical properties rapidly (<20 minutes) over a large scan area (~several mm) at a high spatial resolution, LSR provides a major advantage over these traditional methods.

The passive LSM system depicted in FIG. 1 A, has a lateral resolution equal to 12.5 μm (for a 10× objective; NA=0.25). This resolution is achieved noting that the diffraction limit, i.e. the size of Airy disk or individual speckle grain for such an objective is 1.22λ/(2NA)=1.5 μm in the object plane. This indicates that the objects that are 1.5 μm apart in the object plane can be resolved by a 10× objective. On the other hand, combined magnification of the objective and tube lens, together with NA and camera pixel pitch, determine the sampling volume of the system and indicate that a length of 0.5 μm in the object plane is mapped to a single pixel in the image plane, as verified by imaging a 1951 USAF resolution test chart. Therefore, each speckle grain of 1.5 μm size is projected on a 3×3 array of pixels in the image plane, leading to pixel to speckle ratio of 9. Additional spatial averaging, using a 25×25 Gaussian window reduces the resolution to 25/3*1.5 μm=12.5 μm. With a spatial resolution of 12.5 μm (using a 10×, 0.25 NA objective), LSM technology provides mechano-biologists with a tool for testing and addressing key biomechanical questions at length scales pertinent to a cluster of a few cells. Examples of some the hypothesis that can be tested using the current LSM platform are related to investigating the mechanical regulation of malignant transformation and tumorigenesis, the role of ECM stiffness gradients in motivating the preferential migration of cancer cells during metastatic progression, the influence of biomechanical cues imparted by PCM in altering cell shape and morphology, and the mechano-regulation of fibrosis in a variety of pathological conditions, such as scleroderma, aberrant wound healing and scarring, as well as lung fibrosis.

The resolution of the passive, depth-integrated LSM system is influenced by the following:
1. Optical diffraction limit, set by the numerical aperture of imaging optics.
2. Spatial and temporal contrast of the speckle pattern grains, e.g. speckle to pixel ratio.
3. The extent of spatio-temporal averaging windows, used to increase the statistical accuracy of speckle intensity autocorrelation function, $g_2(t)$, evaluated for individual pixels of the speckle frame series.

Below is a summary of how these factors may influence the ultimate resolution of the LSR system:

(1) Optical diffraction limit: In principle, the resolution of G* maps may not exceed the resolution of imaging optics. In the current optical setup, we have used a set of objective lenses, namely 4× (NA=0.1), 10× (NA=0.25), 20× (NA=0.4). At a source wavelength of λ=632 nm, these objectives set the diffraction limit, i.e. airy disk size or speckle grain size, (1.22λ/(2×NA)) to 3.85, 1.5, and 0.96 μm, in the object plane, respectively. The diffraction-limited resolution and the resultant speckle size can be improved by using objectives of higher NA and magnification.

(2) Sufficient spatial and temporal contrast is needed to avoid blurring of the speckle grains, which could reduce the spatial resolution and contrast of G* maps. To overcome this issue, speckle patterns should be fully developed in both space and time, with the intensity levels spanning the full pixel depth of the CMOS. The high-speed Basler camera in the current LSR setup has 2046×1086 pixels with a 0.6 μm pixel pitch (in the image plane) and is operated at 8 bit pixel depth (intensity levels: 0-255). The combination of objective and tube lens numerical apertures and magnification, together with camera pixel size, determine that lengths of 1.3, 0.5, and 0.3 μm in the object plane are projected to a single pixel in the imaging plane, when 4×, 10×, and 20× objectives are used, respectively. Based on the diffraction-limited speckle sizes calculated above for these objectives, i.e. 3.85, 1.5, and 0.96 μm, and the corresponding length of single pixels (1.3, 0.5, and 0.3 μm), a pixel to speckle ratio of 9 is obtained for all magnifications, which helps ensure sufficient spatial speckle contrast. Moreover, the camera frame rate also influences the overall spatial resolution given its influence on speckle contrast. Using the high frame rate acquisition capability of the CMOS, operated at 250 and 739 fps in the current study, permits sufficient temporal sampling of speckle fluctuations and enables tracking the rapid dynamics of the speckle patterns, thus reducing the influence of speckle blurring.

(3) The amount of spatial and temporal averaging: In LSR sufficient ensemble averaging of temporally fluctuating speckle spots is required in order to calculate the MSD with sufficient statistical accuracy. This can be achieved by using a combination of spatial and temporal averaging of fluctuating speckle patterns. Combined spatio-temporal averaging may be accomplished by sliding a moving-average spatial Gaussian window across the pixels of the speckle patterns and by time-averaging multiple $g_2(t)$ curves that evolve in time. Such windowed spatio-temporal allows ensemble averaging over multiple speckle spots thus requiring short acquisition times albeit at the cost of reduced spatial resolution of the G* map. In the current LSR processing scheme, a 25×25 Gaussian window has reduced the theoretical resolution to 30, 12.5, and 7.5 μm for the 4×, 10×, and 20× objectives respectively. The spatial resolution may be improved by exploiting a smaller moving average window, but at the expense of acquiring speckle images for longer times to compensate and trade the reduced spatial averaging with increased temporal averaging of multiple $g_2(t)$ curves that evolve in time.

While the spatial resolution of the passive, long-coherence LSM permits measurement of spatial heterogeneities (discussed above), it is the high measurement sensitivity of LSM that enables tracking of dynamic changes in mechanical properties. The acute sensitivity of LSM to changes in viscoelastic modulus stems from the susceptibility of $g_2(t)$ curves to sub-wavelength scattering particle displacements. In other words, changes in the viscoelastic properties alter particle displacements in the sample, and particles in the illumination volume displaced just by a fraction of an optical wavelength induce a significant cumulative phase shift in the optical paths, which drastically modulates the intensity of individual speckle spots. The sensitivity of LSM is dependent on the capability of the CMOS camera to detect small changes in speckle intensities and is in turn influenced in part by the bit depth of the CMOS sensor. Using an 8-bit (10 tap) bit depth CMOS sensor, we have previously shown that the measurement sensitivity of LSR is on the order of <1 Pa. For instance, our prior studies that compared G* measurements of LSR with mechanical rheometry in coagulating blood specimens revealed that LSR is sensitive to moduli changes as small as ΔG*=0.5 Pa. We expect that this level of sensitivity is sufficient to track dynamic changes caused during gel remodeling in biomimetic systems. We have also previously shown that LSR can track differential changes, i.e. ΔG*, as small as tens of Pa, in the viscoelastic modulus of curing PDMS substrates[5]. By using 10, 12 or 16 bit depth CMOS sensors, LSR sensitivity can likely be further improved if necessary.

Figure 30:
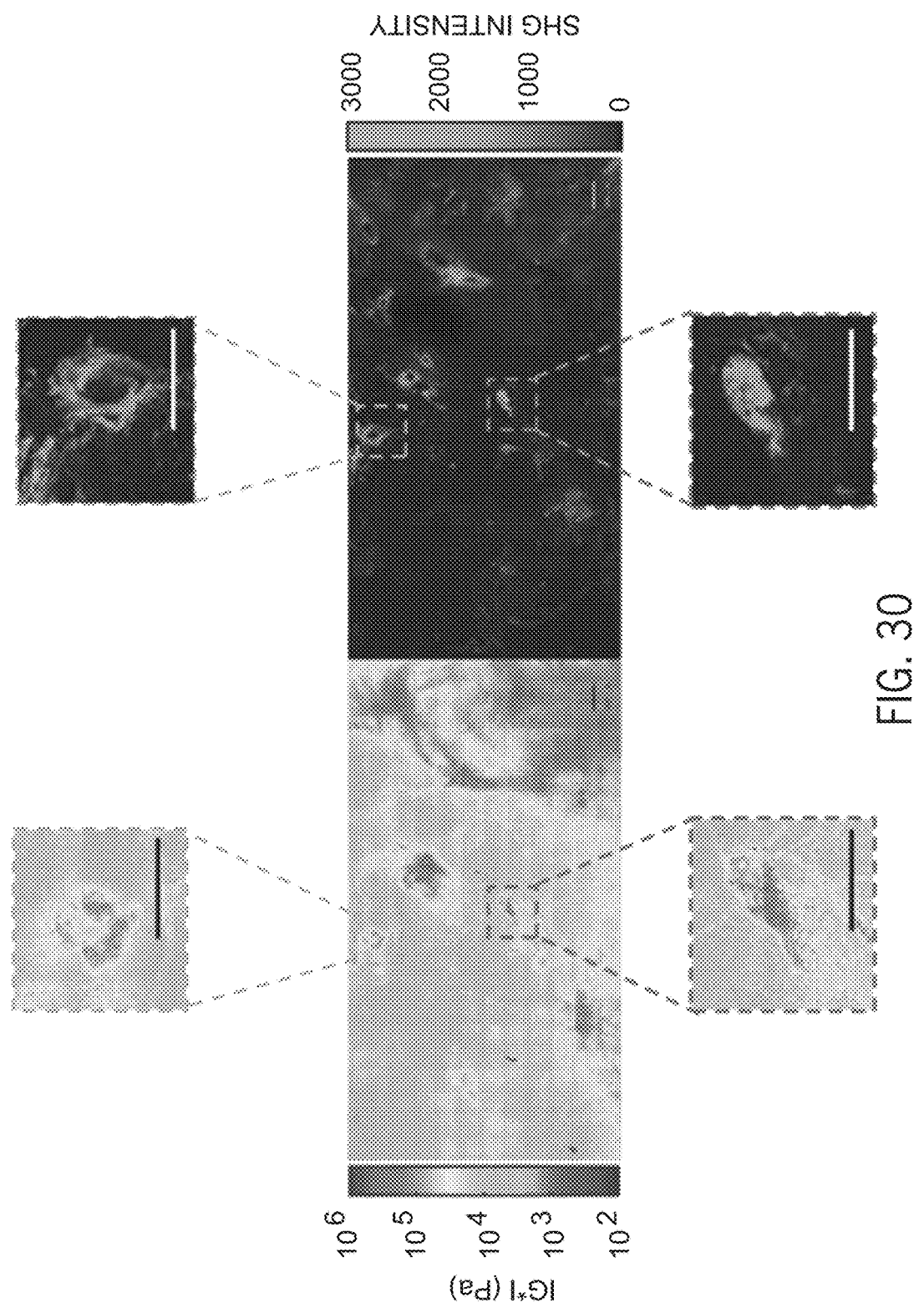
FIG. 30 displays the Magnitude of viscoelastic modulus, |G*| at 100 Hz and SHG signal intensity within an invasive ductal carcinoma (IDC) human breast tumor specimen. Distinct mechanical features in the order of a few 10 s of microns can be identified within the G* maps, corresponding to regions of collagen accumulation and alignment in the SHG image. Scale bars are 250 microns.

As mentioned above, the theoretical limit for the spatial resolution of the passive, long-coherence LSM system is about 12.5 microns (10× objective, NA=0.25). The following results demonstrates the capability of LSM to detect viscoelastic variations at length scales of 10 s of microns in real biological tissue, exhibiting significant structural, morphological, compositional, and mechanical heterogeneities. FIG. 30 displays the LSM measurements of |G*| and the comparative second harmonic generation (SHG) microscopy, revealing the collagen content and structure, within an invasive ductal carcinoma human breast tumor specimen. From this figure it seems that collagen, the major contributor to the tensile strength of the tumor tissues, is also the dominant source of the scattering signal. The SHG image is used to verify the accuracy of the G* map, obtained using the LSM. The magnified panels clearly show that mechanically distinct features, over lengths scales of a few 10 s of microns, resembling small ducts surrounded by stiffened ECM are readily resolved in the LSR images, and closely correspond to regions of bundled and aligned collagen in the SHG images. These results demonstrate that the passive, depyh-integrated LSM is capable of resolving features of distinct mechanical properties and stiffness, created by accumulation and alignment of collagen fibers, in the order of a few 10 s of micron over a large field of view.

We have also previously demonstrated the success of LSR-based approaches in biomechanical evaluation of fibrin-platelet clots. When a porous gel meshwork incorporates particles, the overall MSD is estimated to be a weighted average of the displacements of particles, bound in the pores of the fibrin gel, as well as the fibers. The dominant MSD behavior partially depends on the relative contribution of the two components to the total $\mu_s'$ and well as the time scale at which MSD is evaluated. More specifically, the gel mesh may be treated as a poly-disperse scattering medium, in which the effective $\mu_s'$ may be written as:

$$\mu_{s\ eff}' = \mu_{s\ particles}' + \mu_{s\ fibers}' \quad (5)$$

Accordingly, the overall MSD turns to be:

$$MSD_{eff} = MSD_{particles} \frac{\mu_{s\ particles}'}{\mu_{s\ eff}'} + MSD_{fibers} \frac{\mu_{s\ fibers}'}{\mu_{s\ eff}'} \quad (6)$$

Therefore, the higher scattering component (either particulate or fibrous constituents) will be the major contributor to the effective scattering of the sample and dominate the effective MSD trend. Furthermore, previous work has shown that the particles confined within the gel meshwork may be simply modeled by a sphere, connected to an un-stretched harmonic spring, in a viscous fluid. According to this model, the initial particle displacements at early times are diffusive. Nevertheless, they eventually come at rest in the proximity of the mesh and the elastic forces dominate. Therefore, the MSD of probe particles at early time scales, is primarily diffusive and reflects the local hydrodynamics of the pores, whereas at longer times it converges to the MSD of fibers, which portrays the bulk viscoelasticity of the gel meshwork. In such complex realistic gels, the MSD may exhibit multiple relaxation times, commensurate with the structure of the gel. Therefore, depending on the scattering signal strength of particles and fibers and the time scales of measurements, the complex effective MSD is a weighted average of both local and global dynamics of the gel network.

The methods described here are not limited to samples with negligible absorption. In fact, both absorption and reduced scattering coefficients, $\mu_a$ and $\mu_s'$ can be extracted from the normalized DRP curve. In the phantom viscoelastic gels presented here, since the intra-lipid was primarily scattering, we simplified the derivations by assuming that $\mu_a$ is negligible. Under these circumstances, the reduced scattering coefficient, $\mu_s'$ was simply derived from the logarithmic slope of the DRP curve, which was obtained from temporally averaged speckle frame series.

If on the other hand, $\mu_a$ is non-negligible, the conventional DWS formalism may be used to express the $g_2(t)$ in terms of MSD and the optical properties of the specimen, according to:

$$g_2(t) = e^{-2\gamma \sqrt{k_0^2 \langle \Delta r^2(t) \rangle + \frac{3\mu_a}{\mu_s'}}} \quad (7)$$

In samples with non-negligible absorption such as blood, we have previously shown that both $\mu_a$ and $\mu_s'$ can be estimated by fitting the radial diffuse reflectance profile (DRP) to a model derived from steady-state diffusion theory to calculate both $\mu_a$ and $\mu_s'$ according to:

$$DRP(r) = \frac{\mu_s'}{4\pi(\mu_a + \mu_s')} \quad (8)$$

$$\left[\frac{1}{\mu_a + \mu_s'}\left(\mu_{eff} + \frac{1}{r_1}\right)\frac{e^{-\mu_{eff} r_1}}{r_1^2} + \left(\frac{7}{3(\mu_a + \mu_s')}\right)\left(\mu_{eff} + \frac{1}{r_2}\right)\frac{e^{-\mu_{eff} r_2}}{r_2^2}\right]$$

$$r_1 = \left[\left(z - \frac{1}{\mu_a + \mu_s'}\right)^2 + r^2\right], \quad (9)$$

$$r_2 = \left[\left(z + \frac{7}{3(\mu_a + \mu_s')}\right)^2 + r^2\right]$$

$$\mu_{eff} = \sqrt{3\mu_a(\mu_a + \mu_s')}$$

Subsequently, $\mu_a$ and $\mu_s'$ were replaced in the DWS equation above to deduce the MSD of scattering particles from the $g_2(t)$ curves, in specimens of non-negligible absorption coefficient. When computational time and resources are limited, the task of independently calculating both coefficients from the radial profile of DRP may be avoided by noting that all we require is the ratio of the two. The ratio, $\mu_a\mu_s'$, can be simply evaluated by measuring the total reflectance of the specimen (as compared to a standard reference of known reflectivity).

More specifically, to evaluate the total reflectance, $R_d$, a diffuse reflectance standard with reflectance factor of $R_{std}$, is evaluated with the LSR system. Speckle movies are acquired with the same frame rate and acquisition time used to evaluate the sample of interest. The frames are averaged both temporally and spatially to measure the mean pixel value, $M_{std}$. Since all measurements are relative, as long as the same laser power, detector aperture, and sensitivity are maintained, it is not necessary to convert pixel values to absolute intensity. When evaluating the sample of interest, spatio-temporally averaged pixel value, M, is evaluated similar to the reference standard. Subsequently, $R_d$ is calculated as: $R_d = M/M_{std} \times R_{std}$. The total reflectance may be approximated by:

$$R_d = \frac{1}{1 + 6.9683\frac{\mu_a}{\mu_s'} + 2.9894\sqrt{3\frac{\mu_a}{\mu_s'}\left(1+\frac{\mu_a}{\mu_s'}\right)}} \quad (10)$$

Subsequently, $\mu_a/\mu_s'$ may be derived from the equation above using simple change of variables and trivial algebraic manipulations.

What is claimed is:

1. A method for determining a mechanical property of biological tissue using laser speckle microrheology, the method comprising:
receiving speckle frames output by an optical detector that were acquired by illuminating the biological tissue using a laser;
performing a time-averaged analysis of the speckle frames by:
calculating a first diffuse reflectance profile (DRP) from a first subset of the speckle frames;
calculating a second DRP from a second subset of the speckle frames;
determining a scattering coefficient ($\mu_s'$) and an absorption coefficient ($\mu_a$) of the biological tissue using the first DRP;
evaluating a size characteristic of scattering particles (a) using the second DRP, wherein a is determined based on a ratio of intensity of the second DRP along a first direction to intensity of the second DRP along a second direction;
performing a time-resolved analysis of the speckle frames by:
cross-correlating a first speckle frame with subsequent frames to return a speckle intensity auto-correlation function ($g_2(t)$);
determining mean square displacement (MSD) using $g_2(t)$ and at least one of $\mu_s'$ and $\mu_a$; and
generating a report indicating frequency-dependent viscoelastic modulus, $G^*(\omega)$, using a and MSD.

2. The method of claim 1, wherein calculating the first DRP includes performing a temporal averaging of speckle frames.

3. The method of claim 1, wherein determining $\mu_s'$ includes performing a curve-fitting to the first DRP.

4. The method of claim 1, wherein $g_2(t) = \exp(-2\gamma(k^2 \langle \Delta r^2(t) \rangle)^\zeta)$, where $\gamma$ and $\zeta$ are empirical variables related to $\mu_s'$ and $\mu_a$, $\langle \Delta r^2(t) \rangle$ is the MSD of light-scattering particles in the biological tissue, and k is a wavenumber.

5. The method of claim 1, wherein the second subset of speckle frames are parallel-polarized with respect to a polarization of light from the laser, and a is determined by comparing a ratio of the second DRP along short and long axes of the second DRP with calibration curves.

6. The method of claim 1, wherein the $G^*(\omega)$ is calculated by substituting MSD and a in a generalized Stokes-Einstein relation (GSER).

7. The method of claim 1, further including forming a three-dimensional (3D) map of the mechanical property of the biological tissue by:
calculating two-dimensional (2D) distributions of the viscoelastic modulus of the biological tissue at a plurality of depths; and
mapping the 2D distributions into a 3D data set representing the distributions of the viscoelastic modulus in relation to the plurality of depths of the biological tissue;
wherein the time-averaged and time-resolved analyses are performed for each of the plurality of depths.

8. The method of claim 7, wherein the viscoelastic modulus at each depth corresponds with stiffness of the tissue extra-cellular matrix (ECM) at the depth.

9. A method for determining a mechanical property of biological tissue using laser speckle microrheology, the method comprising:
receiving speckle frames acquired by illuminating the biological tissue with a coherent light source and capturing, using an optical detector, back-scattered rays from the biological tissue in parallel-polarized and cross-polarized states with respect to a linear polarization of the coherent light source;
analyzing the speckle frames temporally to obtain a first diffuse reflectance profile (DRP) for the parallel-polarized state and a second DRP for the cross-polarized state;
determining a scattering characteristic or an absorption characteristic of particles in the biological tissue based on at least on of the first DRP or the second DRP;
determining a displacement characteristic based at least in part on a speckle intensity autocorrelation function and at least one of the scattering characteristic and the absorption characteristic;
determining a size characteristic of scattering particles based on a ratio of intensity of the first DRP along a first direction to intensity of the first DRP along a second direction; and
calculating the mechanical property using the displacement characteristic and the size characteristic.

10. The method of claim 9, wherein the mechanical property is an elastic modulus of the biological tissue.

11. The method of claim 10, wherein calculating the elastic modulus comprises using a generalized Stokes-Einstein relation (GSER).

12. The method of claim 9, wherein analyzing the speckle frames temporally comprises temporally averaging speckle intensity.

13. The method of claim 9, wherein the displacement characteristic is based on the absorption characteristic, wherein the absorption characteristic is an absorption coefficient of the biological tissue.

14. The method of claim 9, wherein the speckle intensity autocorrelation function is obtained by cross-correlating a first speckle frame with subsequent frames.

15. The method of claim 9, wherein the scattering characteristic is mean square displacement (MSD) of light-scattering particles.

16. The method of claim 9, wherein the size characteristic is an average radius of scattering particles.

17. The method of claim 9, wherein the ratio is compared with a calibration curve to determine the corresponding particle size characteristic.

18. The method of claim 9, wherein the scattering characteristic is a scattering coefficient, and wherein the second DRP is fitted to a model of light diffusion to extract the scattering coefficient therefrom.

19. The method of claim 9, further including forming a three-dimensional (3D) map of the mechanical property of the biological tissue using the speckle frames by:
calculating two-dimensional (2D) distributions of the mechanical property of the biological tissue at a plurality of depths of the tissue layer; and
mapping the 2D distributions into a 3D data set representing the distributions of the mechanical property in relation to the plurality of depths to obtain a 3D distribution of the mechanical property at the plurality of depths;

wherein the mechanical property is calculated using the displacement characteristic and the size characteristic for each of the plurality of depths.

20. The method of claim 19, wherein a 3D distribution of stiffness of the extra-cellular matrix (ECM) of the biological tissue is formed.

21. A system for determining a mechanical property of biological tissue using laser speckle microrheology, the system comprising a processor and memory with instructions thereon, the processor being configured to:

receive speckle frames acquired by illuminating the biological tissue with a coherent light source and capturing, using an optical detector, back-scattered rays from the biological tissue in parallel-polarized and cross-polarized states with respect to a linear polarization of the coherent light source;

analyze the speckle frames temporally to obtain a first diffuse reflectance profile (DRP) for the parallel-polarized state and a second DRP for the cross-polarized state;

determine a scattering characteristic or an absorption characteristic of particles in the biological tissue based on at least one of the first DRP or the second DRP;

determine a displacement characteristic based at least in part on a speckle intensity autocorrelation function and at least one of the scattering characteristic and the absorption characteristic;

determine a size characteristic of scattering particles based on a ratio of intensity of the first DRP along a first direction to intensity of the first DRP along a second direction; and calculate the mechanical property using the displacement characteristic and the size characteristic.

22. The system of claim 21, wherein the mechanical property is an elastic modulus of the biological tissue, and wherein the processor is configured to calculate the elastic modulus using a generalized Stokes-Einstein relation (GSER).

23. The system of claim 21, wherein analyzing the speckle frames temporally comprises temporally averaging speckle intensity.

24. The system of claim 21, wherein the processor is configured to base the displacement characteristic on the absorption characteristic, wherein the absorption characteristic is an absorption coefficient of the biological tissue.

25. The system of claim 21, wherein the processor is further configured to obtain the speckle intensity autocorrelation function by cross-correlating a first speckle frame with subsequent frames.

26. The system of claim 21, wherein the scattering characteristic is mean square displacement (MSD) of light-scattering particles.

27. The system of claim 21, wherein the size characteristic is an average radius of scattering particles.

28. The system of claim 21, wherein the processor is configured to determine the size characteristic based on azimuth-angle dependence of the first DRP by:

determining a ratio of intensity at azimuth angle ninety degrees to intensity at azimuth angle zero degrees, wherein azimuth angle zero corresponds to a maximum intensity of the first DRP; and comparing the ratio with a calibration curve to determine the corresponding particle size characteristic.

29. The system of claim 21, wherein the processor is further configured to form a three-dimensional (3D) map of the mechanical property of the biological tissue using the speckle frames by:

calculating two-dimensional (2D) distributions of the mechanical property of the biological tissue at a plurality of depths of the tissue layer; and mapping the 2D distributions into a 3D data set representing the distributions of the mechanical property in relation to the plurality of depths to obtain a 3D distribution of the mechanical property at the plurality of depths;

wherein the mechanical property is calculated using the displacement characteristic and the size characteristic for each of the plurality of depths.

30. The system of claim 29, wherein a 3D distribution of stiffness of the extra-cellular matrix (ECM) of the biological tissue is formed.

31. A method for determining a mechanical property of biological tissue using laser speckle microrheology, the method comprising:

acquiring speckle frame series by illuminating a laser light and capturing, using an optical detector, back-scattered rays from the biological tissue in parallel-polarized and cross-polarized states with respect to a linear polarization of the laser light;

calculating a speckle intensity autocorrelation curve;

temporally averaging speckle intensity, and calculating a first radial diffuse reflectance profile (DRP) for the parallel-polarized speckle frame series and a second radial DRP for the cross-polarized speckle frame series;

fitting at least one of the first radial DRP or the second radial DRP to a steady-state diffusion model to extract a scattering coefficient;

deducing mean square displacement (MSD) of light-scattering particles based on the speckle intensity autocorrelation curve and the scattering coefficient;

calculating a ratio of intensities of the first DRP along short and long axes, and comparing the ratio with a calibration curve to determine average radius of scattering particles; and calculating a viscoelastic modulus for the biological tissue using the MSD and the average radius of scattering particles.

* * * * *

UNITED STATES PATENT AND TRADEMARK OFFICE
CERTIFICATE OF CORRECTION

PATENT NO. : 10,359,361 B2
APPLICATION NO. : 15/431372
DATED : July 23, 2019
INVENTOR(S) : Seemantini K. Nadkarni et al.

It is certified that error appears in the above-identified patent and that said Letters Patent is hereby corrected as shown below:

In the Specification

Column 21, Line 32, "p<10" should be --$p<10^{-4}$--.

Column 21, Line 33, "p<10" should be --$p<10^{-4}$--.

Signed and Sealed this
Twenty-ninth Day of October, 2019

Andrei Iancu
*Director of the United States Patent and Trademark Office*